US008734631B2

(12) United States Patent
Ahrens et al.

(10) Patent No.: US 8,734,631 B2
(45) Date of Patent: May 27, 2014

(54) CHEMISTRY USED IN BIOSENSORS

(75) Inventors: Michael Ahrens, Evanston, IL (US);
Paul A. Bertin, Chicago, IL (US);
Amanda Eckermann, Evanston, IL (US); Dimitra Georganopoulou,
Chicago, IL (US); Harry B. Gray,
Pasadena, CA (US); Thomas J. Meade,
Evanston, IL (US); Markus Franz Wunder, Evanston, IL (US)

(73) Assignee: OHMX Corporation, Evanston, IL (US)

( * ) Notice: Subject to any disclaimer, the term of this patent is extended or adjusted under 35 U.S.C. 154(b) by 672 days.

(21) Appl. No.: 12/253,875

(22) Filed: Oct. 17, 2008

(65) Prior Publication Data

US 2009/0253149 A1 Oct. 8, 2009

Related U.S. Application Data

(60) Provisional application No. 60/980,733, filed on Oct. 17, 2007, provisional application No. 61/087,094, filed on Aug. 7, 2008, provisional application No. 61/087,102, filed on Aug. 7, 2008.

(51) Int. Cl.
*C25D 1/00* (2006.01)

(52) U.S. Cl.
USPC .......................................... 205/67; 530/300

(58) Field of Classification Search
USPC .......................................................... 205/67
See application file for complete search history.

(56) References Cited

U.S. PATENT DOCUMENTS

| | | | |
|---|---|---|---|
| 4,304,853 A | 12/1981 | Jozefonvicz et al. | |
| 5,804,400 A * | 9/1998 | Martin et al. | 435/18 |
| 5,834,224 A | 11/1998 | Ruger et al. | |
| 6,013,170 A | 1/2000 | Meade | |
| 6,013,459 A * | 1/2000 | Meade | 435/7.1 |
| 6,248,229 B1 * | 6/2001 | Meade | 205/777.5 |
| 6,348,319 B1 | 2/2002 | Braach-Maksvytis et al. | |
| 6,432,723 B1 | 8/2002 | Plaxco et al. | |
| 6,495,336 B1 | 12/2002 | Ludin et al. | |
| 6,676,816 B2 | 1/2004 | Mao et al. | |
| 6,750,016 B2 | 6/2004 | Mirkin et al. | |
| 6,770,190 B1 | 8/2004 | Milanovski et al. | |
| 6,927,039 B2 | 8/2005 | Gilardi et al. | |
| 6,932,894 B2 | 8/2005 | Mao et al. | |
| 6,991,926 B2 | 1/2006 | Schmid et al. | |
| 7,018,523 B2 | 3/2006 | Meade | |
| 7,267,939 B2 | 9/2007 | Meade | |
| 7,332,369 B2 * | 2/2008 | Veres et al. | 438/99 |
| 7,384,749 B2 | 6/2008 | Kayyem et al. | |
| 7,560,237 B2 | 7/2009 | O'Connor et al. | |
| 7,728,094 B2 * | 6/2010 | Zhou et al. | 528/31 |
| 7,732,140 B2 | 6/2010 | Vandenbark et al. | |
| 7,759,114 B2 | 7/2010 | Martin et al. | |
| 7,803,572 B2 | 9/2010 | Braven et al. | |
| 7,807,835 B2 | 10/2010 | Xie et al. | |
| 2005/0003398 A1 * | 1/2005 | Tao et al. | 435/6 |
| 2005/0123948 A1 | 6/2005 | Claycomb et al. | |
| 2005/0136394 A1 | 6/2005 | Fang et al. | |
| 2006/0003382 A1 | 1/2006 | Eckermann et al. | |
| 2008/0164154 A1 | 7/2008 | Purvis | |
| 2008/0248592 A1 | 10/2008 | Bamdad | |
| 2010/0204554 A1 | 8/2010 | Say et al. | |

FOREIGN PATENT DOCUMENTS

| | | |
|---|---|---|
| EP | 02075339 | 7/2009 |
| WO | WO 97/21431 | 6/1997 |
| WO | WO 98/57158 | 12/1998 |
| WO | WO 98/57159 | 12/1998 |
| WO | 03/019171 | 3/2003 |
| WO | 2004/079848 A2 | 9/2004 |
| WO | 2008/045799 | 4/2008 |
| WO | 2010/142037 | 12/2010 |
| WO | 2011/041586 | 4/2011 |

OTHER PUBLICATIONS

Chen et al. "Preparation and electrocatalytic properties of osmium oxide/hexacyanoruthenate films modified electrodes for catecholamines and sulfur oxoanions", J of Electroanalytical Chemistry, 2006, 589:15-23.*
Li et al. "Nanoscale 1,3,5,7-tetrasubstituted adamantanes and p-substituted tetraphenyl-methanes for AFM applications", Organic Letters, 2002, 4(21):3631-3634.*
Hickman et al. "Molecular self-assemble of two-terminal, voltammetric microsensors with internal references", Science, 1991, 252:688-691.*
Houseman et al. "Maleimide-functionalized self-assembled monolayers for the preparation of peptide and carbohydrate biochips", Langmuir, 2003, 19:1522-1531.*
U.S. Appl. No. 60/980,733, filed Oct. 17, 2007, Georganopoulou.
Ahn-Yoon et al., "Ganglioside-liposome immunoassay for the detection of botulinum toxin," *Anal. Bioanal. Chem.* 378:68-75 (2004).
Aleksey, et al., "Nanoscale 1,3,5,7-Tetrasubstituted Adamantanes and *p*-Substituted Tetraphenyl-methanes for AFM Applications," *Organic Letters* 4(21):3631-3634 (2002).
Alston et al., "Cyclodextrins as Second Sphere Ligands for Transition Metal Complexes—the X-Ray Crystal Structure of [Rh(cod)(NH$_3$)$_2$ α-cyclodextrin][PF$_6$•6H$_2$O**]," *Angew. Chem. Int. Ed. Engl.* 24(9):786-787 (1985).
Amorim et al., "Nuclear Magnetic Resonance Studies of the ProtonationSequence of Some Oxaaza Macrocyclic Compounds," *J. Chem. Soc. Dalton Trans.* 3449-3455 (1990).
Ando, et al., "The effect of second-sphere coordination-II. Adduct formation between [Ru(NH$_3$)5L](PF$_6$)$_n$ (n=2 and 3) and 18-crown-6 ether in solution and the effect on redox behaviour," *Polyhedron* 11(18):2335-2340 (1992).
Ando et al., "Effect of Second-Sphere Coordination. 4. Factors Influencing the Electrochemical Behavior of Ruthenium-Ammine Complexes Cause by Second-Sphere Coordination of Crown Ethers," *Inorg. Chem.* 35:3504-3508 (1996).
Ando et al.,"The Effect of Second-Sphere Coordination. 7. Isolation of 18-Crown-6 Ether Adducts of Ruthenium-Ammine Complexes," *Inorg. Chim. Acta.* 282:247-251 (1998) [bb 5001].
Ando, "Hydrogen bonding of 18-crown-6 ether to ruthenium-ammine complexes at second sphere," *Coordination Chemistry Reviews* 248:185-203 (2004).

(Continued)

*Primary Examiner* — Bin Shen
(74) *Attorney, Agent, or Firm* — Wolf, Greenfield & Sacks, P.C.

(57) ABSTRACT

The invention relates to novel compositions and methods for the detection of analytes using the nuclear reorganization energy, λ, of an electron transfer process.

19 Claims, 36 Drawing Sheets

(56) References Cited

OTHER PUBLICATIONS

Appoh et al., "Electrochemical Investigations into the Binding of Some Nonredox Active Metal Ions to Surface-Bound Glutamic Acid Conjugates," *J. Phys. Chem. C* 111:4235-4245 (2007).
Arion et al., "Potassium-controlled synthesis of heterotopic macrocycles based on isothiosemicarbazide," *Inorg. Chim. Acta* 328:123-133 (2002).
Bottcher et al., "Spectroscopy and Electrochemistry of Cobalt(III) Schiff Base Complexes," *Inorg. Chem.* 36:2498-2504 (1997).
Bryce, et al., "A New Route to 1,4-Disubstituted Cyclohexa-1,3-diene Derivatives: TheSythesis of a Highly Conjugated Bis(benzothiazoline) Derivative," *J. Org. Chem.* 3399-3401 (1984).
Callahan, et al., "Effects of Weak Metal-Metal Interactions in Ligand-Bridged Complexes of Ruthenium. Dimeric Complexes Containing Ruthenium Ions in Different Coordination Environments," *Inorg. Chem.* 14(7):1443-1453 (1975).
Chidsey et al., "Coadsorption of Ferrocene-Terminatd and Unsubstituted Alkanethiols on Gold: Electroactive Self-Assembled Monolayers," *J. Am. chem. Soc.* 112:4301-4306 (1990).
Clements and Rice, "Some 3,9-Dicarboxylic Acids of 2,4,8,10-Tetroxaspirol[5.5]undecane," *J. Org. Chem.* 24:1958-1961 (1959).
Creutz and Taube, "Binuclear Complexes of Ruthenium Ammines," *J. Am. Chem. Soc.* 95:1086-1094 (1973).
Curtis, et al., "Directed, Intramolecular Electron Transfer in Mixed-Valence Dimers," *Inorg. Chem.* 24:385-397 (1985).
Dong, et al., "Perturbation of the electronic structure of the Creutz-Taube ion via asymmetric encapsulation with macrocyclic ether species," *J. Am. Chem. Soc.* 115:4379-4380 (1993).
Eckermann, et al., "Syntheses of Ru—S Clusters with Kinetically Labile Ligands via the Photolysis of [(cymene)$_3$Ru$_3$S$_2$](PF$_6$)$_2$," *Inorg. Chem.* 40:1459-1465 (2001).
Eskelinen, et al., "The synthesis and electrochemical behavior of ruthenium(III) bipyridine complexes: [Ru(dcbpy)Cl$_4$] (dcbpy=4,4'-dicarboxylic acid-2,2'-bipyridine) and [Ru(bpy)Cl$_3$L] (L=CH$_3$OH, PPh$_3$, 4,4'-bpy, CH$_3$CN)," *Journal of Electroanalytical Chemistry* 579:257-265 (2005).
Fu et al., "Terminal Ligand Influence on the Electronic Structure and Intrinsic Redox Properties of the [Fe$_4$S$_4$]$^{2+}$ Cubane Clusters," *Inorg. Chem* 43(12):3647-3655 (2004).
Furholz et al., "The Creutz-Taube Complex Revisited," *J. Am. Chem. Soc.* 106:121-123 (1984).
Gebbink, et al., "Fe$_4$S$_4$ Clusters Functionalized with Molecular Receptor Ligands," *Eur. J. Inor. Chem.* 2087-2099 (2000).
Gerhardt and Weck, "Investigations of Metal-Coordinated Peptides as Supramolecular Synthons," *J. Org. Chem.* 71:6333-6341 (2006).
Gianneschi et al., "Signal Amplification and Detection via a Supramolecular Allosteric Catalyst," *J. Am. Chem. Soc.* 127:1644-1645 (2005).
Grancharov, et al., "Individually addressable recessed gold microelectrode arrays with monolayers of thio-cyclodextrin nanocavities," *Analyst* 130:1351-1357(2005).
Gray and Winkler, "Electron Transfer in Proteins," *Ann. Rev. Biochem.* 65:537 561(1996).
Hallis et al., "Development of Novel Assays for Botulinum Type A and B Neurotoxins Based on Their Endopeptidase Activities," *J. Clin. Microbiol.* 34:1934-1938 (1996).
Heinze and Schlenker., "Main Chain Ferrocenyl Amides from 1-aminoferrocene-1'-carboxylic Acid," *Eur. J. Inorg. Chem.* 2974-2988 (2004).
Heinze and Schlenker, "Anion-Induced Motion in a Ferrocene Diamide," *Eur. J. Inorg. Chem.* 66-71 (2005).
Holleman and Wiberg, "Inorganic Chemistry," *Academic Press* 1616-1627 (2001).
Illingworth, "Phosphofructokinase regulation," School of Biochemistry and Microbiology, University of Leeds, BIOC2120 Lectures 2007 (Aug. 5, 2007), p. 4-6.
Isied and Taube, "Effects of SO$_2$, HSO$_3$, and SO$_3^{2-}$ as Auxiliary Ligands on the Reactivity of Ammineruthenium(II)-Ligand Bonds," *Inorg. Chem.* 13(7):1545-1551 (1974).

Isied and Taube, "Rates of Intermolecular Electron Transfer," *J. Am. Chem. Soc.* 95(24):8198-8200 (1973).
Isied and Kuehn, "Peptide Formation in the Presence of a Metal Ion Protecting Group. Pentaamine Cobalt(III)-Peptide Complexes," *J. Am. Chem. Soc.* 100(21):6752-6754 (1978).
Jeffrey and Rauchfuss, "Metal Complexes of Hemilabile Ligands. Reactivity and Structure of Dichlorobi(o-(diphenylphosphino)anisole)ruthenium(II)," *Inorg. Chem.* 18(10):2658-2666 (1979).
Jwo, et al., "Intramolecular Electron Transfer from Pentacyanoferrate(II) to Pentaamminecobalt(III) Mediated by Various 4,4'-Bipyridines," *J. Am. Chem. Soc.* 101:6189-5197 (1979).
Kanatzidis et al., "A New Iron-Sulphide Cluster Containing the 'Prismane' (Fe6(mu-S6]3+ Core. Synthesis, Structure, and Properties of [Et4N]3[FeS6Cl6]," *J. Chem.Soc., Chem. Commun.* 356-358 (1984).
Karyakin, "Prussian Blue and its analogues: electrochemistry and analytical applications," *Electroanalysis*, 13(10):813-819 (2001).
Kothari and Busch, "Cobalt(III) Complexes of Cysteine and Cysteine Derivatives," *Inorg. Chem.* 8:2276-2280 (1969).
Kerman and Kraatz, "Electrochemical detection of kinase-catalyzed thiophosphorylation using gold nanoparticles," *Chem. Commun.* 5019-5021 (2007).
Kerman et al., "An electrochemical approach for the detection of HIV-1 protease," *Chem. Commun.* 3829-3831 (2007).
Khan et al., "Surface Studies of Aminoferrocene Derivatives on Gold: Electrochemical Sensors for Chemical Warfare Agents," *Anal. Chem.* 79(7):2877-2884 (2007).
Lavallee and Fleischer, "Charge Delocalization in Pentaammineruthenium(II)Complexes. I. Spectral Properties, Basicities, and ChargeDensities by Nuclear Magnetic Resonance Spectroscopy," *J. am. Chem. Soc.* 94(8):2583-2599 (1972).
Liu et al., "Protein modulation of electrochemical signals: application to immunobiosensing," *Chem.Commun.* 3670-3872 (2008).
Louie, et al., "A cobalt complex that selectively disrupts the structure and function of zinc fingers," *Proc. Natl. Acad. Sci. USA* 95: 6663-6668 (1998).
Lowe and Garner, "Transition-metal Complexes of Crown Ether Benzodithiolenes. Part 2. The Effects of Alkali-metal Cation Binding," *J. Chem. Soc. Dalton Trans.* 3333-3340 (1993).
Luo and Isied, "Ruthenium Tetraammine Chemistry of Self-Assembled Monolayers on Gold Surfaces: Substitution and Reactivity at the Monolayer Interface," *Langmuir* 14:3602-3606 (1998).
Mahmoud and Kraatz, "A Bioorganometallic Approach for the Electrochemical Detection of Proteins:A Study on the Interaction of Ferrocene-Peptide Conjugates with Papin in Solution and on Au Surfaces," *Chem. Eur. J.* 13:5885-5895 (2007).
Maeda, et al., "Synthesis of Bis[aminomethyl]crown Ethers," *Synthesis Communications* 185-187 (1983).
Masar, et al., "Fine-Tuning the Weak-Link Approach: Effect of Ligand Electron Density on the Formation of Thodium(I) and Iridium(I) Metallomacrocycles," *Inorg. Chem.* 42(21):6851-6858 (2003).
Moscherosch et al., "Tetranuclear Pentaammineruthenium Complexes Bridged by π-Conjugated Tetracyano Ligands Related to TCNE; Syntheses and Spectroscopy of Different Oxidation States," *Inorg. Chem.* 34:4326-4335 (1995).
Moutet, et al., "Heterodinucleating macrocyclic compounds designed for electrochemical recognition," *Electrochimica Acta* 46:2733-2740 (2001).
Neyhart et al., "Solvent-Induced Electron Transfer and Delocalization in Mixed-Valence Complexes. Electrochemistry," *J. Am. Chem. Soc.* 118:3724-29 (1996).
Nguyen et al., "An Affinity-Based Method for the Purification of Fluorescently-Labeled Biomolecues," *Bioconjugate Chem.* 17:869-872 (2006).
Orlowski, et al., "Electrodeposition of ferrocenoyl peptide disulfides," *Chem. Commun.*, 1330-1332 (2005).
Orlowski, et al., "Reorganization Energies of Ferrocene-Peptide Monolayers," *Langmuir* 23:12765-12770 (2007).
Peruski et al., "Rapid and sensitive detection of biological warfare agents using time-resolved fluorescence assays," *J. Immunol Methods* 263:35-41 (2002).

(56) References Cited

OTHER PUBLICATIONS

Plumb and Kratz, "Interaction of a Ferrocenoyl-Modified Peptide with Papin:Toward Protein-Sensitive Electrochemical Probes," *Bioconjugate Chem.* 14:601-606 (2003).
RAWLS, "Optimistic About Antisense," *C&EN* 35-39 (1997).
Ricci and Palleschi, "Sensor and biosensor preparation, optimisation and applications of Prussian Blue modified electrodes," *Biosensors & Bioelectronics* 21(3):389-407 (2005).
Richardson et al., Preparation and Properties of Mixed-Valence (mu-Dinitrogen)bis(pentaamine) Complexes of Osmium and Ruthenium,RAWLS, C & E News p. 35, Jun. 2, 1997 *Inorg. Chem.* 21:3136-3140 (1982).
Richardson and Taube, "Electronic Interactions in Mixed-Valence Molecules as Mediated by Organic Bridging Groups," *J. Am. Chem. Soc.* 105:40-51 (1983) (bb 5001).
Rosa and Coucouvanis, "Crown-Ether-Functionalized Nickel Salicylaldimine Complexes. Structural Characterization of Their Potassium, Cesium, and Hexylammonium Derivatives andTheir Use in the Transport of Amino Acids," *Inorg. Chem.* 37:2328-2329 (1998).
Schiavo et al., "Identification of the Nerve Terminal Targets of Botulinum Neurotoxin Serotypes A,D, and E," *JBC* 268(32):23784-23787 (1993).
Schiavo et al., "Botulinum neurotoxins seotypes A and E cleave SNAP-25 at distance COOH-terminal peptide bonds," *FEBS Letters* 335(1):99-103 (1993).
Schmidt et al., "Fluorigenic Substrates for the Protease Activities of Botulinum Neuroxtoxins, Serotypes A, B, and F," *Appl. Environ. Microbiol.* 69(1):297-303 (2003).
Shults and Imperiali, "Versatile Fluorescence Probes of Protein Kinase Activity," *J. Am. Chem. Soc.* 125:14248-14249 (2003).
Scott and Nolan, "Stabilization of Organometallic Species Achieved by the Use of N-Heterocyclic Carbene (NHC) Ligands," *Eur. J. Inorg. Chem* 1815:1828 (2005).
Seidel, et al., "Coordination chemistry of N-Alkylbenzamide-2,3-dithiolates as an Approach to Poly(dithiolate) Ligands: 1,4-Bis[(2,3-dimercaptobenzamido)methylibenzene and Its Chelate Complex with the ($C_5H_5$)Ti Fragment," *Inorg. Chem.* 37:6587-6596 (1998).
Shone, et al., "Proteolytic cleavage of synthetic fragments of vesicle-associated membgrane protein, isoform-2 by botulinum type B neurotoxin," *Eur. J. Biochem* 217:965-972 (1993).
Silverman et al., "Multivalent avimer proteins evolved by exon shuffling of a family of human receptor domains," *Nature Biotechnology* 23:1556-1561 (2005).
Sizova, et al., "Substituents effect on the electronic structure, spectra and photochemistry of $[Ru(NH_3)_5(PY-X)]^{2+}$ complexes," *Inorg. Chim. Acta* 357:354-360 (2004).
Song et al., "Electrochemical detection of kinase-catalyzed phosphorylation using ferrocene-conjugated ATP;" *Chem. Commun.* 502-504 (2008).
Sprinzl et al., "Enzymatic Incorporation of ATP and CTP Analogues into the 3' End of tRNA," Eur. J. Biochem. 81:579 (1977).
Stodt et al., "Preparation, Reactivity and Peptide Labelling Properties of ($\eta^6$-Arene)ruthenium(II) Complexes with Pendant Carboxylate Groups," *Euro. J. Inorg. Chem.* 1873-1882 (2003).
Sutton and Taube, Metal to Metal Interactions in Weakly Coupled Mixed-Valence Complexes Based on Ruthenium Ammines, *Inorg. Chem.* 20(10):3125-3134 (1981).
Sutton et al., "Determination of the Comporportionation Constant for a Weakly Coupled Mixed-Valence System by Titration of the Intervalence Treansfer Band: μ-4,4'-Bipyridyl)-bis(pentaam-mineruthenium)(5+)," *Inorg. Chem.* 18(4):1017-1021 (1979).
Syamal et al., "Syntheses and characterization of a chelatingresin containing ONNO donor quadridentate Schiff base and its coordination complexes with copper(II), nickel(II), cobalt(II), iron(III), zinc(II), cadmium(II), molybdenum(VI) and uranium(VI)[1,2]," *Reactive and Functional Polymers* 39:27-35 (1999).
Therrien and Suss-Fink, "New mono and dinuclear arene ruthenium chloro complexes containing ester substituents," *Inorganica Chimica Acta* 359:4350-4354 (2006).

Tom et al., Mixed Valence Complexes of Ruthenium Ammines with 4,4'-Bipyridine as Bridging Ligand, *J. Am. Chem. Soc.* 96(25):7827-7829 (1974).
Volkers, et al., "Coordination Chemistry of 3-Mercapto-2-(Mercaptomethyl)propanoic Acid (Dihydroasparagusic Acid) with Iron and Nickel," *Eur. J. Inorg. Chem.* 4793-4799 (2006).
Wang, et al., "tmtacn,tacn, and Triammine Complexes of ($\eta^6$-arene)Ox[II]: Syntheses, Characterizations, and Photosubstitution Reactions (tmtacn=1,4,7-Trimethyl-1,4,7-triazacyclononane; tacn=1,4,7-Triazacyclononane)," *Inorg. Chem.* 40:593-600 (2001).
Wei, et al., "Diverse Redox-Active Molecules Bearing Identical Thiol-Terminated ripodal Tethers for Studies of Molecular Information Storage," *J. Org. Chem.* 69:1461-1469 (2004).
Adjemian, Jogelyne, et al., "Cleavage-Sensing Redox Peptide Monolayers for the Rapid Measurement of the Proteolytic Activity of Trypsin and a-Thrombin Enzymes," Langumuir Article, Jan. 27, 2010, pp. 1-10.
Chin, Curtis D., et al., "Microfluidics-Based Diagnostics of Infectious Diseases in the Developing World," Nature Medicine, Technical Reports, Jul. 31, 2011, pp. 1-6.
Gaster, Richard S., et al., "nanoLAB: An Ultraportable, Handheld Diagnostic Laboratory for Global Health," Lab on a Chip, Dynamic Article Links, Jan. 25, 2011, pp. 1-7.
Houseman, Benjamin T., et al., "Peptide Chips for the Quantitative Evaluation of Protein Kinase Activity," Nature Biotechnology, Research Article, Mar. 2002, vol. 20, pp. 270-274.
Kerman, Kagan, et al., "Peptide Biosensors for the Electrochemical Measurement of Protein Kinase Activity," Anal. Chem., 2008, vol. 80, pp. 9395-9401.
Kerman, Kagan, et al., "Electrochemical Detection of Protein Tyrosine Kinase-Catalysed Phosphorylation Using Gold Nanoparticles," Biosensors and Bioelectronics, 2009, vol. 24, pp. 1484-1489.
Kim, S.D., et al., "Gold-Film Array-Electrode for Electrochemical ELISA," Sensors and Actuators B, 2005, pp. 463-469.
Labib, Mahmoud, et al., "A Bioorganometallic Approach for Rapid Electrochemical Analysis of Human Immunodeficiency Virus Type-1 Reverse Transcriptase in Serum," Elsevier, Article in Press, Elecrochimica Acta, available online Mar. 22, 2011, pp. 1-7.
Leinonen, J., et al., "Development of Novel Peptide Ligands Modulating the Enzyme Activity of Prostatespecific Antigen," Scand. J. Clin. Lab. Invest., 2000, pp. 59-64.
Li, Peng, et al., "Develoopment of an Ultrafast Quantitative Heterogeneous Immunoassay on Prefunctionalized Poly (Dimethylsiloxane), Microfluidic Chips for the Next-Generation Immunosensors," Microfluidics and Nanofluidics, vol. 7, No. 4, Mar. 11, 2009.
Martic, Sanela, et al., "Probing the Role of the Linker in Ferrocene-ATP Conjugates: Monitoring Protein Kinase Catalyzed Phosphorylations Electrochemically," Chemistry A European Journal, 2011, vol. 17, pp. 6744-6752.
Martic, Sanela, et al., "Use of 5-y-Ferrocenyl Adenosine Triphosphate (Fc-ATP) Bioconjugates Having Poly (ethylene glycol) Spacers in Kinase-Catalyzed Phosphorylations," Bioconjugate Chemistry, 2011, pp. 1-10.
Martic, Sanela, et al., "Enzymatically Modified Peptide Surfaces: Towards General Electrochemical Sensor Platform for Protein Kinase Catalyzed Phosphorylations," Analyst, 2011, 136, pp. 107-112.
Nagy, Geza, et al., "Screen-Printed Amperometric Microcell for Proline Iminopeptidase Enzyme Activity Assay," Biosensors & Bioelectronics, 2000, vol. 15, pp. 265-272.
Vukmirovic-Popovic, Snezana, et al., "Presence and Enzymatic Activity of Prostate-Specific Antigen in Archival Prostate Cancer Samples," Oncology Reports, 2008, vol. 20, pp. 897-903.
Zhou, Ya-Min, et al., "An Amperometric Immunosensor Based on an Electrochemically Pretreated Carbon-Paraffin Electrode for Complement III (C3) Assay," Biosensors and Bioelectronics, 2008, vol. 18, pp. 473-481.
Liu, Guodong, et al., "Electrochemical Proteolytic Beacon for Detection of Matrix Metalloroteinase Activities," Journal of the American Chemical Society, 2006, vol. 128, pp. 12382-12383.

(56) References Cited

OTHER PUBLICATIONS

Spinke, J., et al., "Molecular Recognition at selfassembled monolayers: Optimization of surface functionalization," The Journal of Chemical Physics, vol. 99, No. 9, Nov. 1993, pp. 7012-7018.

Spinke, J., et al., "Molecular Recognition at self-assembled monolayers: The construction of multicomponent multilayers," Langmuir, 1993, pp. 1821-1825.

* cited by examiner

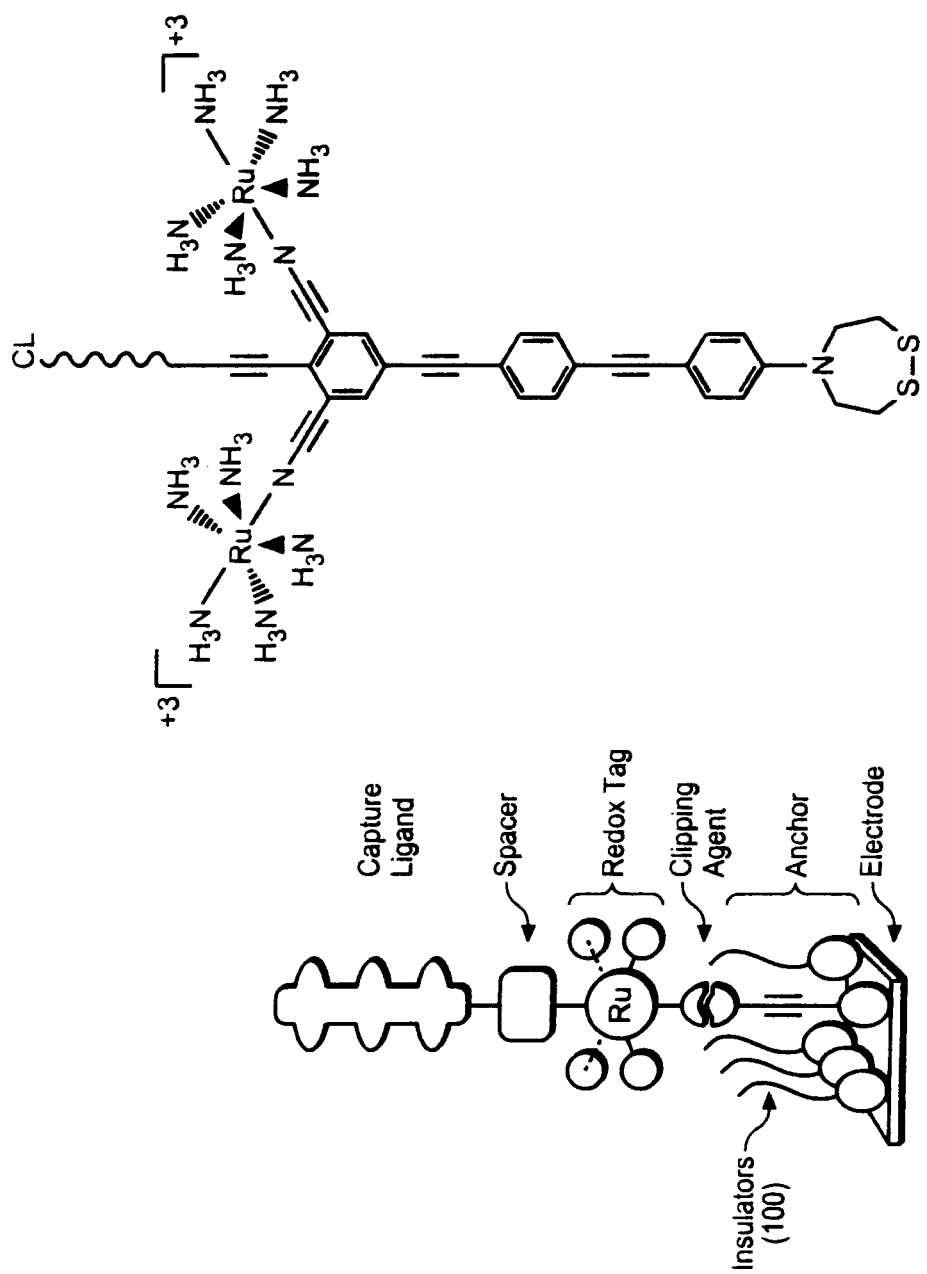
FIG. 1C
FIG. 1B
FIG. 1A

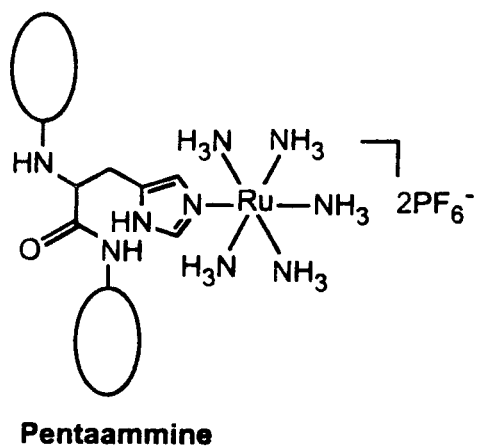
Pentaammine
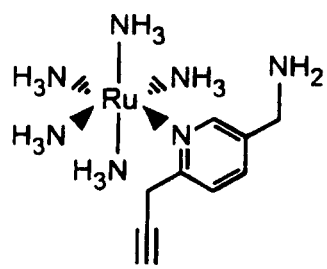
Monodentate
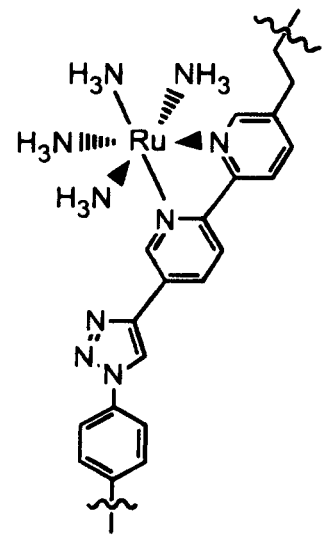
Bidentate
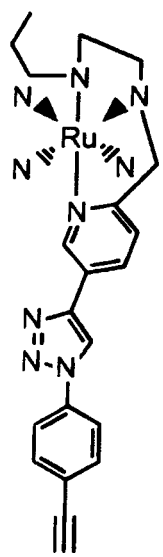
Tridentate
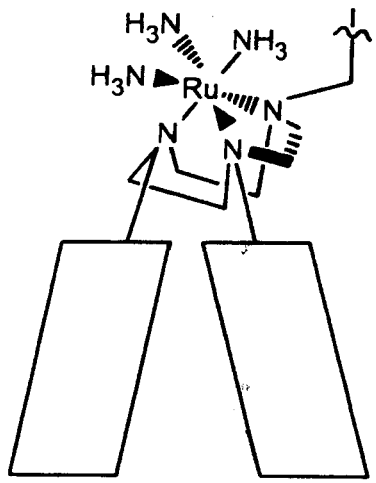
Multidentate
FIG. 5A

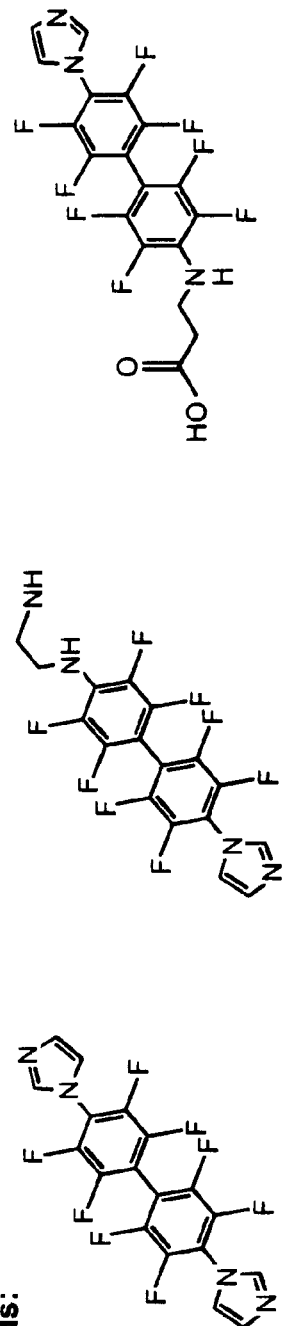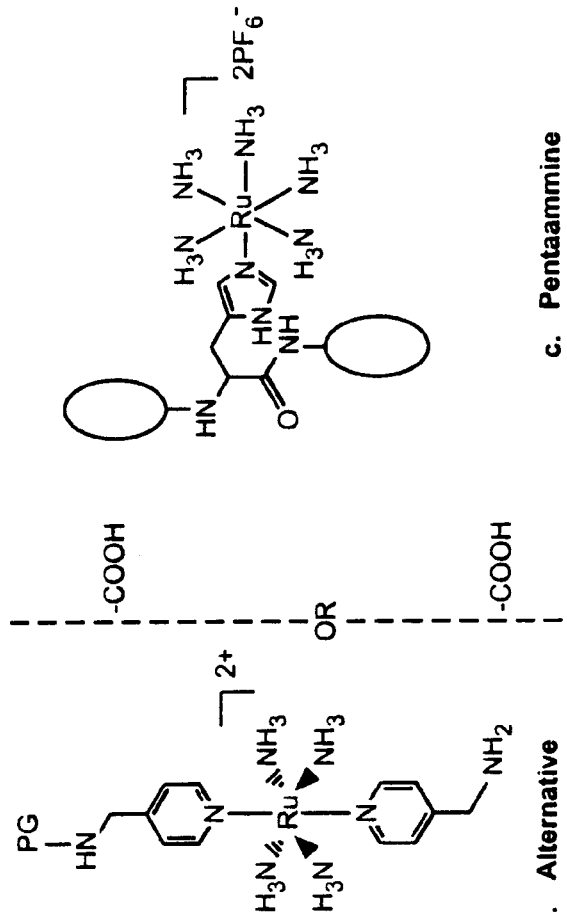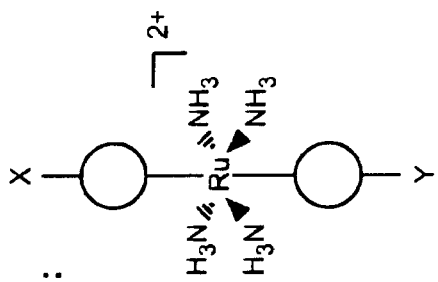
FIG. 9A

Anchors:

a. Coordination  b. Amine  c. Carboxylic Acid

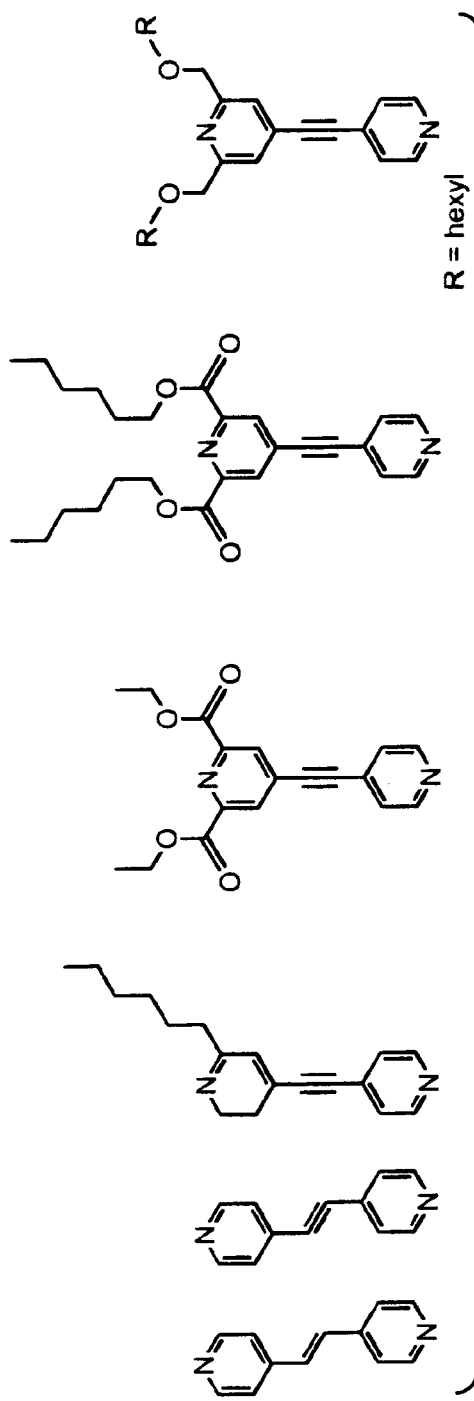
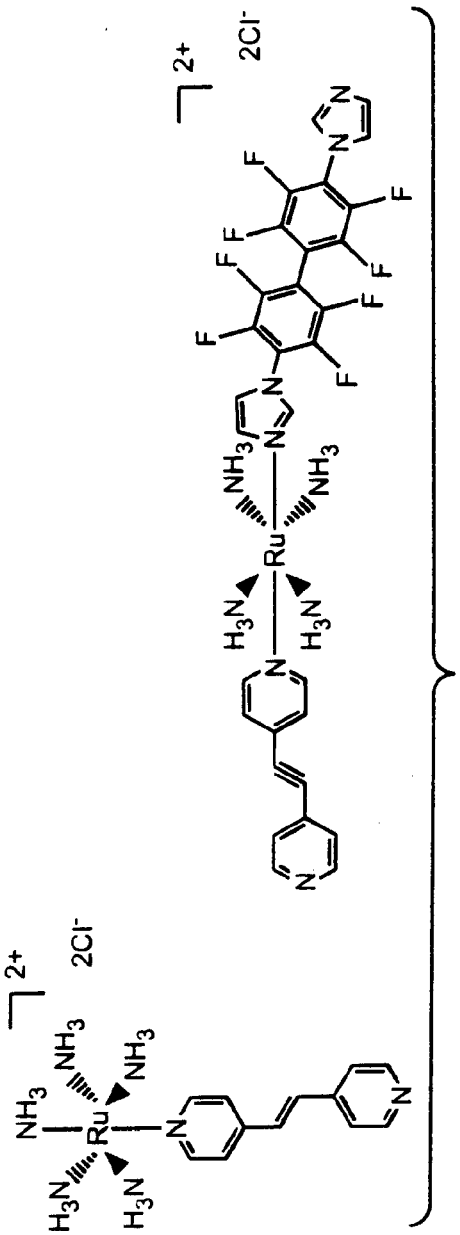
FIG. 10A
FIG. 10B

NH2 Reactive Maleimide

C3-Mal-NHS

NH2 Reactive Maleimide

MBA-Mal-NHS

COOH Reactive Maleimides

C2-Mal

COOH Reactive Maleimides

C6-Mal

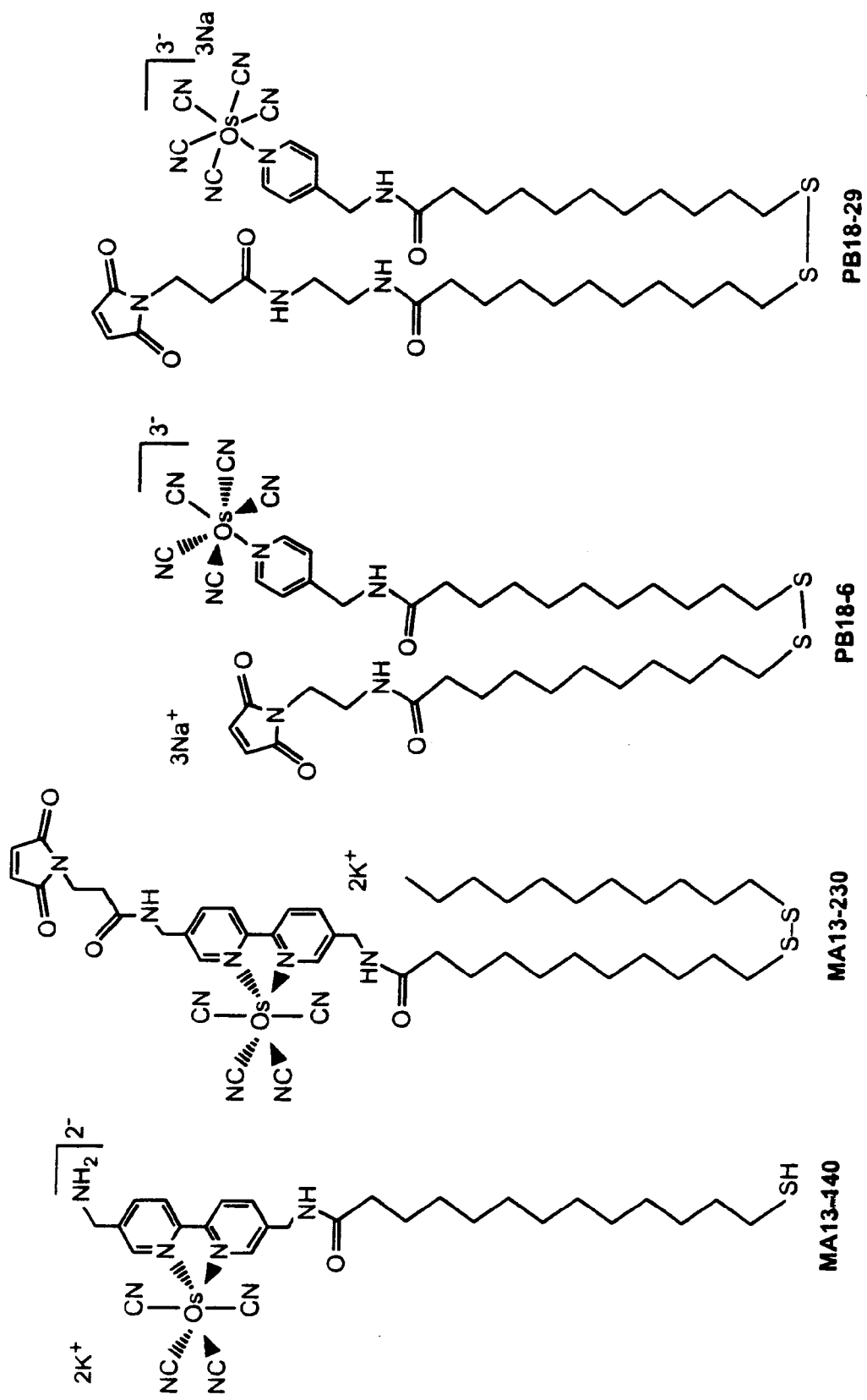
FIG. 17A  MA13-140
FIG. 17B  MA13-230
FIG. 17C  PB18-6
FIG. 17D  PB18-29

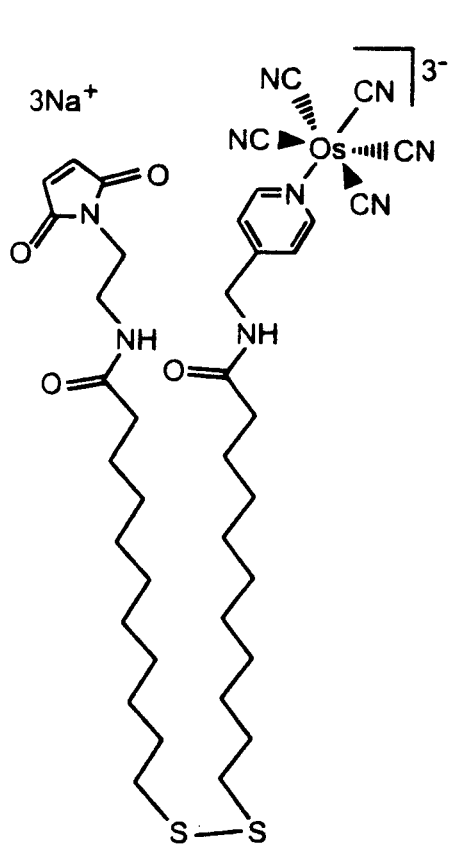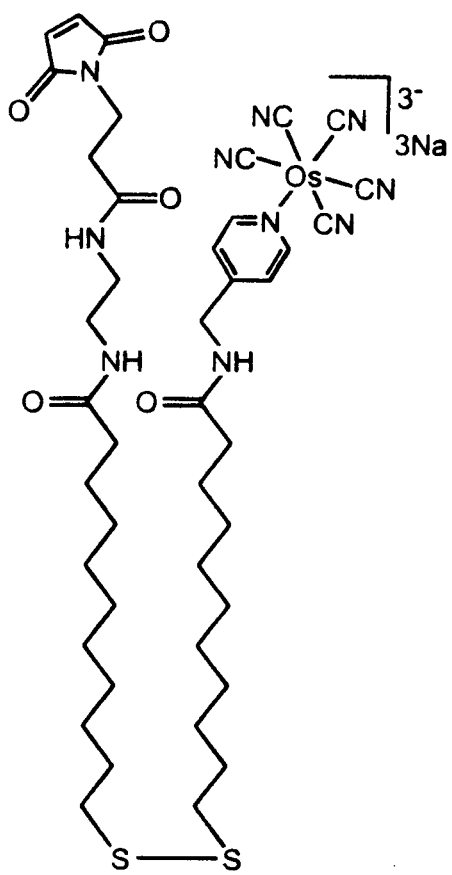
PB18-6　　　　　　　　　　　PB18-29
*FIG. 18A*　　　　　　　　*FIG. 18B*

Capture ligands

- Carboxylic acid reactant capture ligand

1. Anthrax peptide: FMOC-NH-ATYPLPIR-COOH (SEQ ID NO: 1)
  2. SEB peptide: FMOC-NH-YYWLHH-Cys-COOH (SEQ ID NO: 2)

- Maleimide reactive capture ligands

1. E. coli peptide: Ac NH-LHIHRTLSIQGGGGS-Cys-COO (SEQ ID NO: 3)
  2. PSA peptide: Ac NH-HSSKLQ-Cys-COOH (SEQ ID NO: 4)
  3. SEB peptide: NH2-YYWLHH-Cys-COOH (SEQ ID NO: 5)
  4. Anthrax peptide: NH2-ATYPLPIR-COOH (SEQ ID NO: 6)
  5. Thiolated biotin

Figure 24

Different Ferrocenes

Amide

PB18-42

Different Ferrocenes

Amide

PB18-44

Different Ferrocenes
Ketone
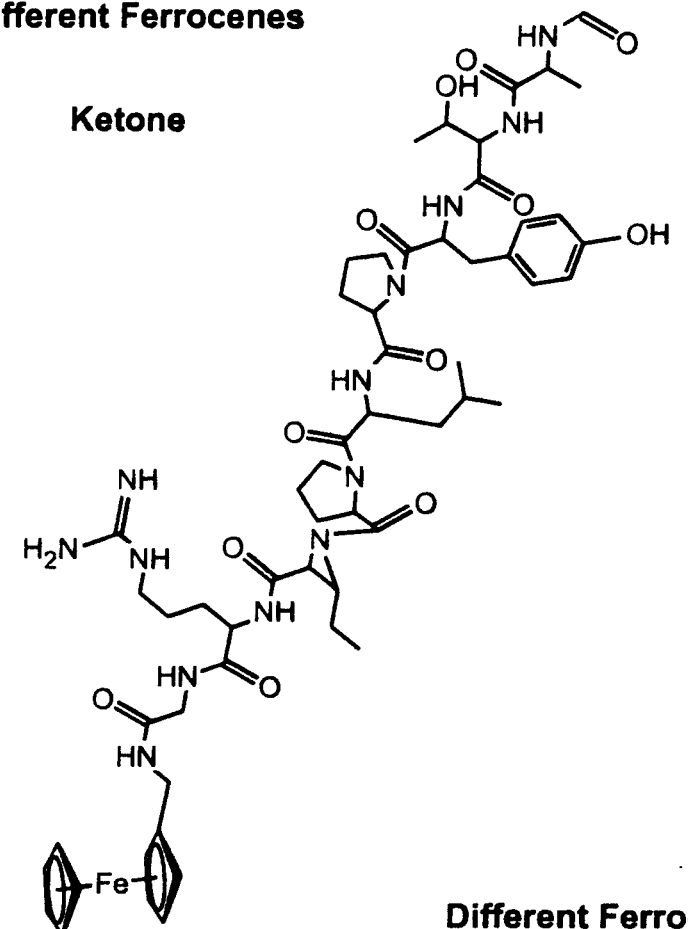
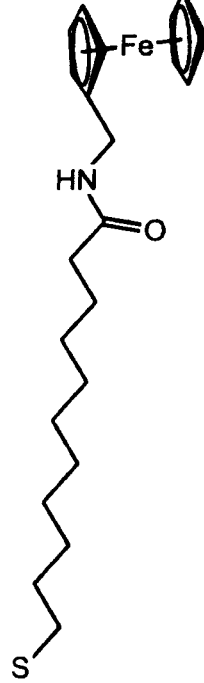
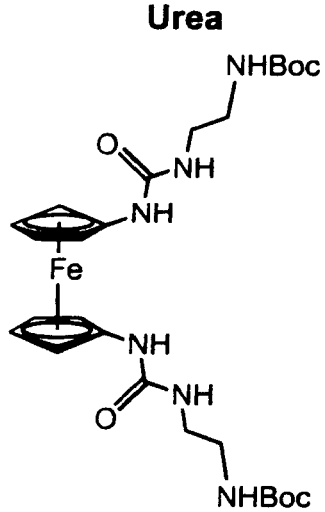
Different Ferrocenes
Urea
PB11-169
PB18-69
*FIG. 25C*
*FIG. 25D*

Universal Ferrocene EAM Precursors

PB11-212

Universal Ferrocene EAM Precursors

PB11-225

Universal Ferrocene EAM Precursors

PB18-42

Universal Ferrocene EAM

PB18-44

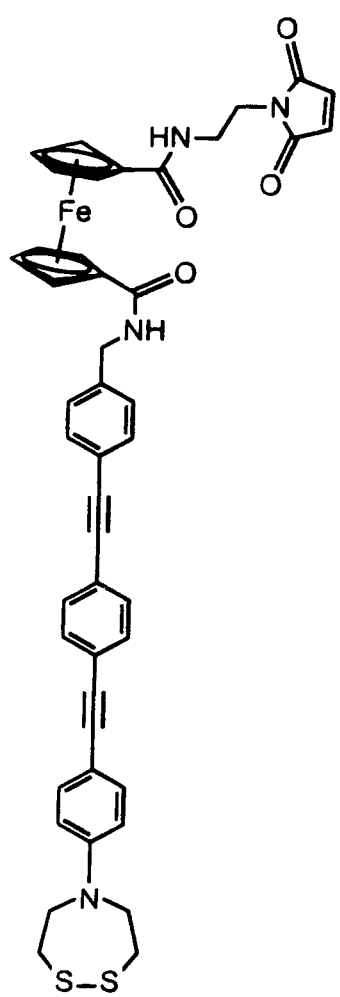 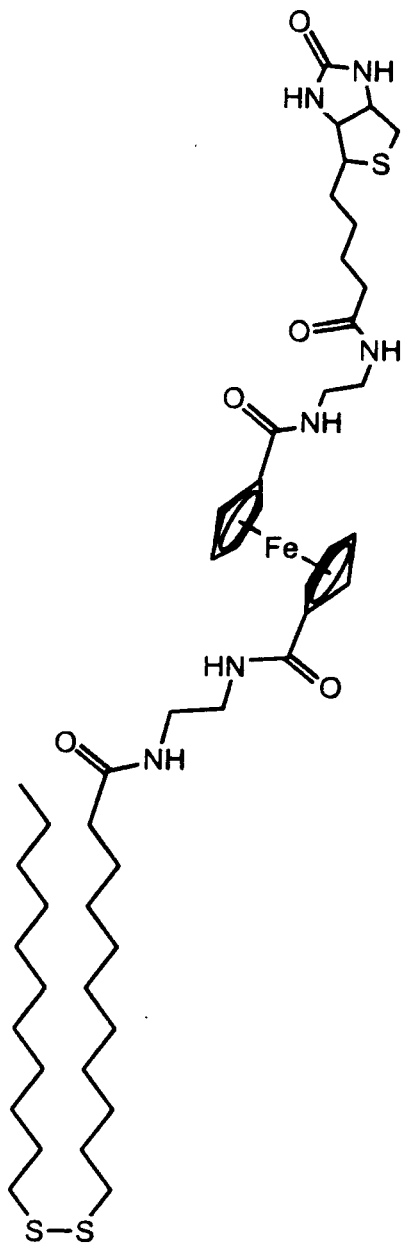
*FIG. 27A*  *FIG. 27B*

CHEMISTRY USED IN BIOSENSORS

CROSS REFERENCE TO RELATED APPLICATIONS

This application claims the benefit of, and priority to, U.S. Provisional Patent Application Ser. Nos. 60/980,733, filed on Oct. 17, 2007, and 61/087,094 and 61/087,102, filed on Aug. 7, 2008, the entire disclosures of which are hereby incorporated by reference in their entireties.

FIELD OF THE INVENTION

The invention relates to novel compositions and methods for the detection of analytes using change in $E^0$ of target analytes.

BACKGROUND OF THE INVENTION

Electron transfer reactions are crucial steps in a wide variety of biological transformations ranging from photosynthesis or aerobic respiration. Studies of electron transfer reactions in both chemical and biological systems have led to the development of a large body of knowledge and a strong theoretical base, which describes the rate of electron transfer in terms of a small number of parameters.

Electronic tunneling in proteins and other biological molecules occurs in reactions where the electronic interaction of the redox centers is relatively weak. Semiclassical theory reaction predicts that the reaction rate for electron transfer depends on the driving force ($-\Delta G^\circ$), a nuclear reorganization parameter ($\lambda$), and the electronic-coupling strength between the reactants and products at the transition state ($H_{AB}$), according to the following equation:

$$k_{ET} = (4\pi^3/h^2 \lambda k_B T)^{1/2} (H_{AB})^2 \exp[(-\Delta G^\circ + \lambda)2/\lambda k_B T]$$

The nuclear reorganization energy, $\lambda$, in the equation above is defined as the energy of the reactants at the equilibrium nuclear configuration of the products. For electron transfer reactions in polar solvents, the dominant contribution to $\lambda$ arises from the reorientation of solvent molecules in response to the change in charge distribution of the reactants. The second component of $\lambda$ comes from the changes in bond lengths and angles due to changes in the oxidation state of the donors and acceptors.

Previous work describes using change in reorganization energy, $\lambda$, as the basis of novel sensors. See for example, U.S. Pat. Nos. 6,013,459, 6,013,170, 6,248,229, and 7,267,939, all herein incorporated by reference in their entirety. The methods generally comprise binding an analyte to or near a redox active complex. The redox active complex comprises at least one electroactive molecule and a capture ligand which will bind the target analyte, and the complex is bound to an electrode. Upon analyte binding, the reorganization energy of the redox active molecule is altered, thus changing the $E^0$, and allowing detection.

It is an object of the present invention to provide composition and methods for the detection of target analytes using alterations in the solvent reorganization energy, such as utilizing cyano ligands with the transition metals of the biosensor, corresponding to changes in the $E^0$ of redox active molecules.

SUMMARY OF THE INVENTION

The present invention provides methods and compositions relating to biosensors for use in the detection of target analytes.

In one aspect, the invention provides compositions comprising a solid support (sometimes referred to herein as a "substrate") comprising an electrode comprising a covalently attached electroactive complex (EAM) with a particular $E^0$. The substrates can optionally comprise an array of electrodes. The electrode(s) each comprise an EAM, that optionally can be part of a ReAMC. Suitable transition metals include iron, ruthenium and osmium, as well as others outlined herein. In some embodiments, the EAMs comprise at least one cyano ligand, with 2, 3, 4 and 5 also finding use in the invention. The EAMs (as well as the ReAMCs and diluent SAM forming species) can be linked to the electrodes using attachment linkers, including alkyl groups (including substituted alkyl groups).

In a further aspect, the electrodes optionally comprise self assembled monolayer (SAM) species.

In an additional aspect, the EAM/ReAMCs of the invention are attached to the electrode using an anchor ligand, which can be "unipodal" or "multipodal", for example including the use of bipodal attachments such as two sulfur atoms or cyclic disulfide anchor groups.

In a further aspect, the EAM is part of a redox active capture complex (REAMC) comprising said EAM and a capture ligand. In one aspect, the capture ligand provides a coordination atom for the transition metal. In additional aspects, the capture ligand is separate from the EAM, such that the electrode comprises a first species comprising the EAM and a second species comprising a capture ligand.

In one aspect, the capture ligand is a protein, including peptides, or a carbohydrate.

In an additional aspect, the invention provides methods of detecting a target analytes comprising contacting a sample with a composition comprising an electrode as outlined herein. The binding of the target analyte to the capture ligand alters the $E^0$ of the EAM, e.g. creating a second $E^0$, which is measured to determine the presence or absence of the target analyte.

In a further aspect, the invention provides methods of making a biosensor comprising providing an electrode comprising a first species (usually a SAM forming species) comprising a first functional group. The electrode is contacted with a biomolecule (which will become the capture ligand) comprising a second functional group to form a covalent bond between the first species and the biomolecule. The electrode also comprises an electroactive complex (EAM), to form the biochips of the invention. In some aspects the functional groups on each molecule are selected from the group consisting of moieties comprising a maleimide, imidoester, N-hydroxysuccinimidyl, alkyl halide, aryl halide, alpha-haloacyl and pryidyl disulfide and cysteines (e.g. the first functional group comprises a maleimide and the biomolecule is a protein (e.g. peptide) comprising a cysteine amino acid.

In an additional aspect, the invention comprises compounds having the formula:

wherein said anchor comprises a cyclic-disulfide group,
EAM is an electroactive moiety comprises a solvent accessible redox compound,
CL is a capture ligand,
Spacer 1 is a SAM forming species, and
n=0 or 1.

In an additional aspect, the invention comprises compounds having the formula:

 (I), wherein EAM is an electroactive moiety comprising a transition metal and at least one charge-neutralizing ligand. The charge neutralizing ligand can be selected from the group consisting of: dithiocarbamate, benzenedithiolate, a Schiff base, EDTA, DTPA, carboxylate, amine, thiolate, phosphine, imidazole, pyridine, bipyridine, terpyridine, tacn, salen, acacen, Cp, pincer, scorpionates and pentaammine.

BRIEF DESCRIPTION OF THE DRAWINGS

FIGS. 1A-1C depicts several compounds of the invention. FIG. 1A shows a compound comprising a capture ligand at one end that is linked to a redox here (here is shown to contain a Ruthenium example) through a spacer. The compound also comprises an anchor, through which the compound is attached to the surface of an electrode. Also shown are insulators (110) that are attached to the surface of the electrode as well. FIGS. 1B and 1C depicts a compound comprises multiple metals. The geometries such as the one shown, where CL is "capture ligand", will attract a single protein and have it interact with two metal centers simultaneously giving a larger change in potential.

FIG. 5A depicts new architectures for Ru—N based complexes.

FIGS. 10A and 10B depict some exemplary compounds.

FIGS. 12 and 13 depict several exemplary schematics of suitable geometries of the present invention.

FIGS. 17A, B, C and D depict some exemplary compounds. Similar compounds can be constructed with different anchors, such as disulfide cyclic anchor groups, for example, or different spacers.

FIGS. 18A and B depict some exemplary compounds. Similar compounds can be constructed with different anchors, such as disulfide cyclic anchor groups, for example, or different spacers.

FIG. 24 depict capture ligands.

FIGS. 27 A and B depict some exemplary compounds. Similar compounds can be constructed with different anchors, such as disulfide cyclic anchor groups, for example, or different spacers.

DETAILED DESCRIPTION OF THE INVENTION

Figure 2:
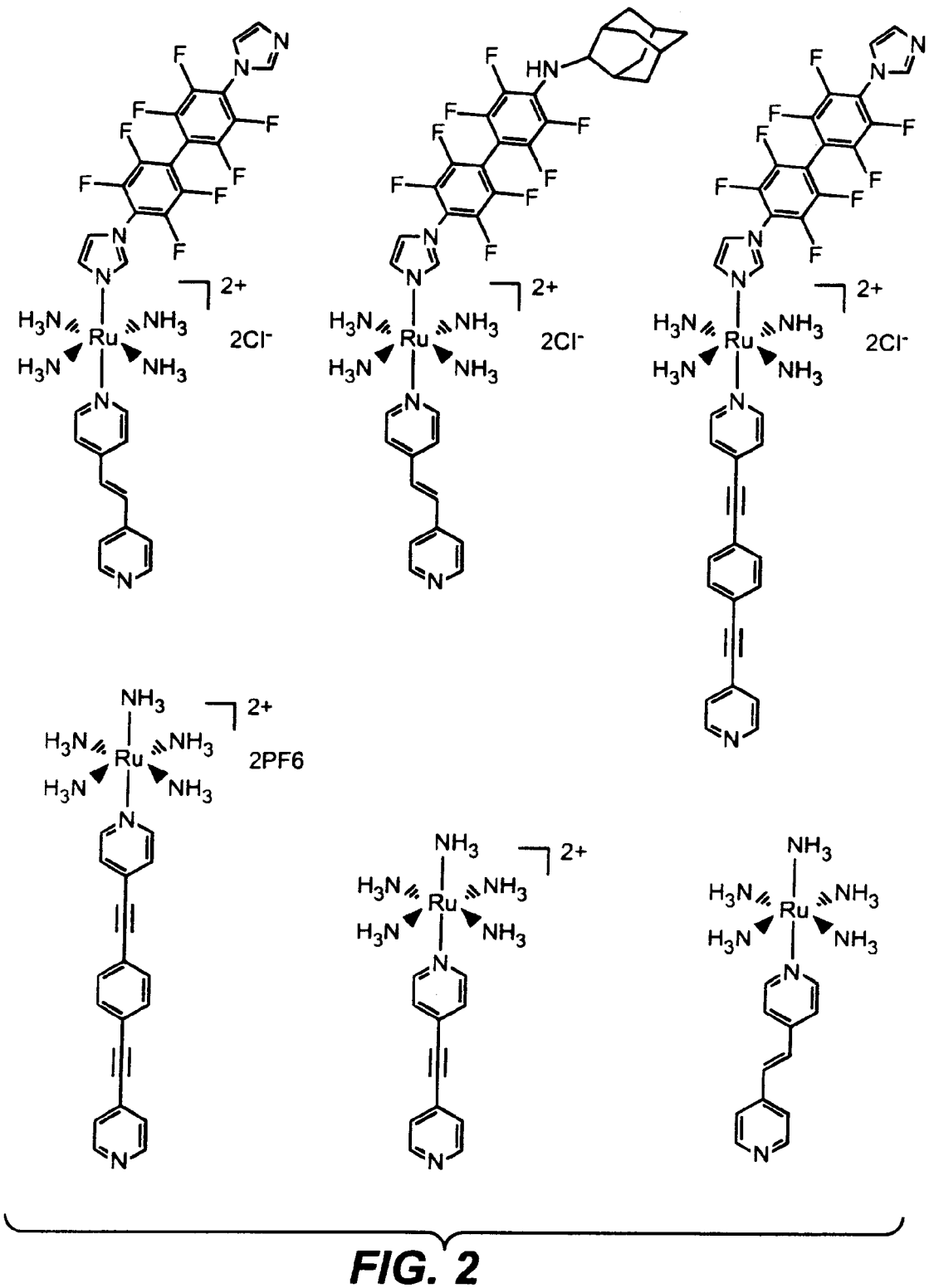
FIG. 2 depicts [BIM-Ru(NH$_3$)$_4$L]2+complexes with BPAI anchors and [Ru(NH$_3$)$_5$L]2+complexes with BPA anchors.

The present invention is directed to improvements in electrochemical biosensors that rely on changes in the reorganization energy, $\lambda$, upon interaction of the target analyte and the biosensor, as evidenced by alterations in the observed $E^0$. As shown previously, biosensors have been described that rely on changes in reorganization energy. The present invention has shown surprising improvements such as utilizing cyano ligands for the transition metal of the electroactive moieties (EAMs). The cyano ligands provide a surprising increase in the change of the $E^0$; e.g. the delta in the $E^0$ is higher than seen for other charged ligands.

I. Overview of Reorganization Energy

The present invention provides methods and compositions for the detection of target analytes using changes in the reorganization energy of redox active molecules upon binding of the analytes, to facilitate or hinder electron transfer between the redox active molecule and an electrode. This invention is based on the fact that when a redox active molecule, such as a transition metal ion, is either oxidized (losing an electron) or reduced (gaining an electron), changes occur in the molecular structure as well as in its immediate solvent environment. These changes in the molecules structure (bond lengths and angles) and in the organization of the solvent molecules surrounding the molecule serve to stabilize the new oxidation state energetically. The sum of these changes constitute the reorganization energy, $\lambda$, of a redox reaction. The intramolecular changes are termed the inner-sphere reorganization energy, $\lambda_i$, and the changes in the solvent and environment are termed the outer-sphere or solvent reorganization energy, $\lambda_o$.

For the purposes of this invention, the primary focus is on changes in the solvent reorganization energy although changes in the inner-sphere reorganization will also be considered in several embodiments of the invention. It is the intent of this invention to capitalize on changes in reorganization energy of a redox reaction when an electroactive molecule (EAM) is attached to a capture ligand (CL) which can selectively bind to an analyte of interest (e.g., proteint or bacteria). Binding of the EAM-CL to the analyte results in a change in the solvent environment of the EAM so that the reorganization energy for a redox reaction involving the EAM is changed. For the case where the redox reaction involves electron transfer between an electrode and the EAM, the standard potential, $E^0$, is changed. Thus, a change in $E^0$ for an EAM-CL complex is an indication that it is bound to the analyte. It is the intent of this invention to detect the change in $E^0$ as an indicator of binding and, consequently, the presence or absence of the analyte.

In conventional methodologies for analyte detection using electron transfer usually employ the EAM as a label or tag attached to one member of a binding pair (e.g., antibody and antigen). In these methods, EAM's are chosen in which the outer sphere solvent effect is minimal, by using electroactive molecules that have minimal solvent reorganization upon oxidation or reduction. Such EAMs generally comprise large hydrophobic ligands which have little interaction with water. Thus, the ligands for the transition metal ions traditionally used are non-polar and are generally hydrophobic, frequently containing organic rings (e.g., bipyridyl and terpyridyl). Such EAMs are chosen because conventionally because the magnitude of the total electron transfer reaction is measured (current) at a predetermined electrode potential.

Without being bound by theory, it is expected that the redox molecules best suited for this invention will be those whose redox reaction has a large solvent organization energy in aqueous environments. Solvent reorganization to stabilize an increase or decrease in charge can be attributed to several phenomena. In polar solvents such as water, the charge on a redox molecule is stabilized by orientation of the polar solvent molecules in the environment near the redox molecule. Since polar molecules have slight charge variation on different atoms of the molecule, their orientation around the redox molecule can help to stabilize it. Further, some ligands, such as $CN^-$, themselves are polar and have partial charges on atoms. These polar ligands can themselves induce an orientation of surrounding solvent molecules. Stabilization (or destabilization) of charged redox molecules can also occur by hydrogen bonding of solvent and/or other molecules to the ligands of the transition metal in the redox molecule. Solvent molecules, as well as other molecules in the solvent surrounding a redox molecules can be characterized and compared based on their donor number or acceptor number (Neyhart et al., J. Am. Chem. Soc 118 (1996) 3724-29, incorporated herein by reference). The use of a particular solvent or a particular additive to a solvent of a molecule having a preferred donor or acceptor number would affect the solvent reorganization energy of a redox reaction. Further, a change in the charge of a redox molecule is stabilized by charged ion in the solvent. Thus, changes in solvent reorganization change upon analyte binding can be maximized by the proper choice of an electrolyte, considering the charge on the ions, the concentration of the ions, the size of the ions, and the hydrophobicity of the ions.

Without being bound by theory, it is preferred to maximize the stabilization of the redox molecule (i.e., maximize its solvent reorganization energy) in the solvent system of choice in order that the phenomena which stabilize the redox molecule are disrupted upon binding of the redox molecule/capture ligand complex, EAM-CL to the analyte. Under such conditions, one would expect that the change in reorganization energy, evidenced by a change in $E^0$, would be optimum. It is expected that the binding of the CL to the analyte will "force" the EAM into an environment on the surface or in a cleft or pocket of the analyte (e.g., a protein) which will be less favorable to the optimal organization of the solvent environment. In one embodiment it is expected that binding would cause a shedding of water molecules near the EAM because of steric constraints.

It should be noted, and not being bound by theory, that whether the solvent reorganization energy increases or decreases upon binding (and whether $E^0$ nives to more positive or to more negative potentials is dependent upon the particular charge of the EAM. If the EAM redox reaction being monitored results in an increased charge of the EAM, such as $EAM^{2+}$ oxidation to $EAM^{3+}$, then the bound environment of the EAM-CL would be less stabilized by reorganization than the unbound EAM-CL. Hence, one would expect the $E^0$ to move to more positive potentials. Alternatively, if the EAM redox reaction being monitored results in a decreased charge of the EAM, such as $EAM^{2-}$ oxidation to $EAM^-$, then the unbound EAM-CL would be less stabilized by reorganization than the bound EAM-CL. Hence, one would expect the $E^0$ to move to less positive potentials.

Without being bound by theory, there are two general mechanisms which may be exploited in the present invention. The first relates to inner sphere change due to the redox label. In this embodiment, the binding of a target analyte to a capture ligand which is sterically close to an EAM causes one or more of the small, polar ligands of the EAM to be replaced by one or more coordination atoms supplied by the target analyte, causing a change in the inner-sphere reorganization energy for at least two reasons. First, the exchange of a small, polar ligand for a putatively larger ligand will generally exclude more water from the metal, lowering the required solvent reorganization energy (i.e. an inner sphere $\lambda_i$ effect). Secondly, the proximity of a generally large target analyte to the relatively small redox active molecule will sterically exclude water within the first or second coordination sphere of the metal ion, also changing the solvent reorganization energy.

Alternatively, the invention relies on substitutionally inert ligand, plus outer sphere effects. In this embodiment exchange of the polar ligands on the metal ion by a target analyte coordination atom. Rather, in this embodiment, the polar ligands are effectively irreversibly bound to the metal ion, and the change in solvent reorganization energy is obtained as a result of the exclusion of water in the first or second coordination sphere of the metal ion as a result of the binding of the target analyte; essentially the water is excluded (i.e. an outer sphere $\lambda_o$ effect).

The present invention provides compounds with novel architecture and methods of using these compounds for detection of target analytes.

In some embodiments, the target analyte binds to the capture ligand. In some embodiments, the target analyte can be an enzyme, and the change in $E^0$ is as a result of an enzymatic event, as described in U.S. Patent Application No. 61/087,094, hereby incorporated by reference in its entirety.

In the embodiments of the invention, there is a change in the $E^0$, presumably due to a change in the reorganization energy, upon the introduction of the target analyte. As discussed more fully below, the change may be either a positive or negative shift in E0, depending on a variety of factors. In general, when cyano ligands are used, the change in $E^0$ can be a negative shift in $E^0$, although depending on the system and the other ligands used (if any), the effect of interaction of the target analyte with the capture ligand can result in a positive shift in $E^0$. Surprisingly, shifts of greater than about 50 mV, 100 mV, 150 mV, 200 mV, 250 mV and 300 mV can be seen using cyano ligands.

CN— is a good nucleophile and in an example, the Iron-cyano (−2) complex has a partial charge on the N of a cyano of −0.8767 and has a partial charge on the C of a cyano of 0.5549. That charge number on the nitrogen is very large that one can consider it acting like there is a lone pair of electrons. Therefore, the partial negative charge on the N arranges water molecules with the protons of water oriented toward the N (the opposite is true for NH3 ligands). Since the partial charge on the nitrogen is high, this local orientation effect is strong and therefore the delta between water near by (before target capture) and water excluded (after target capture) is high . . . i.e., the difference in lambda between the two states is quantitatively higher.

Unidentate CN— always binds through the carbon and therefore that large partial negative charge resides on the N. The larger that partial negative charge oriented toward the solvent (water) the larger the observable effect will be. As such, ligands with partial negative charges on the ligands stabilize high oxidation state metals, and have a strong impact on the orientation of water.

CN being the best because it has the highest net charge on the N and therefore the strongest interaction with protons of water:

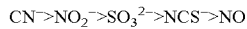

equiv to $NCS^-$ is $SCN^-$.

In general, the more positive the Metal center becomes the higher the potential of the metal. Accordingly, when most if not all the negative charges are neutralized by interaction with water, the metal becomes more positive.

II. Geometries of the Sensors

The present invention is directed to methods and compositions for detection of target analytes, based on a change of electrochemical potential, $E^0$, of a redox active molecule either on the surface of an electrode, or in some cases, in solution (while most of the description herein is directed to solid phase assays, as will be appreciated by those in the art, the invention can be used in solution as well, and such description herein is meant to apply as applicable to solution phase assays as well).

In general, the invention can be described as follows. A redox active molecule, generally comprising a transition metal and at least one ligand (such as one cyano ligand (or more, as described herein)) that provide coordination atoms for the transition metal, is attached to the surface of an electrode, generally through a linker as described herein. In addition, the electrode may also optionally comprise a self-assembled monolayer (SAM) as described herein. In the spatial vicinity of the redox active molecule, a capture ligand is also attached, generally in one of three ways, as described herein. Introduction and/or binding of the target analyte results in a change in the electrochemical potential of the redox active molecule, which is then detected in a variety of ways as described herein.

Figure 12A:
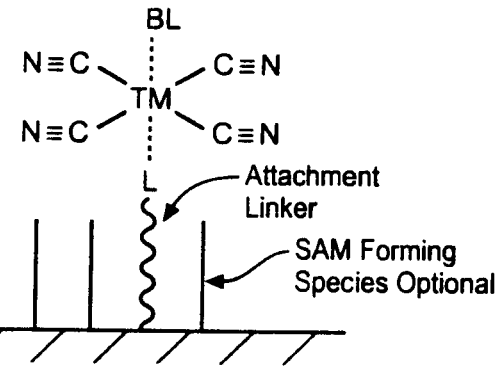
FIGS. 12A and C depicts the situation where a linker is attached at one end to the electrode and the other end terminates in a ligand (L) that provides a coordination atom for the transition metal (TM). The capture substrate (CS) provides an additional ligand (not depicted), and a plurality of other ligands provide the remaining coordination atoms. Upon action by the enzyme, the capture substrate results in a leaving group (X). It should be noted that these Figures depicts a situation where the transition metal utilizes 6 coordination atoms, but other numbers of coordination atoms can be used, depending on the metal. Similarly, these Figures depicts the use of ligands that provide a single coordination atom, but fewer ligands providing multiple coordination atoms (e.g. multidentate) ligands can be used as well.
Figure 12B:
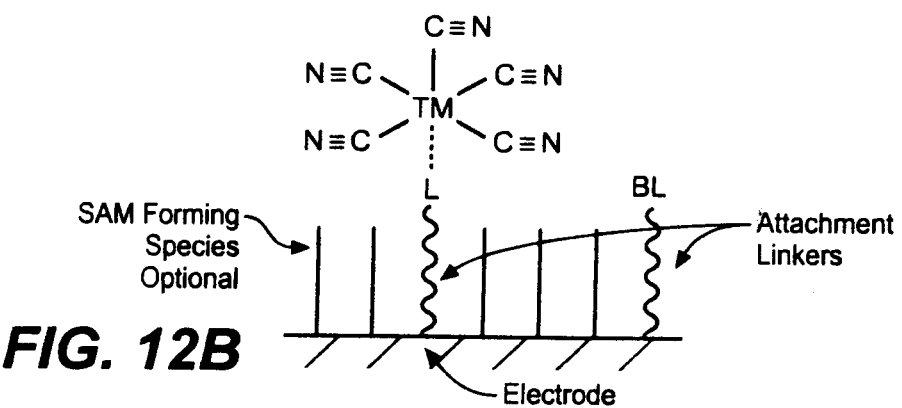
FIG. 12B depicts the situation where the capture substrate and the EAM are attached separately to the electrode.
Figure 12C:
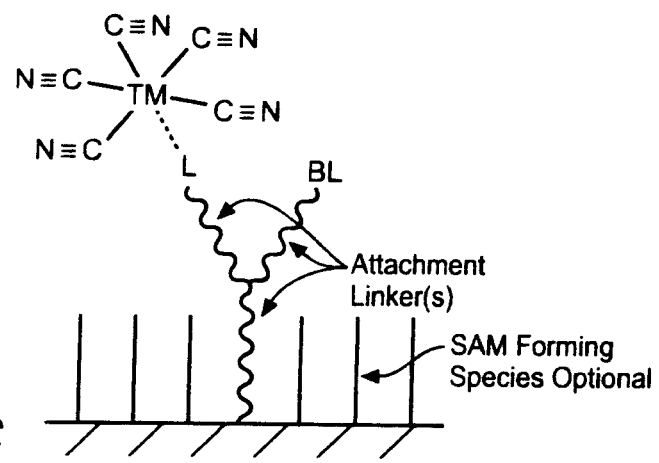
FIG. 12C depicts a similar situation to FIG. 3A, except the capture substrate does not provide a coordination atom to the transition metal. It should be appreciated that solution phase systems can be similar to FIGS. 12 and 14, in that the electrochemical potential of the EAM in solution can be altered as a result of the enzymatic activity of the target enzyme.
Figure 13:
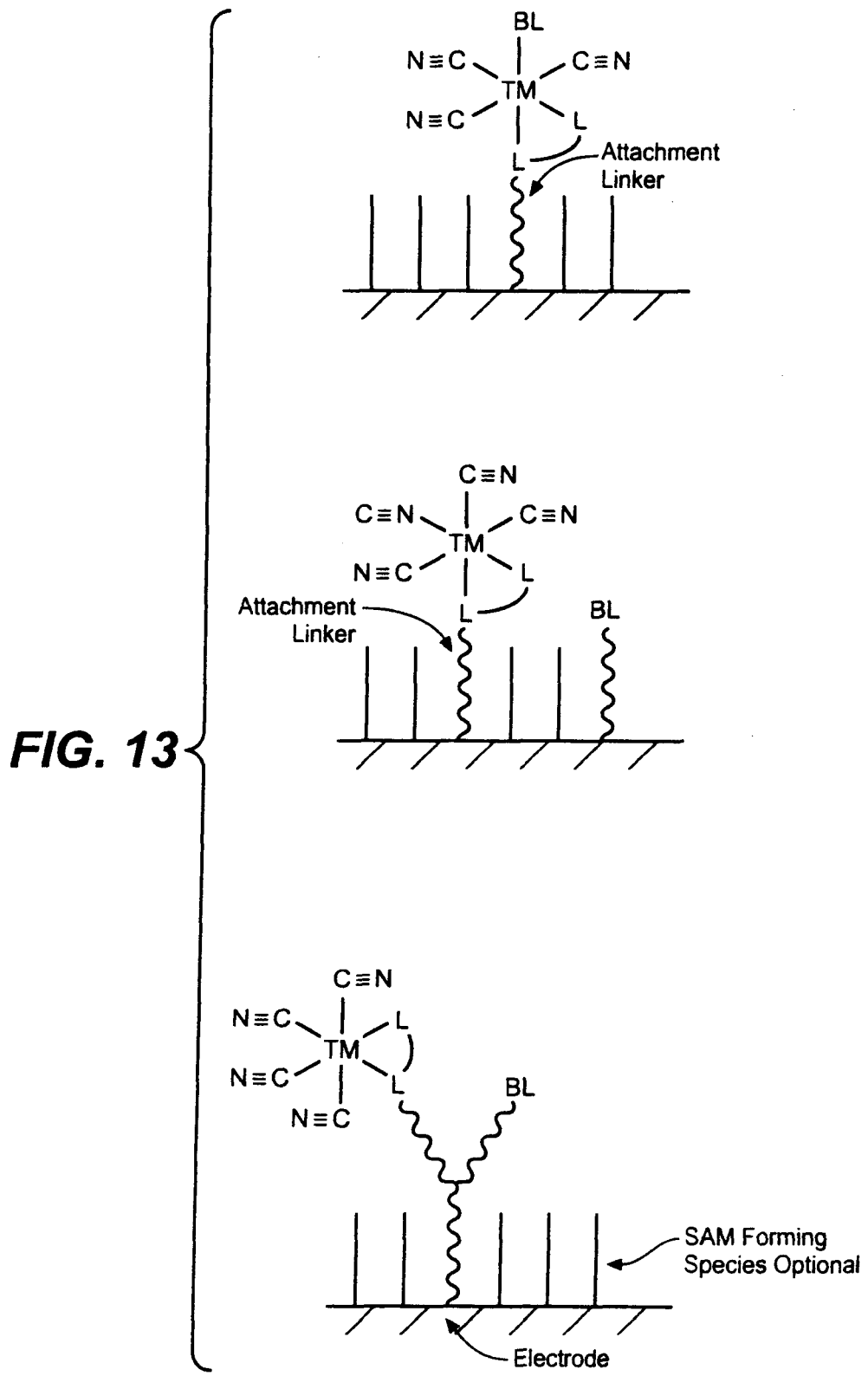
Figure 14:
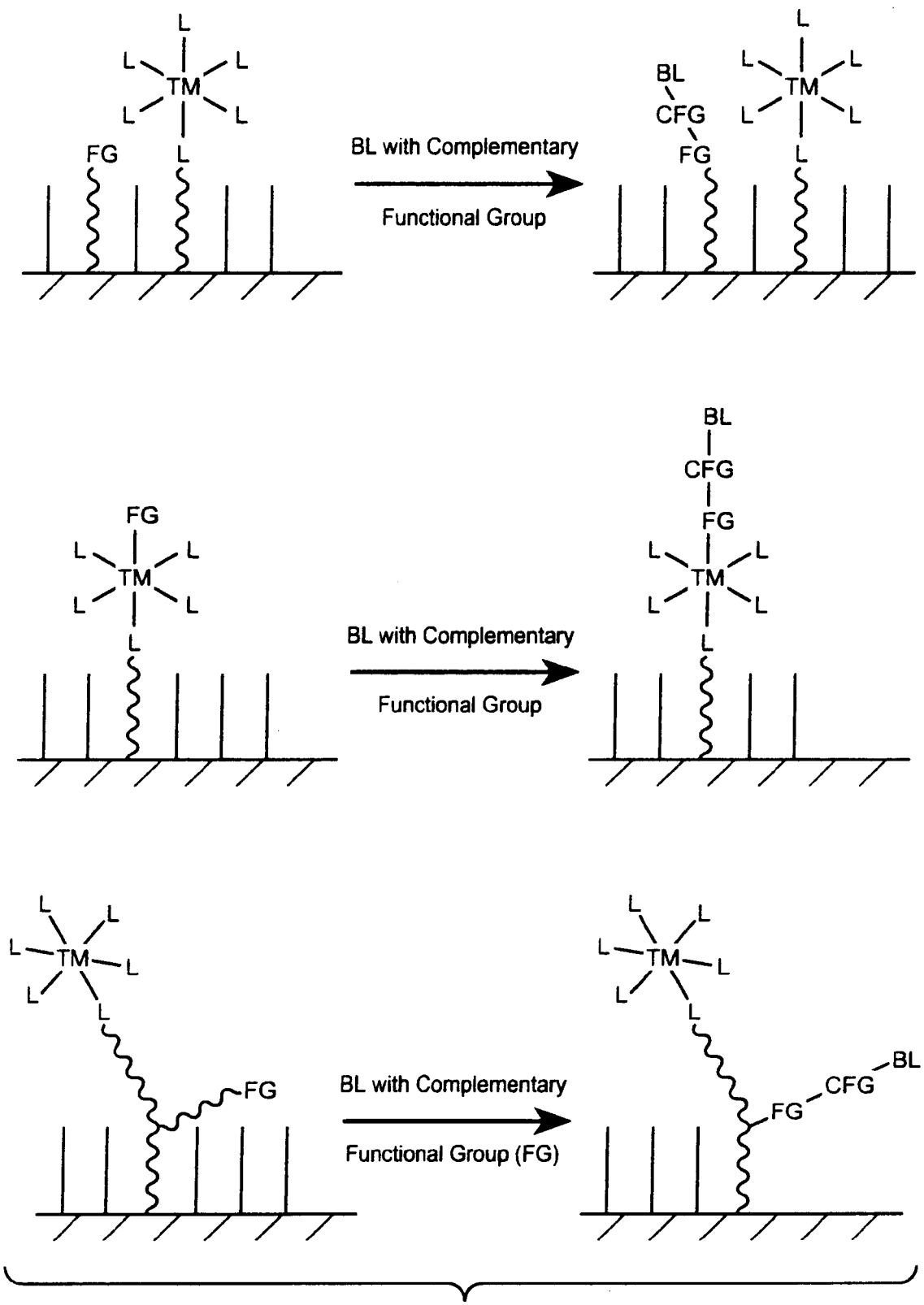
FIG. 14 depicts a general scheme for producing the biochips of the invention.

As depicted in FIGS. 12-14, there are three basic geometries for the sensor, although the descriptions herein are not meant to be so limited. In one embodiment, as shown in FIG. 12A, an electroactive moiety (EAM), comprising a transition metal ion and ligands that provide coordination atoms for the transition metal (in some embodiments, at least one of which is a cyano ligand), is attached to an electrode. In addition, a capture ligand (sometimes also referred to as a "binding ligand") that will specifically bind the target analyte is also attached to the electrode. Both species are generally attached to the electrode using an attachment linker as described herein. The two species are attached to the electrode in such a manner that they are spatially close, such that the $E^0$ of the EAM is altered upon binding of a target analyte. It should be noted that a third species, comprising a monolayer forming species, described below, can also be optionally present on the electrode. In this embodiment, the EAM species can have the formula (Ia), the capture ligand species can have the formula (Ib) and the diluent species can have the formula (Ic):

wherein AG is an anchor group, EAM is an electroactive moiety comprises a solvent accessible redox complex, spacer 1 is a SAM forming species described herein, CL is a capture ligand, and TG is a terminal group, with n being 0 or 1.

In a second embodiment, as depicted in Figure *XB, one of the coordination atoms for the transition metal of the EAM is provided by the capture ligand, forming a "redox active moiety complex", or ReAMC. In this embodiment, the coordination atom can be actually part of the capture ligand (e.g. if the capture ligand is a peptide, an amino group can provide the coordination atom) or part of a linker used to attach the capture ligand (e.g. a pyridine linker, etc.). The ReAMC is attached as a single species, and as above, an additional species, comprising a monolayer forming species, described below, can also be optionally present on the electrode. In this embodiment, the present invention provides a compound having the formula (II):

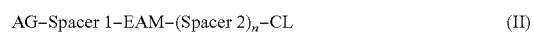

wherein AG is an anchor group, EAM is an electroactive moiety comprises a solvent accessible redox complex, CL is a capture ligand, spacer 1 is a SAM forming species described herein, and Spacer 2 is a linker, with n=0 or 1.

In a third embodiment, as depicted in FIG. 12C, there ReAMC is a single species, but the capture ligand does not provide a coordination atom; rather, it is spatially close but distinct from the EAM of the ReAMC. Again, a third species, comprising a monolayer forming species, described below, can also be optionally present on the electrode. In this embodiment, the present invention provides a compound having the formula (III):

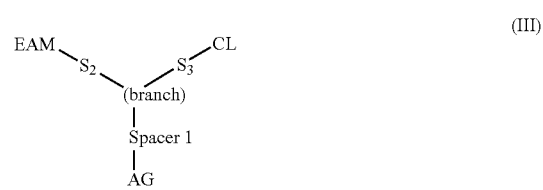

wherein AG is an anchor group, EAM is an electroactive moiety comprises a solvent accessible redox complex, CL is a capture ligand, spacer 1 is a SAM forming species described herein, and $S_2$ and $S_3$ are two linkages that link the EAM and CL together with the AG to form a branched structure. $S_2$ and $S_3$ can be different or the same.

One example of this configuration is shown below:

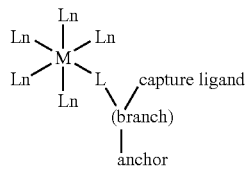

where M=transitional metal; Ln=coordinating ligand that covalently connected to the anchor and capture ligand, n=0 or 1; and L=coordinating ligand.

III. Electrode

In one aspect, the present invention provides these ligand architectures attached to an electrode. By "electrode" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary With the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the components of the system such as SAMs, EAMs and capture ligands bound to the inner surface. This allows a maximum of surface area containing the nucleic acids to be exposed to a small volume of sample.

The electrodes of the invention are generally incorporated into biochip cartridges and can take a wide variety of configurations, and can include working and reference electrodes, interconnects (including "through board" interconnects), and microfluidic components. See for example U.S. Pat. No. 7,312,087, incorporated herein by reference in its entirety.

The biochip cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

In a preferred embodiment, the biochips comprise substrates with a plurality of array locations. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety)

A. Self Assembled Monolayer Spacers

In some embodiments, the electrodes optionally further comprise a SAM. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target enzyme away from the electrode surface. In addition, a monolayer serves to keep charge carriers away from the surface of the electrode. Thus, this layer helps to prevent electrical contact between the electrodes and the ReAMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

In some embodiments, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electroactive polymers, that themselves may donate or accept electrons.

A more detailed description of conductive oligomers is found in WO11999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

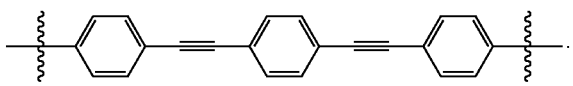

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in a preferred embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly)ethylene glycol, with —OCH$_2$CH$_2$OH, —(OCH$_2$CH$_2$)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

In some embodiments, the electrode further comprises a passivation agent, preferably in the form of a monolayer on the electrode surface. For some analytes the efficiency of analyte binding (i.e. hybridization) may increase when the binding ligand is at a distance from the electrode. In addition, the presence of a monolayer can decrease non-specific binding to the surface (which can be further facilitated by the use of a terminal group, outlined herein. A passivation agent layer facilitates the maintenance of the binding ligand and/or analyte away from the electrode surface. In addition, a passivation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —(CF$_2$)$_n$—, —(CHF)$_n$— and —(CFR)$_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —(CH2)16 molecules, still may transfer electrons, albeit at a slow rate.

In some embodiments, the insulators have a conductivity, S, of about $10^{-7} \Omega^{-1}$ cm$^{-1}$ or lower, with less than about $10^{-8} \Omega^{-1}$ cm$^{-1}$ being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. Preferably, the alkyl or heteroalkyl chains are from about four to about 18 atoms in length, and more preferably from about six to about 16 atoms in length/

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold). Preferably, insulators are of the form —(CH$^2$)$_n$— having a thiol or disulfide terminus for attachment to gold. Also preferable, the alternate end of the insulator is terminated in a hydrophylic group such as oligoethylene glycol, —OH, or —COOH.

In some embodiments, the electrode is a metal surface and need not necessarily have interconnects or the ability to do electrochemistry.

B. Anchor Groups

The present invention provides compounds comprising an anchor group. By "anchor" or "anchor group" herein is meant a chemical group that attaches the compounds of the invention to an electrode.

As will be appreciated by those in the art, the composition of the anchor group will vary depending on the composition of the surface to which it is attached. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

Structure 1

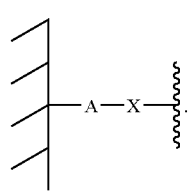

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via a nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

1). Pyridinyl Anchor Groups

In one aspect, the present invention provides the use of pyridine and derivatives thereof to attach the compounds of the invention to the surface.

In some embodiments, the anchor comprises a pyridyl group, having the structure of formula (II):

(II)

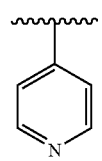

where the carbons on the ring can optionally and independently be substituted, using R groups as defined herein. Pyridine is a heterocyclic aromatic organic compound that is structurally related to benzene, wherein one CH group in the six-membered ring is replaced by a nitrogen atom. Pyridine can be used as a ligand in coordination chemistry. As a ligand, it is usually abbreviated as "py." The invention utilizes the ability of the lone electron pair on the nitrogen atom of the pyridine to bind to metal surfaces. One advantage of the pyridine based compounds is that they are air stable. Curtis et al., Inorg. Chem. 24:385-397 (1985); Callahan et al., Inorg. Chem. 14:1443-1453 (1975); Lavallee and Fleischer, J. Am. Chem. Soc. 94:2583-2599 (1972); and Jwo et al., J. Am. Chem. Soc. 101:6189-6197 (1979), all of which are incorporated by reference.

In some embodiments, the pyridyl group comprises a bipyridyl group (Bispyridylacetylene, BPA), comprising two pyridyl groups separated by an acetylene group, shown below:

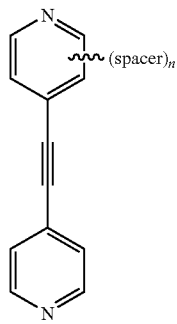

In this embodiment, the carbons on either ring can be optionally and independently be substituted, using R groups as defined herein. One of the rings will contain a linkage to a spacer, as defined herein, or, as shown in some of the figures, there may be more than one spacer attached to the pyridyl group (e.g. n=1 or more, with 2 finding particular use in some embodiments).

2). Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Thus, for example, when the electrode is a gold electrode, and "A" is a sulfur atom or moiety, such as generally depicted below in Structure 6, multiple sulfur atoms may be used to attach the conductive oligomer to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

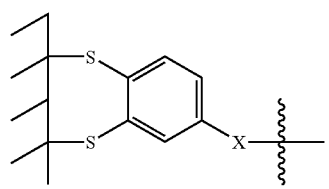

Structure 2

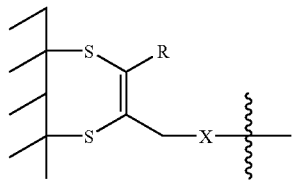

Structure 3

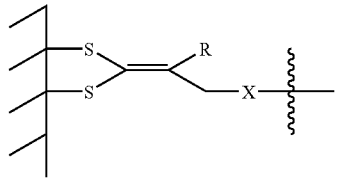

Structure 4

It should also be noted that similar to Structure 4, it may be possible to have a conductive oligomer terminating in a single carbon atom with three sulfur moieties attached to the electrode.

Figure 4A:
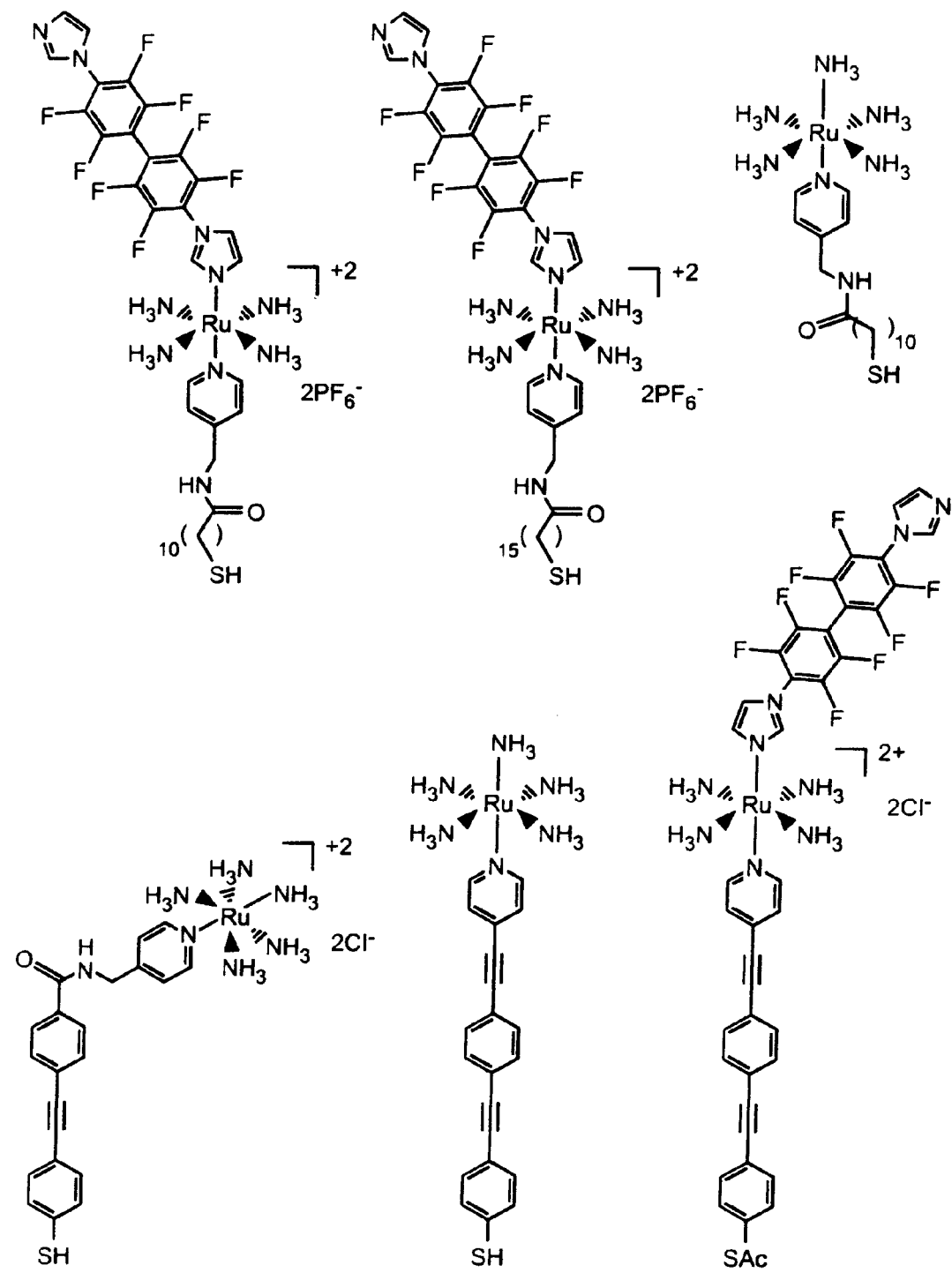
FIG. 4A depicts [BIM-Ru(NH$_3$)$_4$L]$^{2+}$ complexes with alkylthiol anchors.
Figure 4B:
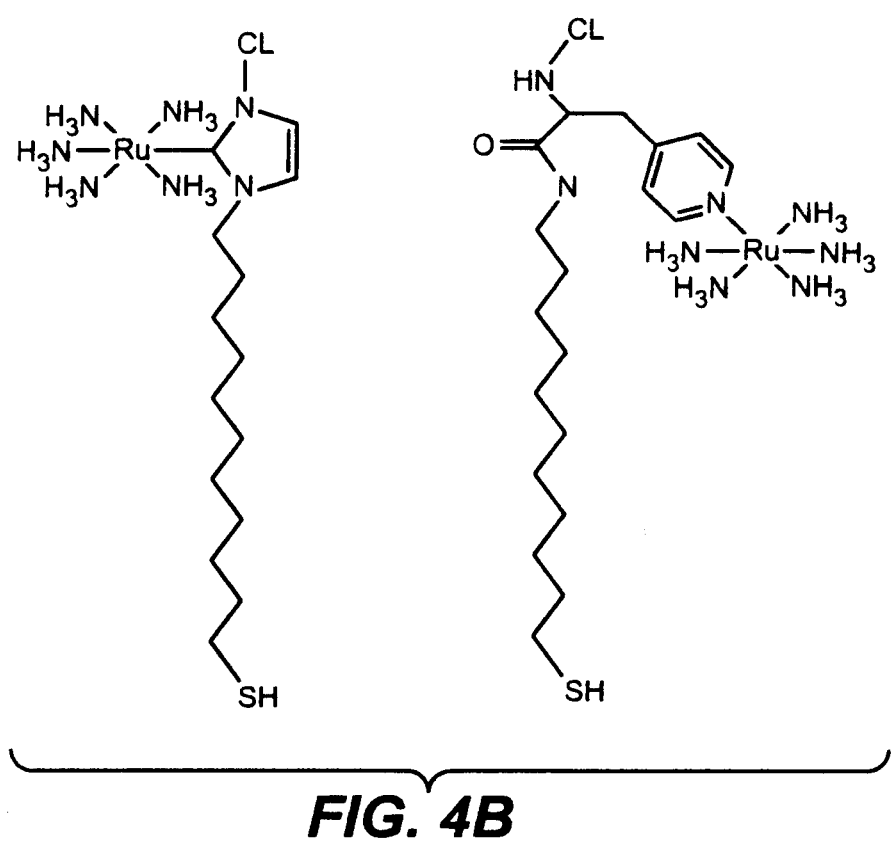
FIG. 4B depicts [Ru(NH$_3$)$_5$L]$^{2+}$ complexes with conjugated thiol anchors.

In another aspect, the present invention provide anchor comprise conjugated thiols. Some exemplary complexes with conjugated thiol anchors are shown in FIG. 4. In some embodiments, the anchor comprises an alkylthiol group. Some of the examples are shown in FIGS. 4A and 4B. The two compounds depicts in FIG. 4B are based on carbene and 4-pyridylalanine, respectively.

In another aspect, the present invention provides conjugated multipodal thio-containing compounds that serve as anchoring groups in the construction of electroactive moieties for analyte detection on electrodes, such as gold electrodes. That is, spacer groups (which can be attached to EAMs, ReAMCs, or an "empty" monolayer forming species) are attached using two or more sulfur atoms. These multipodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding headgroups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

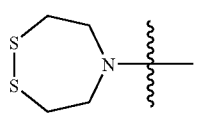

(IIIa)

In Structure (IIIa), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures.

In some embodiments, the anchor group and part of the spacer has the structure shown below

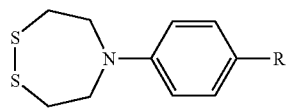

(IIIb)

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=1), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

C. Electroactive Moieties

In addition to anchor groups, the present invention provides compound comprising electroactive moieties. By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Particularly preferred are metals that do not change the number of coordination sites upon a change in oxidation state, including ruthenium, osmium, iron, platinium and palladium, with osmium, ruthenium and iron being especially preferred, and osmium finding particular use in many embodiments. In some embodiments, iron is not preferred. Generally, transition metals are depicted herein as TM or M.

The transitional metal and the coordinating ligands form a metal complex. By "ligand" or "coordinating ligand" (depicted herein in the figures as "L") herein is meant an atom, ion, molecule, or functional group that generally donates one or more of its electrons through a coordinate covalent bond to, or shares its electrons through a covalent bond with, one or more central atoms or ions.

The other coordination sites of the metal are used for attachment of the transition metal complex to either a capture ligand (directly or indirectly using a linker), or to the electrode (frequently using a spacer, as is more fully described below), or both. Thus for example, when the transition metal complex is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the transition metal complex to the electrode. For example, when the transition metal complex is attached to the electrode separately from the binding ligand as is more fully described below, all of the coordination sites of the metal (n) except 1 (n−1) may contain polar ligands.

Suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

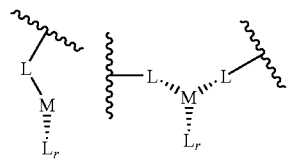

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, cyano (C≡N), $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

As will be appreciated in the art, any ligand donor(1)-bridge-donor(2) where donor (1) binds to the metal and donor (2) is available for interaction with the surrounding medium (solvent, protein, etc) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N═C═O), thiocyanates, isonitrile, $N_2$, $O_2$, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5$ (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [$(C_5H_5)_2$ Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other .pi.-bonded and .delta.-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene.

In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, $NH_2$; NHR; NRR', pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocyclic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g. at least one cyano ligand), bi-dentate, tri-dentate, and polydentate ligands (till to saturate) can be used in the construction of EAMs Generally, it is the composition or characteristics of the ligands that determine whether a transition metal complex is solvent accessible. By "solvent accessible transition metal complex" or grammatical equivalents herein is meant a transition metal complex that has at least one, preferably two, and more preferably three, four or more small polar ligands. The actual number of polar ligands will depend on the coordination number (n) of the metal ion. Preferred numbers of polar ligands are (n−1) and (n−2). For example, for hexacoordinate metals, such as Fe, Ru, and Os, solvent accessible transition metal complexes preferably have one to five small polar ligands, with two to five being preferred, and three to five being particularly preferred, depending on the requirement for the other sites, as is more fully described below. Tetracoordinate metals such as Pt and Pd preferably have one, two or three small polar ligands.

It should be understood that "solvent accessible" and "solvent inhibited" are relative terms. That is, at high applied energy, even a solvent accessible transition metal complex may be induced to transfer an electron.

Some examples of EAMs are described herein.

1). Cyano-Based Complexes

Figure 15:
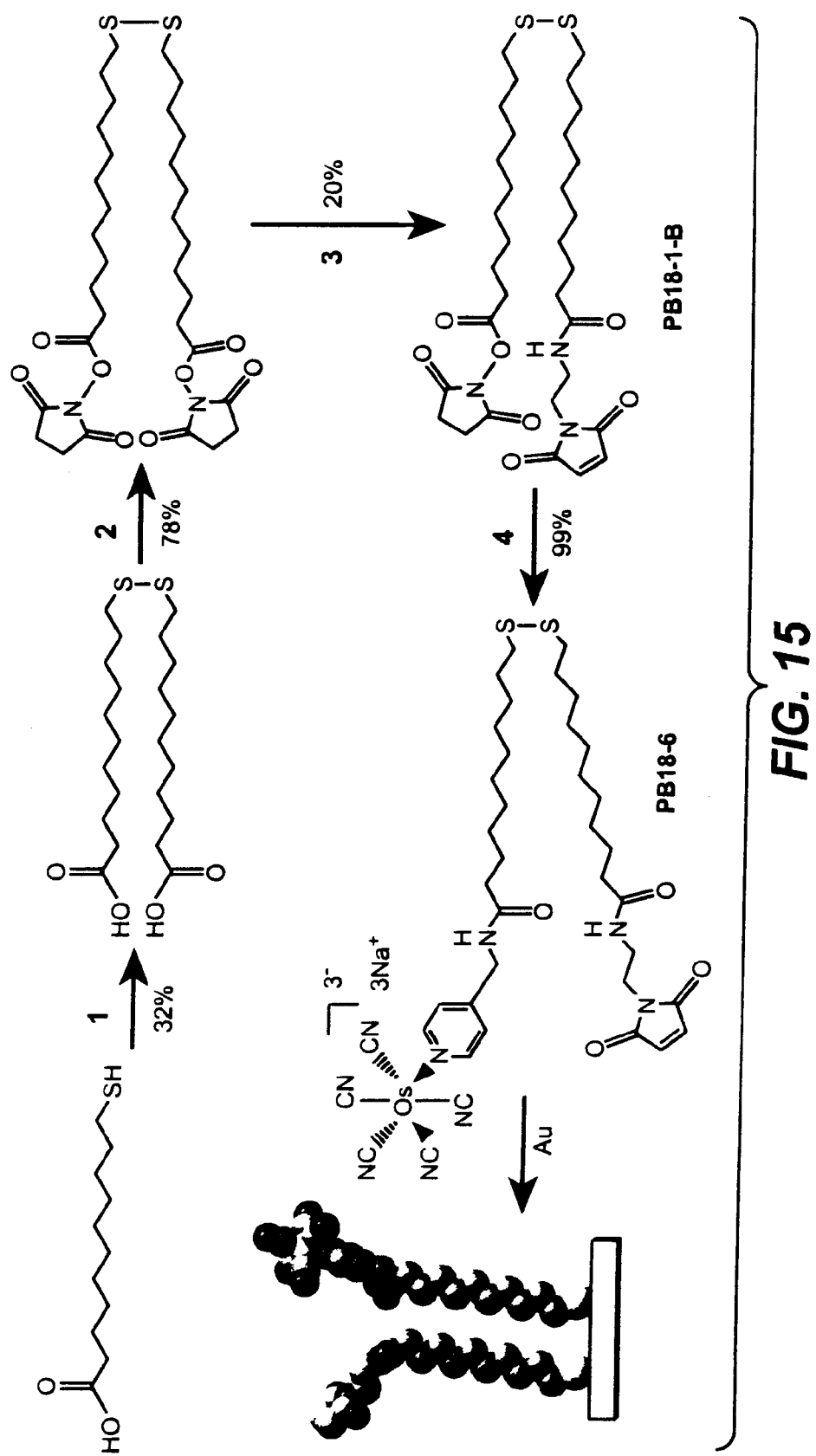
FIG. 15 shows a specific example of the production of FIG. 14.
Figure 16A:
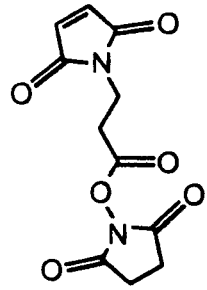
FIGS. 16A, B, C and D depict some exemplary compounds.
Figure 16B:
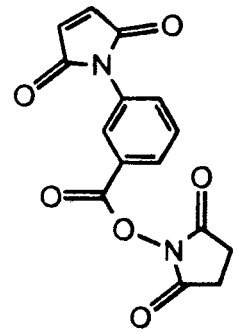
Figure 16C:
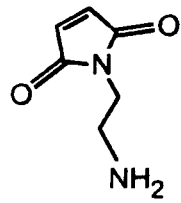
Figure 16D:
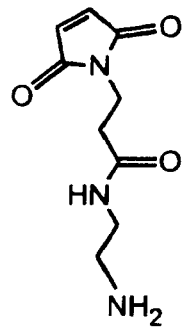

In one aspect, the present invention provides EAMs with a transition metal and at least one cyano (—C≡N) ligand. Depending on the valency of the metal and the configuration of the system (e.g. capture ligand contributing a coordination atom, etc.), 1, 2, 3, 4 or 5 cyano ligands can be used. In general, embodiments which use the most cyano ligands are preferred; again, this depends on the configuration of the system. For example, as depicted in FIG. 15, an EAM using a hexadentate metal such as osmium, separately attached from the capture ligand, allows 5 cyano ligands, with the 6th coordination site being occupied by the terminus of the attachment linker. When a hexadentate metal has both an attachment linker and a capture ligand providing coordination atoms, there can be four cyano ligands.

In some embodiments, such as depicted in the Figures, the attachment linker and/or the capture ligand can provide more than a single coordination atom. Thus, for example, in FIG. 17, the attachment linker comprises a bipyridine which contributes two coordination atoms.

In some embodiments, ligands other than cyano ligands are used in combination with at least one cyano ligand.

2). Ru—N Based Complexes

Figure 5B:
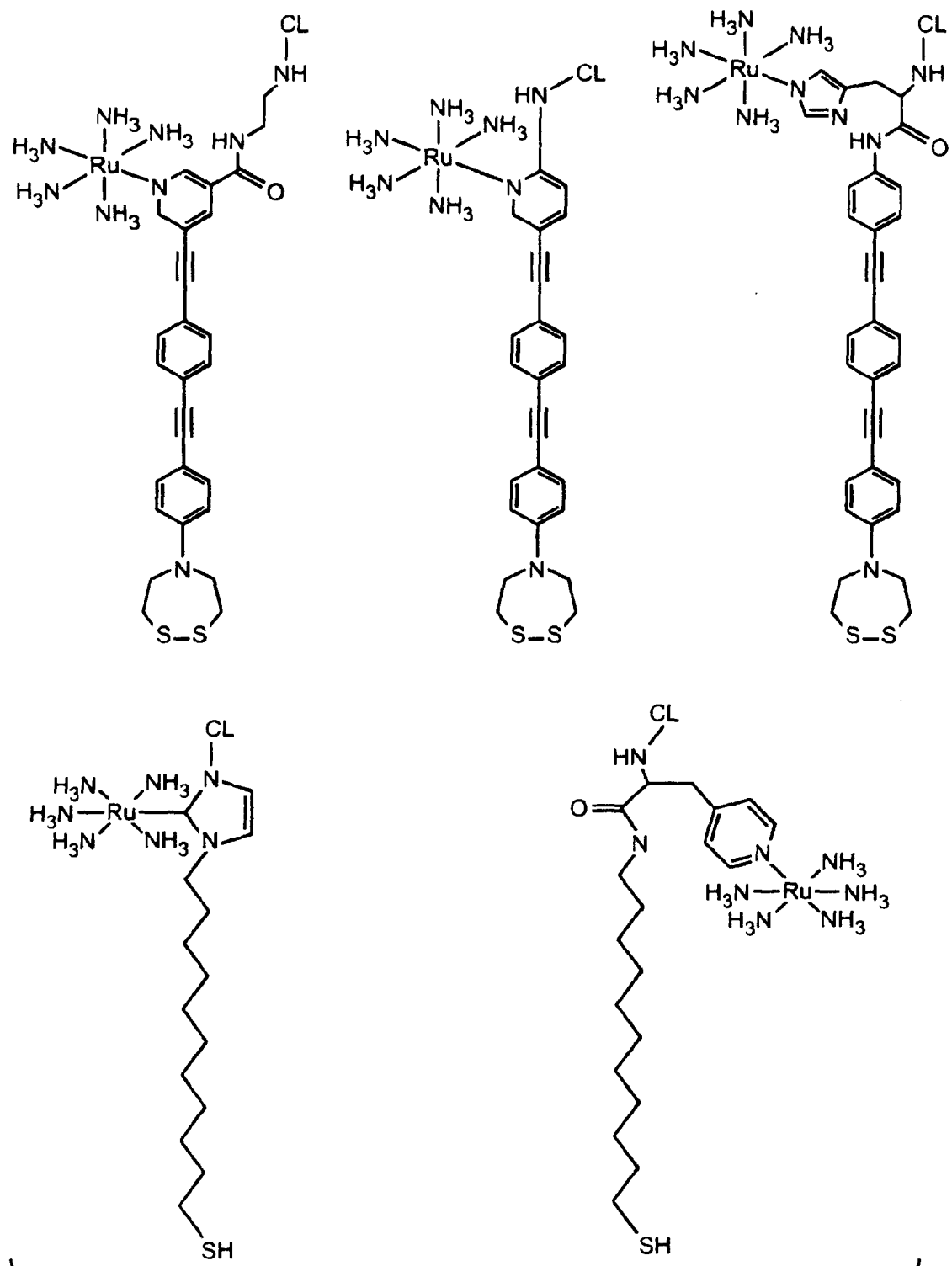
FIG. 5B depicts examples of Ru—N based complexes.

In one aspect, the resent invention provides new architectures for Ru—N based complexes, where the coordination could be monodentate, bidentate, tridentate, or multidendate. Thus the number of coordination ligand L (which covalently connected to the anchor and capture ligand) can be 1, 2, 3, or 4. Some of the examples are shown in FIG. 5A.

The charge-neutralizing ligands can be any suitable ligand known in the art, such as dithiocarbamate, benzenedithiolate, or Schiff base as described herein. The capture ligand and the anchor can be on the same framework or separate.

In another aspect of the present invention, each component of the EAM ligand architecture is connected through covalent bonds rather than Ru coordination chemistry. The construction of the architectures provide herein relies on modern synthetic organic chemical methodology. An important design consideration includes the necessary orthogonal reactivity of the functional groups present in the anchor and capture ligand component versus the coordinating ligand component. Preferably, the entire compound can be synthesized and the redox active transitional metal coordinated to the ligand near the last step of the synthesis. The coordinating ligands provided herein rely on well-established inorganic methodologies for ruthenium pentaamine precursors. See Gerhardt and Weck, J. Org. Chem. 71:6336-6341 (2006); Sizova et al., Inorg. Chim. Acta, 357:354-360 (2004); and Scott and Nolan, Eur. J. Inorg. Chem. 1815-1828 (2005), all herein incorporated by reference. Some examples of EAM architectures with Ru-pentaamine complexes are shown bellow in FIG. 5B.

As can be understood by those skilled in the art, the anchor components of the compounds provided herein could be interchanged between alkyl and multipodal-based thiols.

3). Ferrocene-Based EAMs

In some embodiments, the EAMs comprise substituted ferrocenes. Ferrocene is air-stable. It can be easily substituted with both capture ligand and anchoring group. Upon binding of the target protein to the capture ligand on the ferrocene which will not only change the environment around the ferrocene, but also prevent the cyclopentadienyl rings from spinning, which will change the energy by approximately 4 kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, all incorporated by reference.

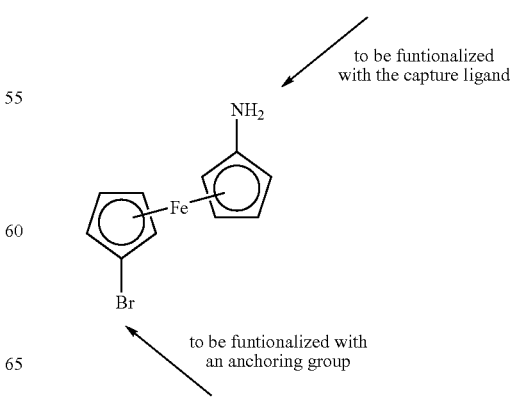

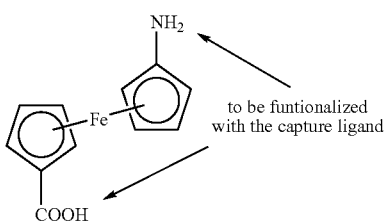

to be funtionalized with the capture ligand

In some embodiments the anchor and capture ligands are attached to the same ligand for easier synthesis. In some embodiments the anchor and capture ligand are attached to different ligands.

There are many ligands that can be used to build the new architecture disclosed herein. They include but not limited to carboxylate, amine, thiolate, phosphine, imidazole, pyridine, bipyridine, terpyridine, tacn (1,4,7-Triazacyclononane), salen (N,N'-bis(salicylidene) ethylenediamine), acacen (N,N'-Ethylenebis(acetylacetoniminate(–)), EDTA (ethylenediamine tetraacetic acid), DTPA (diethylene triamine pentaacetic acid), Cp (cyclopentadienyl), pincer ligands, and scorpionates. In some embodiments, the preferred ligand is pentaamine.

Pincer ligands are a specific type of chelating ligand. A pincer ligand wraps itself around the metal center to create bonds on opposite sides of the metal as well as one in between. The effects pincer ligand chemistry on the metal core electrons is similar to amines, phosphines, and mixed donor ligands. This creates a unique chemical situation where the activity of the metal can be tailored. For example, since there is such a high demand on the sterics of the complex in order to accommodate a pincer ligand, the reactions that the metal can participate in is limited and selective.

Scorpionate ligand refers to a tridentate ligand which would bind to a metal in a fac manner. The most popular class of scorpionates are the tris(pyrazolyl)hydroborates or Tp ligands. A Cp ligand is isolobal to Tp In some embodiments, the following restraints are desirable: the metal complex should have small polar ligands that allow close contact with the solvent.

4). Charge-Neutralizing Ligands

In another aspect, the present invention provides compositions having metal complexes comprising charged ligands. The reorganization energy for a system that changes from neutral to charged or from charged to neutral (e.g. $M(L)_n^+ <->M(L)_n^0$; $M(L)_n^- <->M(L)_n^0$) may be larger than that for a system in which the charge simply changes (e.g. $M(L)_n^{2+} <->M(L)_n^{3+}$) because the water molecules and surrounding ions have to "reorganize" more to accommodate the change to or from an uncharged state.

In some embodiments, charged ligand anionic compounds can be used to attach the anchor and the capture ligand to the metal center. A metal complex containing a halide ion X in the inner complex sphere reacts with charged ligands, including but not limited to, thiols (R—SH), thiolates (RS-E; E=leaving group, i.e., trimethylsilyl-group), carbonic acids, dithiols, carbonates, acetylacetonates, salicylates, cysteine, 3-mercapto-2-(mercaptomethyl) propanoic acid. The driving force for this reaction is the formation of HX or EX. If the anionic ligand contains both capture ligand and anchor, one substitution reaction is required, and therefore the metal complex, with which it is reacted, needs to have one halide ligand in the inner sphere. If the anchor and capture ligand are introduced separately the starting material generally needs to contain two halide in the inner coordination sphere. Seidel et al., Inorg. Chem. 37:6587-6596 (1998); Kathari and Busch, Inorg. Chem. 8:2276-2280 (1978); Isied and Kuehn J. Am. Chem. Soc. 100:6752-6754; and Volkers et al., Eur. J. Inorg. Chem. 4793-4799 (2006), all herein incorporated by reference.

Examples for suitable metal complexes are the following (it should be noted that the structures depicted below show multiple unidentate ligands, and multidentate ligands can be substituted for or combined with unidentate ligands such as cyano ligands):

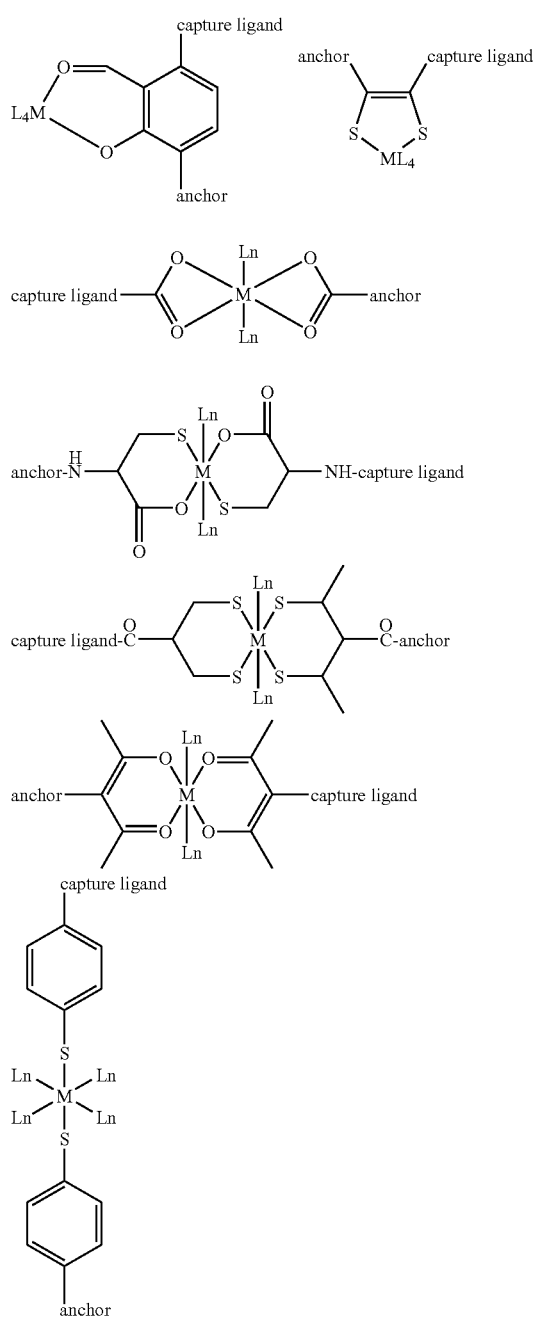

In some embodiments, dithiocarbamate is used as a charge-neutralizing ligand, such as the following example:

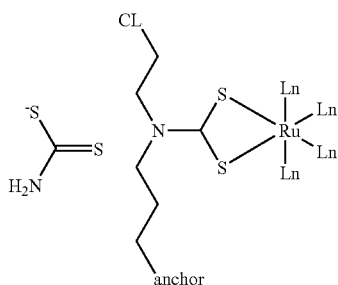

In some embodiments, benzenedithiolate is used as charge-neutralizing ligand, such as the following example:

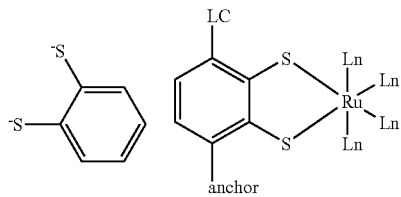

In the above depicted structures, Ln is coordinate ligand and n=0 or 1.

In some embodiments, the EAM comprises Schiff base type complexes. By "Schiff base" or "azomethine" herein is meant a functional group—that contains a carbon-nitrogen double bond with the nitrogen atom connected to an aryl or alkyl group but not hydrogen. Schiff bases are of the general formula $R_1R_2C=N-R_3$, where $R_3$ is a phenyl or alkyl group that makes the Schiff base a stable imine. Schiff bases can be synthesized from an aromatic amine and a carbonyl compound by nucleophilic addition forming a hemiaminal, followed by a dehydration to generate an imine.

Acacen is a small planar tetradentate ligand that can form hydrogen bonds to surrounding water molecules through its nitrogen and oxygen atoms, which would enhance the reorganization energy effect. It can be modified with many functionalities, including but not limited to, carboxylic acid and halides, which can be used to couple the acacen-ligand to the capture ligand and to the anchoring group. This system allows a large variety of different metal centers to be utilized in the EAMs. Since the ligand binds with its two oxygen and two nitrogen atoms, only four coordination sites are occupied. This leaves two additional coordination sites open, depending on the metal center. These coordination sites can be occupied by a large variety of organic and inorganic ligands. These additional open sites can be used for inner-sphere substitution (e.g. labile $H_2O$ or $NH_3$ can be displaced by protein binding) or outer-sphere influence (e.g. CO, CN can for H-bonds) to optimize the shift of potentials upon binding of the capture ligand to the target. WO/1998/057158, WO/1997/21431, Louie et al., PNAS 95:6663-6668 (1999), and Bottcher et al., Inorg. Chem. 36:2498-2504 (1997), herein all incorporated by reference.

In some embodiments, salen-complexes are used as well. Syamal et al., Reactive and Functional Polymers 39:27-35 (1999).

The structures of some acacen-based complexes and salen-based complexes are shown below, where positions on the ligand that are suitable for functionalization with the capture ligand and/or the anchor are marked with an asterisk.

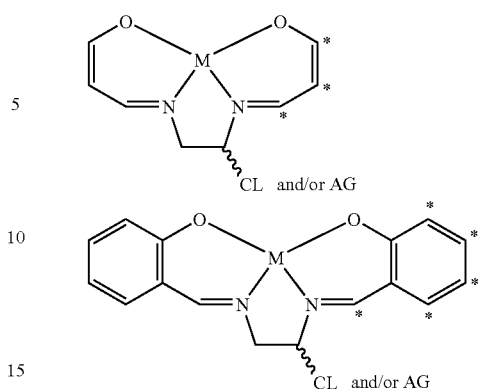

One example of using acacen as ligand to form a cobalt complex is the following:

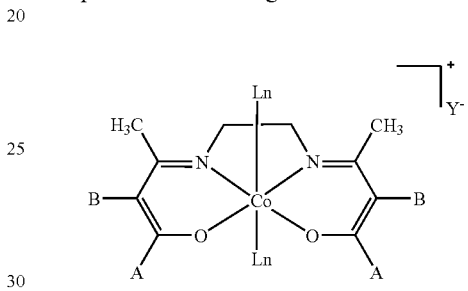

wherein is A and B are substitute groups, Ln is coordinating ligand and n=0 or 1, and Y is a counterion.

5). Sulfato Ligands

In some embodiments, the EAM comprises sulfato complexes, including but not limited to, $[L-Ru(III)(NH_3)_4SO_4]^+$ and $[L-Ru(III)(NH_3)_4SO_2]^{2+}$. The $SO_4$—Ru(III)-complexes are air stable. The ligand L comprises a capture ligand and anchor. The sulfate ligand is more polar than amine and negatively charged. The surface complexes therefore will have a larger reorganization energy contribution from surrounding water molecules than both the $[L-Ru(NH_3)-4-L']$ and $[L-Ru(NH_3)_5]^{2+}$. Isied and Taube, Inorg. Chem. 13:1545-1551 (1974), herein incorporated by reference.

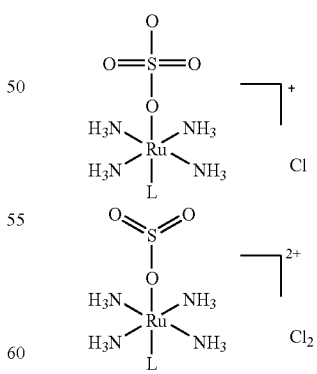

6). EAM with Multiple Metals

In one aspect of the present invention multiple metal centers are incorporated to a single ligand complex and thereby increases the signal. This arrangement increases the ratio of metals per target, resulting in a higher sensitivity.

Figure 19:
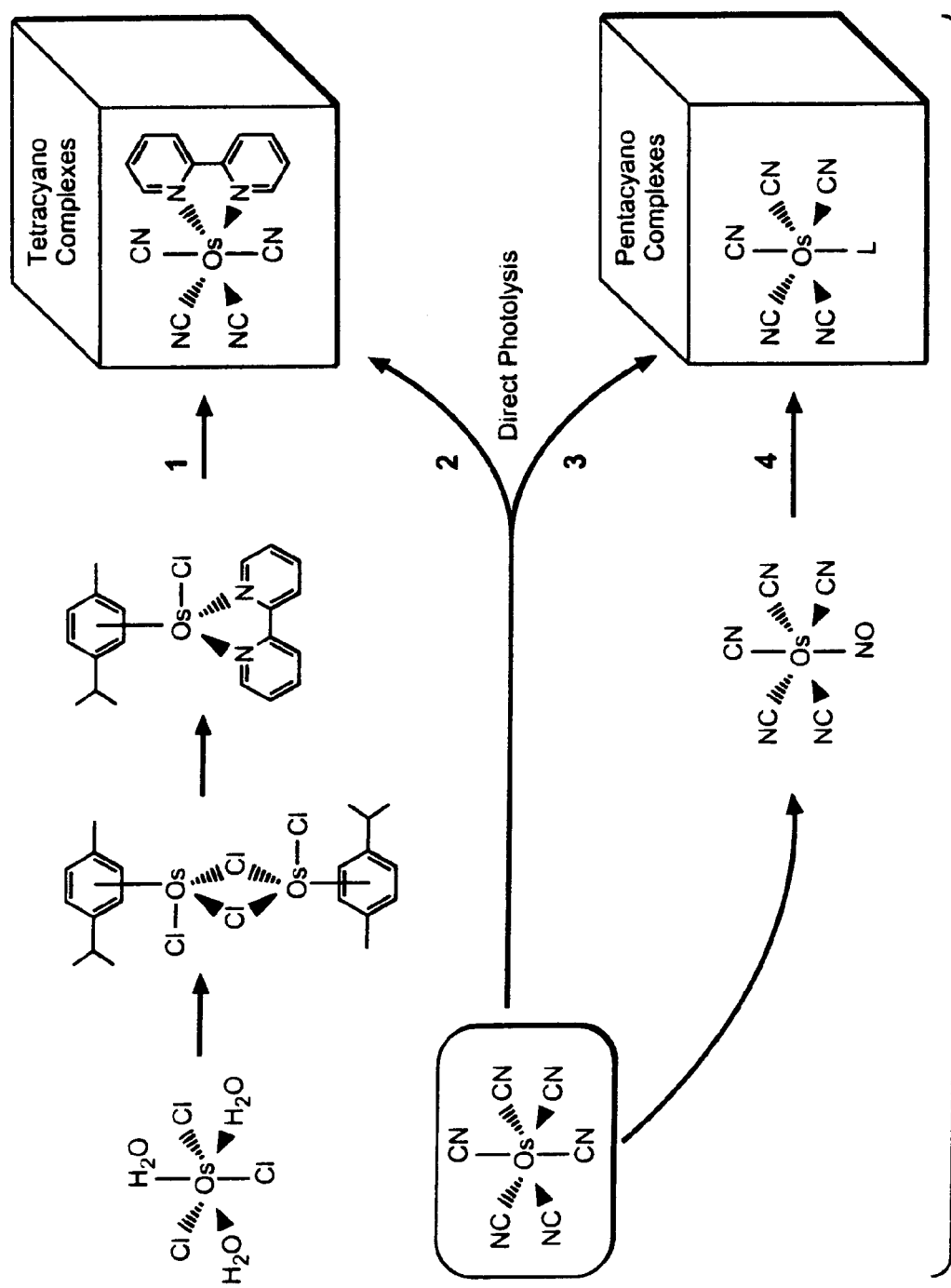
FIG. 19 depicts a general scheme of synthesis.
Figure 20:
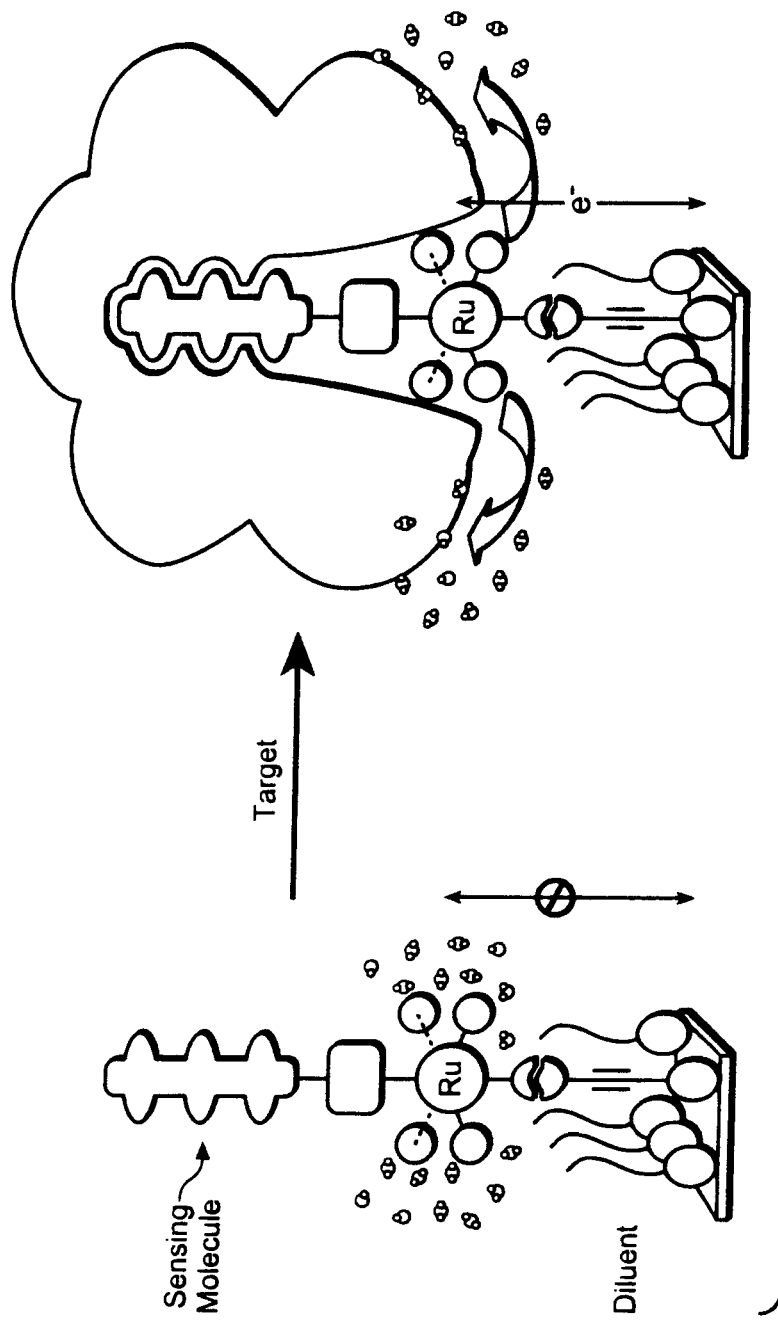
FIG. 20 depicts a general detection scheme.
Figure 21B:
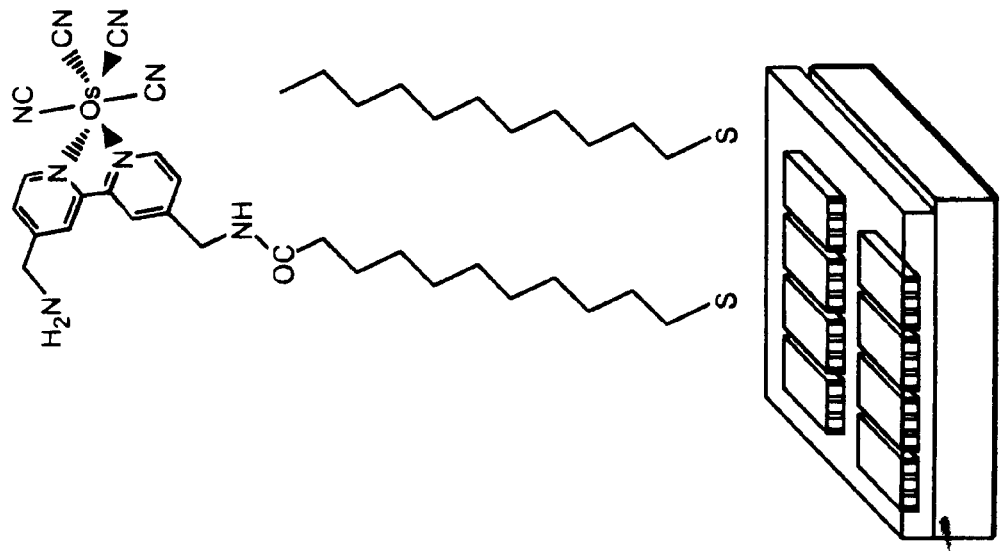
FIGS. 21A, B, C, D and E depict some exemplary compounds. Similar compounds can be constructed with different anchors, such as disulfide cyclic anchor groups, for example, or different spacers.
Figure 21A:
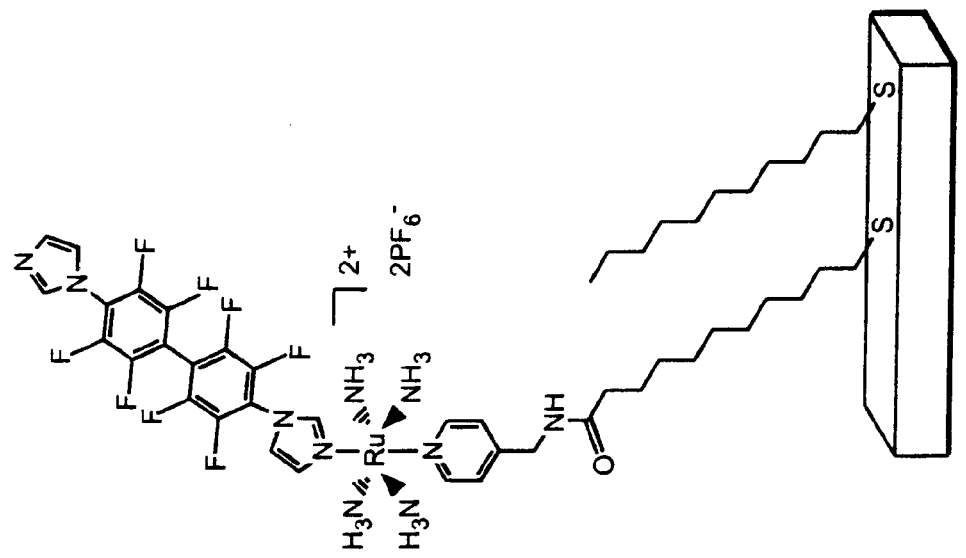
Figure 21E:
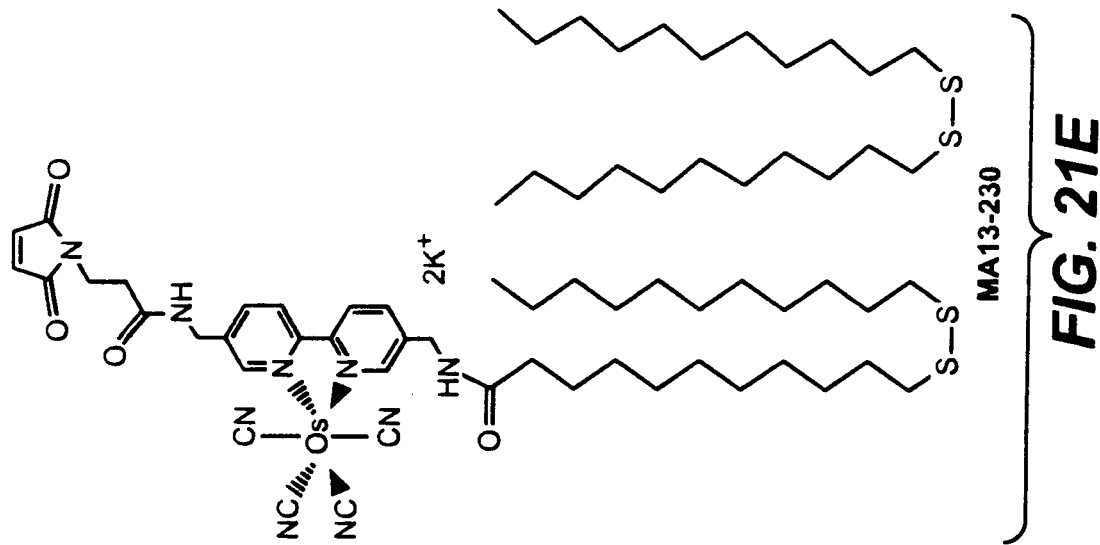
Figure 21D:
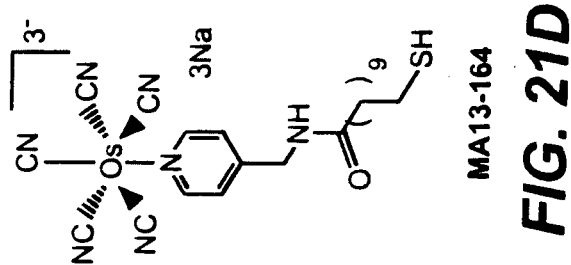
Figure 21C:
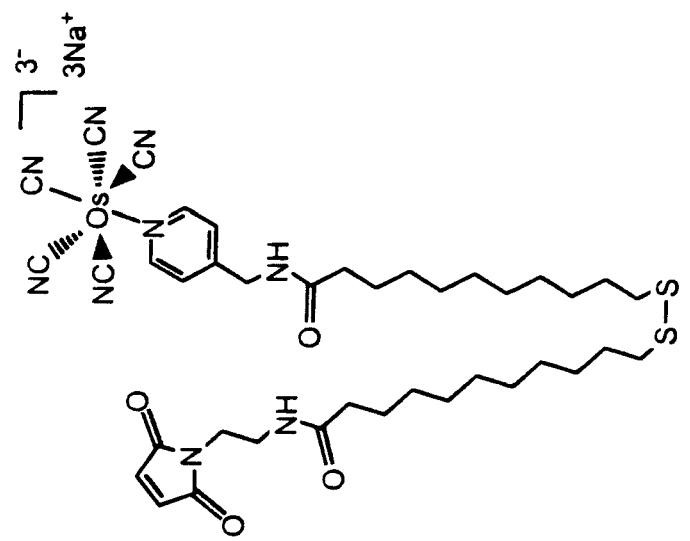
Figure 22:
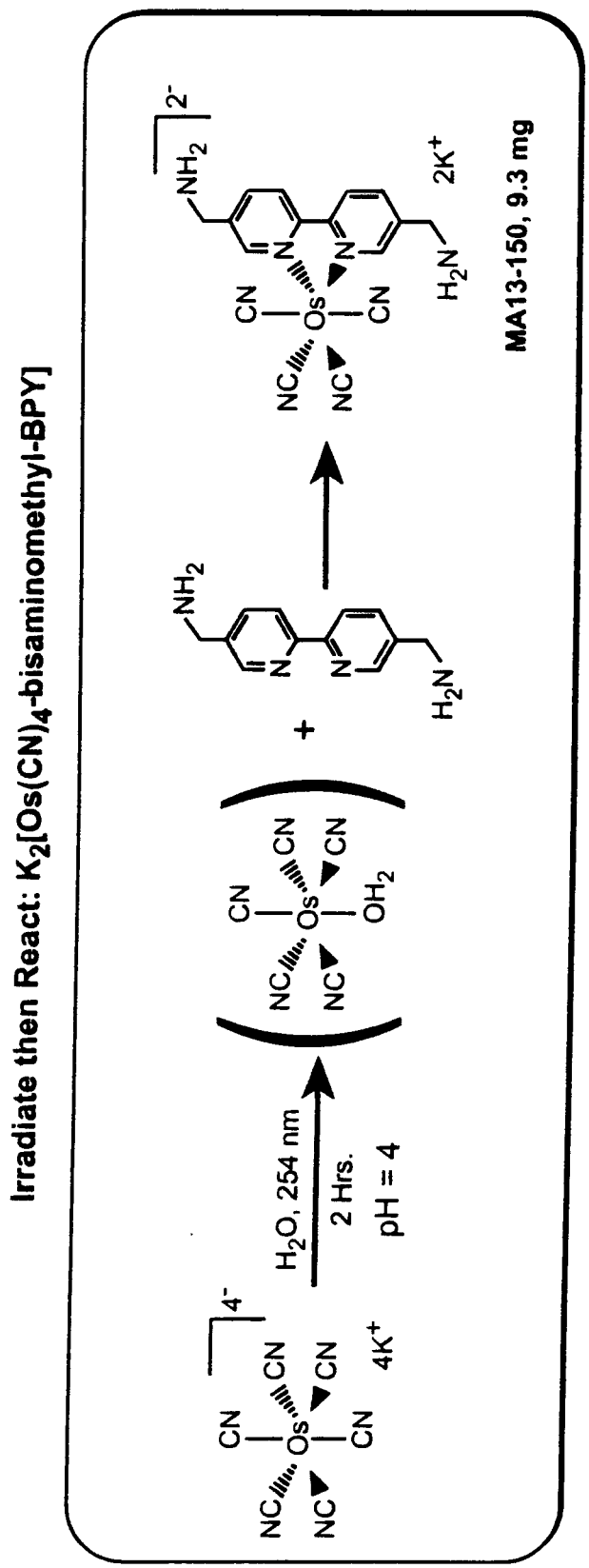
FIG. 22 depicts a general scheme of synthesis.
Figure 23:
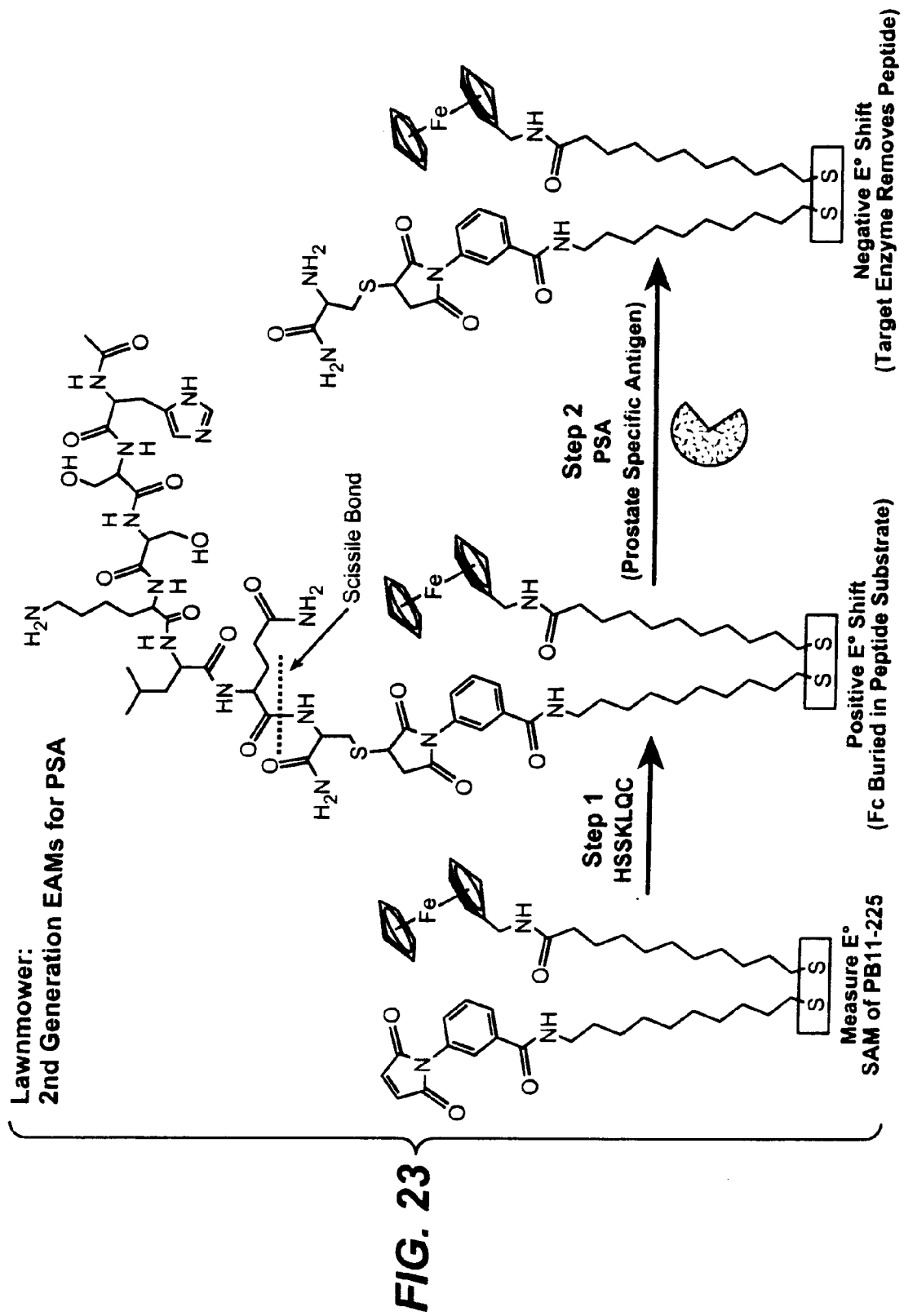
FIG. 23 depicts a general scheme of synthesis for an assay.
Figure 25A:
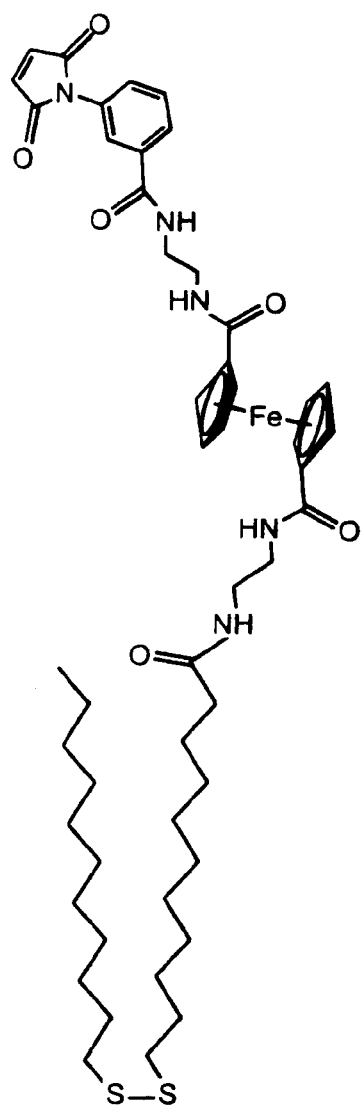
FIGS. 25A, B, C and D depict some exemplary compounds. Similar compounds can be constructed with different anchors, such as disulfide cyclic anchor groups, for example, or different spacers.
Figure 25B:
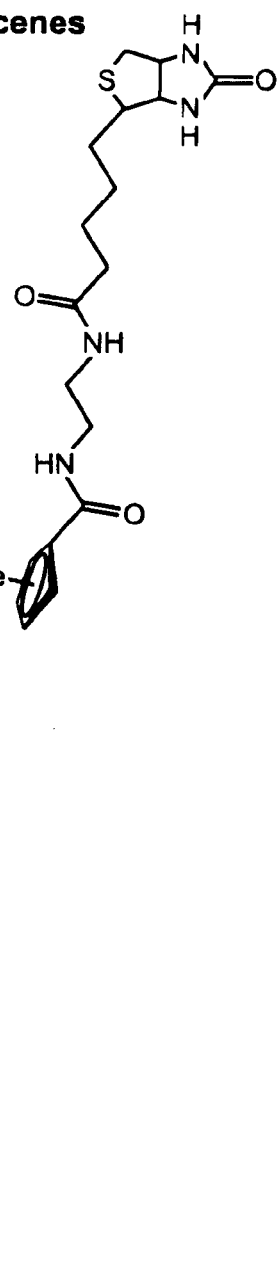
Figure 26A:
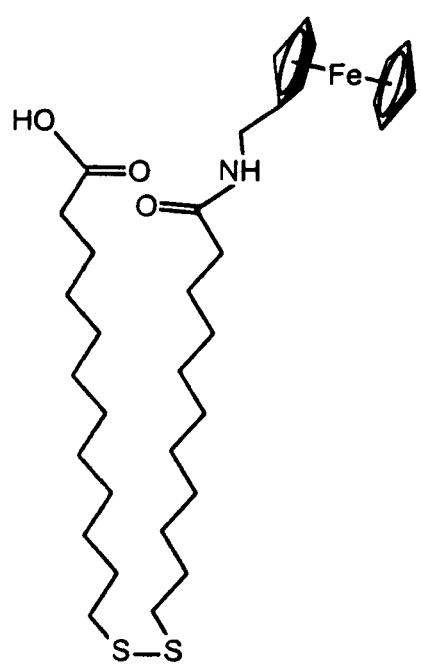
FIGS. 26A, B, C and D depict some exemplary compounds using ferrocene as the EAM. Similar compounds can be constructed with different anchors, such as disulfide cyclic anchor groups, for example, or different spacers.
Figure 26B:
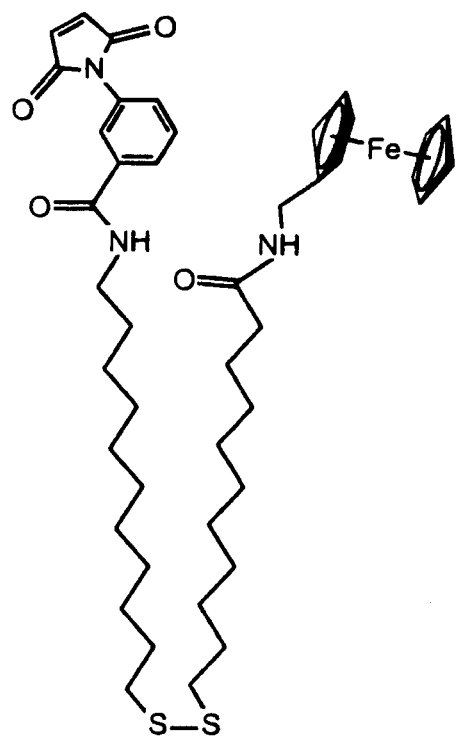
Figure 26C:
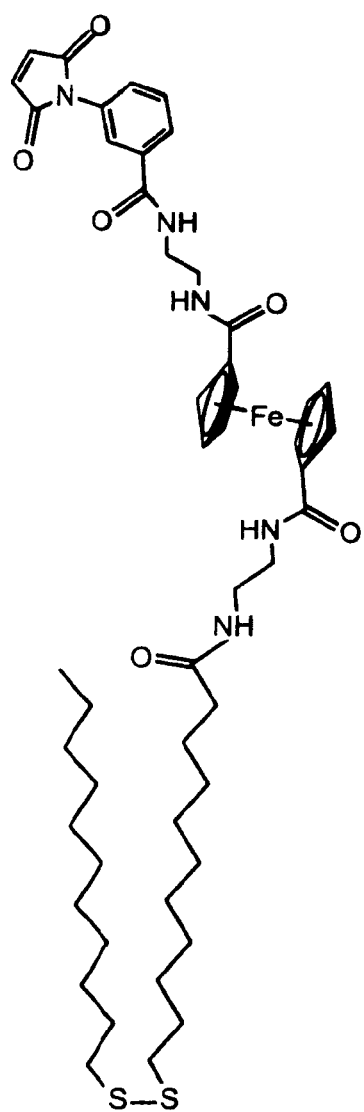
Figure 26D:
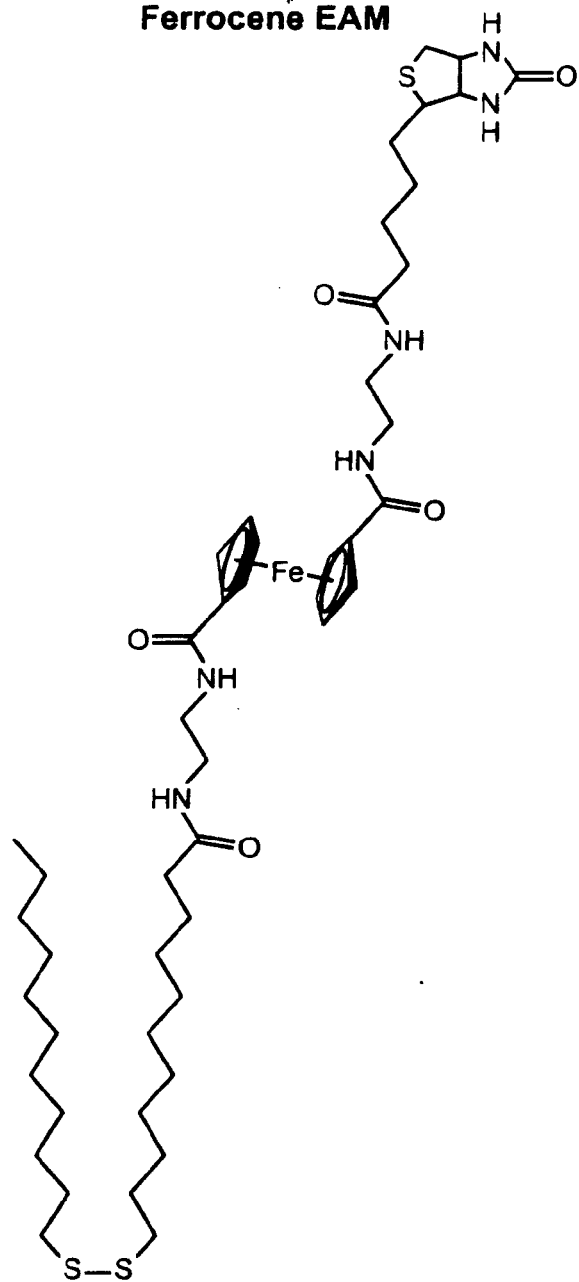

In some embodiments, multiple metal centers are present close to the capture ligand of an anchoring moiety to enable larger interaction with the analyte of interest (target). Having more than one reporter metal per analyte could boost the signal to noise ratio, increasing the sensitivity of the device. One of such examples is shown in FIG. 19.

Figure 6A:
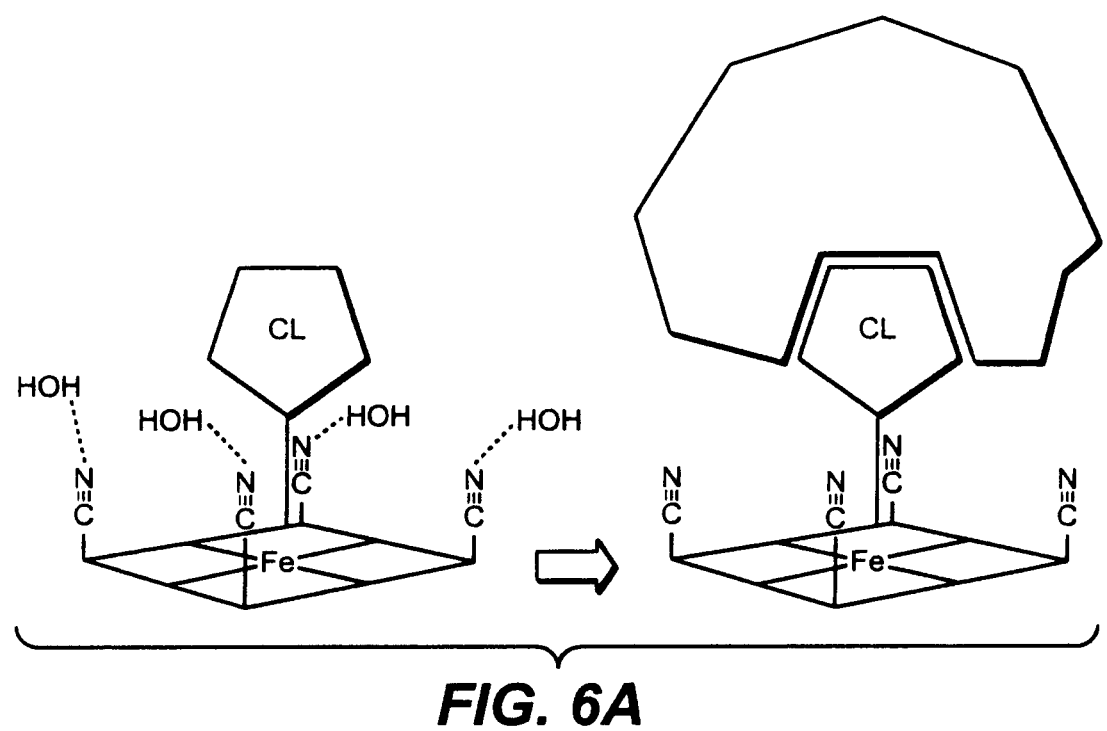
FIG. 6A schematically depicts modified Prussian blue surface for detection with amplification.

In some embodiments Prussian blue (PB) is used. Prussian blue is an inorganic, three-dimensional polymer (see below) that can be formed chemically or electrochemically from simple iron cyanide precursors. Other metals such as Mn and V and Ru have also been incorporated into PB-like films. Films of 50-100 nm thickness are formed quickly. An iron (or other similar metal) complex with a capture ligand can be incorporated on the surface of the film by combining this complex with the precursors during the formation of the film:

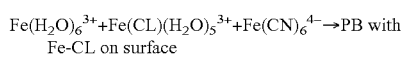
$Fe(H_2O)_6^{3+} + Fe(CL)(H_2O)_5^{3+} + Fe(CN)_6^{4-} \rightarrow$ PB with Fe-CL on surface When the target analyte (such as a protein) binds, the hydrogen bonding of water to cyano groups and other water molecules on the surface will be disrupted, and will affect more metals than just the one with the capture ligand. The electrochemical signal will be drastically changed due to this amplification. See FIG. 6A. In some embodiments a background subtraction of the signal before protein binding may be advantageous.

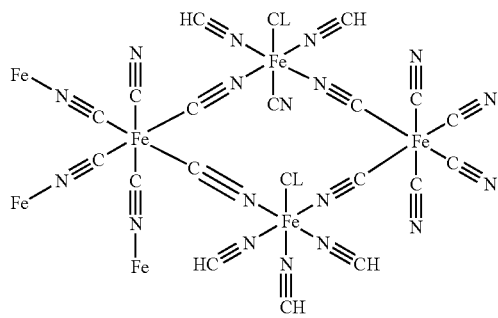

In the example shown above, the axial positions on the iron metal are functionalized with capture ligands arranged orthogonal to the surface. The binding of a single target to the functionalized surface will impact the metal that is directly attached as well as adjacent metal centers.

The Fe-CL complex may be added after initial formation of the film so that it will be incorporated on the surface only, and not cause excessive defects. The film thickness can be controlled by the time the chemical reaction is allowed to proceed or by how much current is applied to the solution if formed electrochemically.

Alternatively, islands of PB can be grown between areas of alkane or conjugated SAMs with or without the capture ligand. This would require nanopatterning and would help prevent electrochemical signals from extraneous species in the sample solution.

The metal can be used include, but not limited to, ruthenium, iron, rhenium, and osmium, with the appropriate ligand structure associated with each.

When there are multiple metals in the same complex the connectivity between the multiple metal centers generally should not allow "cross-talk" between the metals; but should rather be insulating.

7). Crown Ether Ligands

In one aspect, the present invention provides compositions where polar groups, such as crown ethers (CEs), are introduced in the vicinity to the metal center. This could increase the potential shift upon binding of a target analyte (e.g. a protein) to an EAM and therefore increase the sensitivity of the probe.

Crown ethers are heterocyclic chemical compounds that, in their simplest form, are cyclic oligomers of ethylene oxide. The essential repeating unit of any simple crown ether is ethyleneoxy, i.e., —$CH_2CH_2O$—, which repeats twice in dioxane and six times in 18-crown-6. In general, macrocycles of the (—$CH_2CH_2O$—)$_n$ type in which n≥4 are referred to as "crown" ethers rather than by their lengthier systematic names: for instance, the systematic name of 18-crown-6 is "1,4,7,10,13,16-hexaoxacyclooctadecane." The first number in a crown ether's name refers to the number of atoms in the cycle, and the second number refers to the number of those atoms which are oxygen.

Also envisioned by the present invention are crown ether derivatives.

This embodiment of the is based on having a second-sphere moiety bound to the ruthenium center of the EAM prior to the protein binding event. It has been shown that having a crown ether hydrogen bonded to pentaammine ruthenium complexes shifts the redox potential significantly (up to ~100 mV) negative in acetonitrile. See Ando, Coordination Chemistry Reviews, 248:185-203 (2004), and references therein; Ando et al., Polyhedron, 11:2335-2340 (1992); Zang et al., Inorg. Chem., 4738-4743 (1994); Todd et al. Inorg. Chem., 32:2001-2001 (1993); Dong et al., J. Am. Chem. Soc., 115, 4379-4380 (1993), all herein incorporated by reference.

The applicants have observed a positive shift in redox potential upon protein binding to the EAM provided herein, thus the use of crown ether would amplify this effect. By having some electron donating moiety (i.e. crown ether) bound to the metal center prior to protein binding "stacks the deck" for us by moving our initial potential more negative such that upon protein binding the crown ether is displaced (changing the second sphere coordination) giving a larger positive potential shift.

Figure 6B:
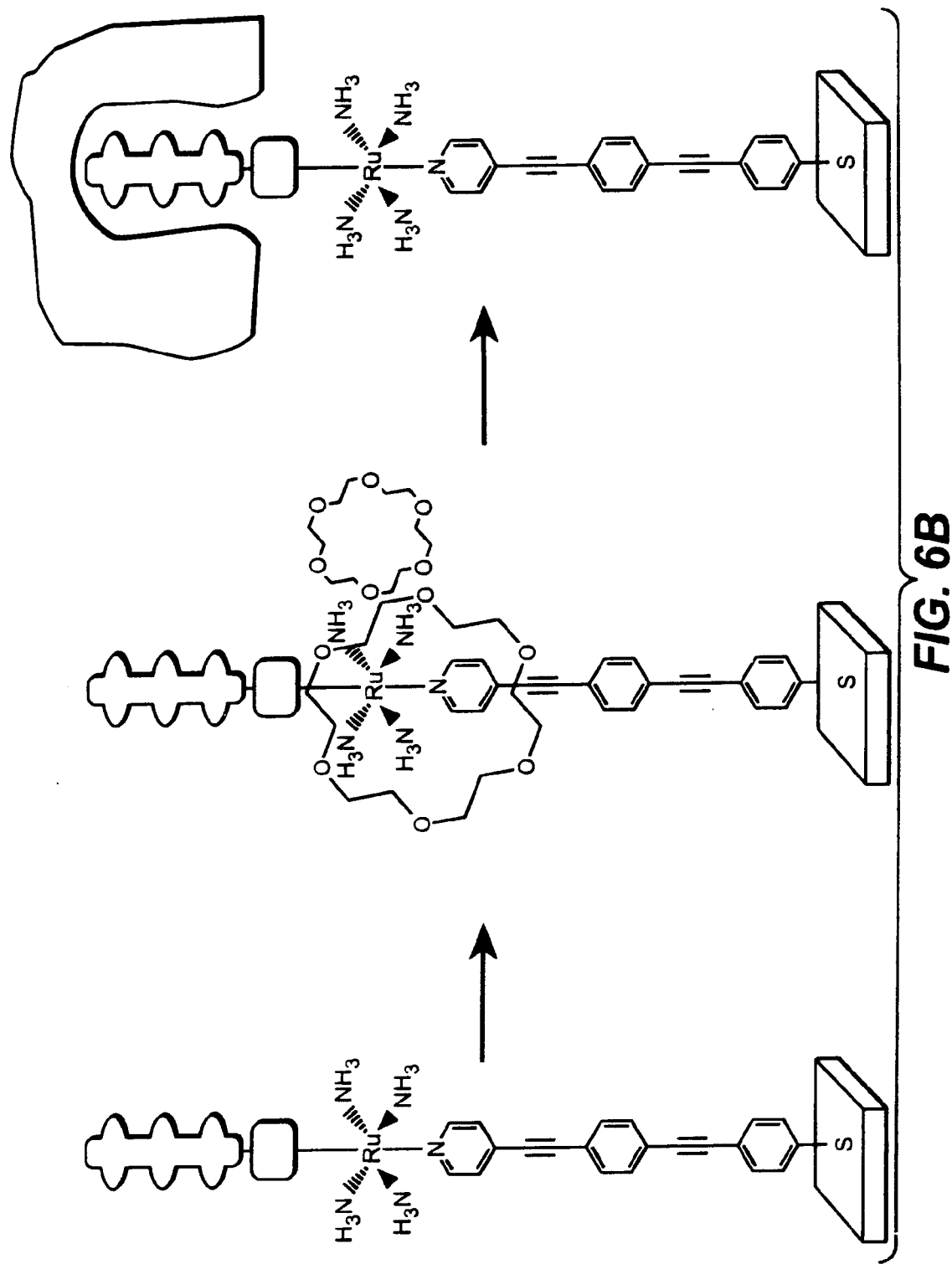
FIG. 6B depicts the use of crown ether coordination to enhance potential shift.
Figure 7:
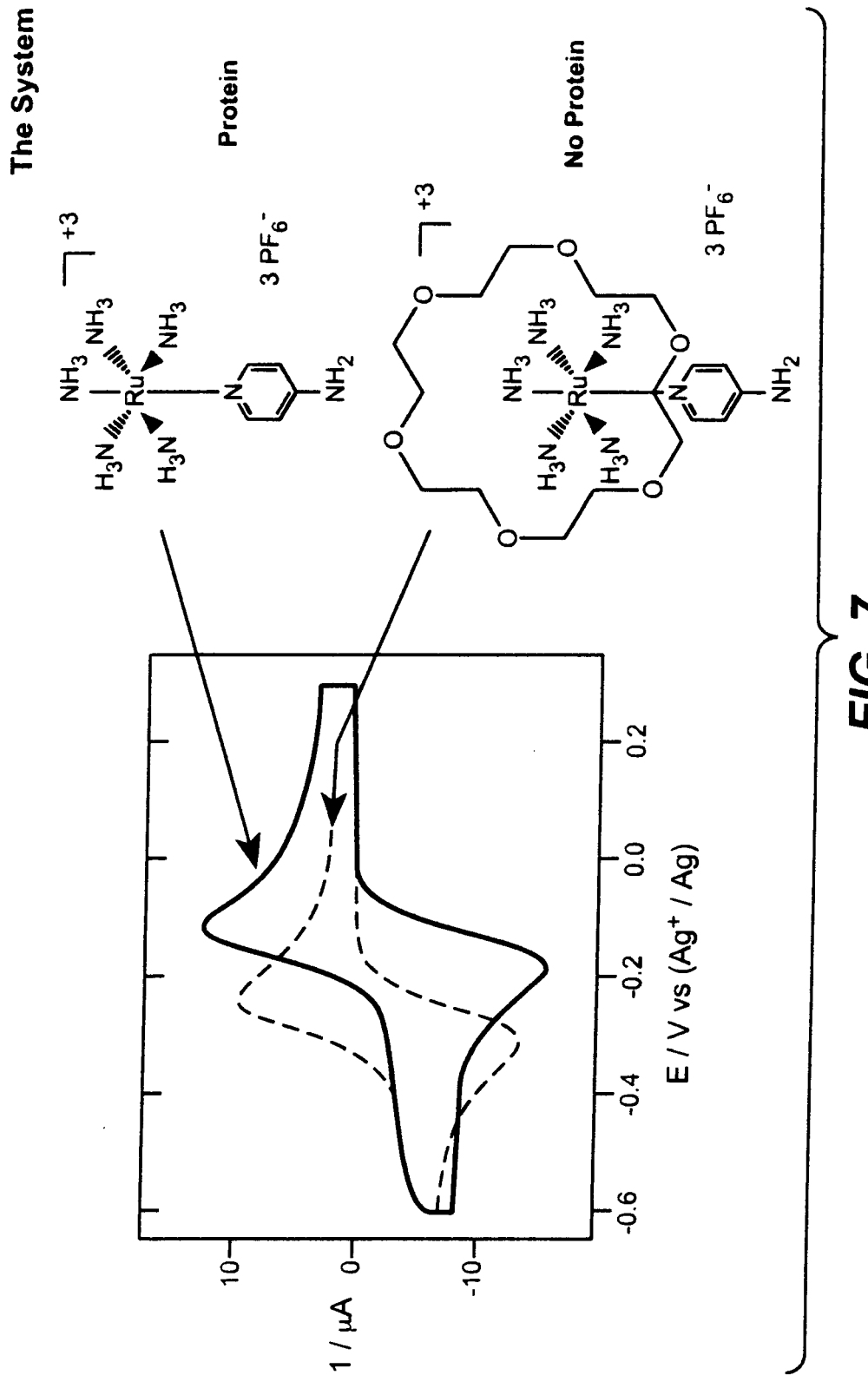
FIG. 7 depicts the effect of second-sphere coordination, the adduct formation between Ru(NH$_3$)$_5$L and 18-C-6.

Without being bound by theory, the reason for the increased potential shift is likely the following: CEs form hydrogen bonds to surrounding water molecules. CEs are known to bind to alkali metal ions (e.g. $Na^+$, $K^+$ in electrolyte) which bind to the oxygen atoms of the CE. In water, the CE, the ion and the counterion (e.g. $Cl^-$) are hydrated with surrounding water molecules. Upon binding of the target to the capture ligand the water molecules surrounding the transition metal complex are replaced as well as the water molecules hydrating the CE, the alkali metal ion and the counterion of the alkali metal ion. See FIGS. 6A and 6B. The fact that many more water molecules are replaced will increase the shift in potential observed in a binding event. In some cases the change in environment from hydrophilic to more hydrophobic actually expels the alkali metal salt (such as $K^+$ and $Na^+$ ions) from the CE as well as the water molecules, and a potential shift of as much as 1.0V can be expected. Electrochimica acta 2001, 2733, herein incorporated by reference. See. e.g. FIG. 7. Some of the examples are:

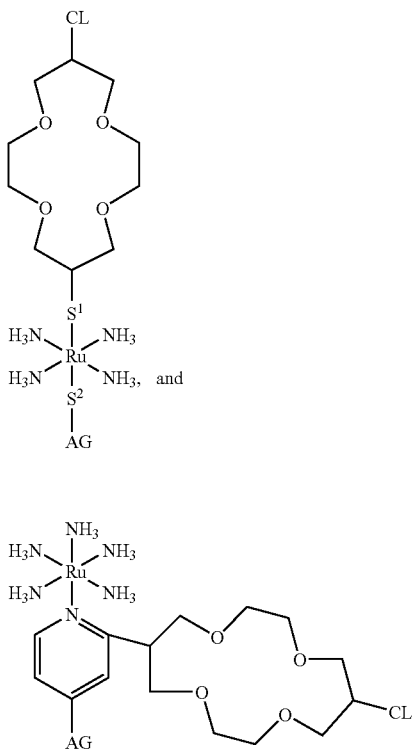

wherein $S^1$ and $S^2$ are spacers, CL=capture ligand and AG=anchoring group.

8). Pyridine-Thioether/Ether-Ligands

In some embodiments, pyridine-thioether/ether-ligands are used in the synthesis of EAM. These ligand systems will be able to bind to various metal centers via the pyridine-nitrogen and the thioether/ether functionality. Without being bound by the theory, there is the possibility that upon binding of the EAM to the target, the metal-thioether/ether bond is getting cleaved and e.g. halide binds to the metal center, which would be an inner-sphere effect, leading to a large shift in the electrochemical potential.

One of the examples for such complexes is shown below:

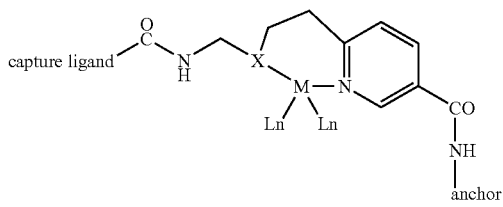

where Ln=coordinate ligand of metal center, L=0 or 1, and X=O or S;

In some embodiments, bipyridines and other multidentate-nitrogen-based ligands, such as 1,10 phenanthrolines or terpyridines, are used. Examples for these type of ligands are shown bellow:

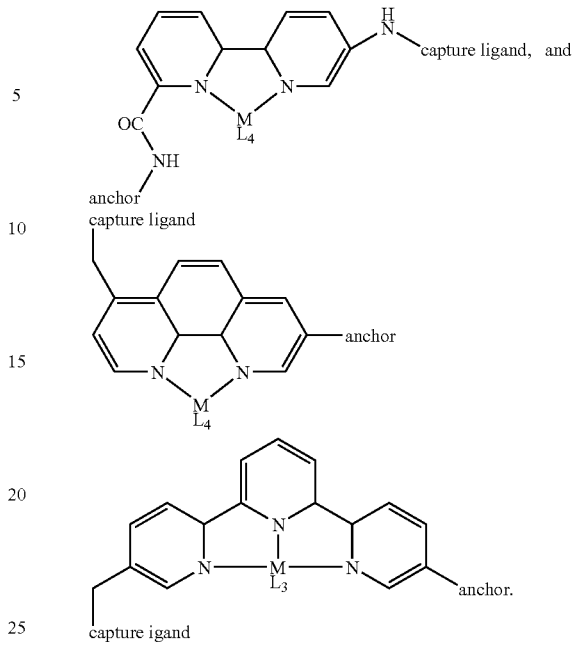

D. Spacer Groups in some embodiments the EAM or ReAMC is covalently attached to the anchor group (which is attached to the electrode) via an attachment linker or spacer ("Spacer 1"), that further generally includes a functional moiety that allows the association of the attachment linker to the electrode. See for example U.S. Pat. No. 7,384,749, incorporated herein by reference in its entirety and specifically for the discussion of attachment linkers). It should be noted in the case of a gold electrode, a sulfur atom can be used as the functional group (this attachment is considered covalent for the purposes of this invention). By "spacer" or "attachment linker" herein is meant a moiety which holds the redox active complex off the surface of the electrode. In some embodiments, the spacer is a conductive oligomer as outlined herein, although suitable spacer moieties include passivation agents and insulators as outlined below. In some cases, the spacer molecules are SAM forming species. The spacer moieties may be substantially non-conductive, although preferably (but not required) is that the electron coupling between the redox active molecule and the electrode ($H_{AB}$) does not limit the rate in electron transfer.

In addition, attachment linkers can be used to between the coordination atom of the capture ligand and the capture ligand itself, in the case when ReAMCs are utilized. Similarly, attachment linkers can be branched, such as shown in FIGS. 12-14. In addition, attachment linkers can be used to attach capture ligands to the electrode when they are not associated in a ReAMC.

One end of the attachment linker is linked to the EAM/ReAMC/capture ligand, and the other end (although as will be appreciated by those in the art, it need not be the exact terminus for either) is attached to the electrode.

The covalent attachment of the conductive oligomer containing the redox active molecule (and the attachment of other spacer molecules) may be accomplished in a variety of ways, depending on the electrode and the conductive oligomer used. See for example Structures 12-19 and the accompanying text in U.S. Patent Publication No. 20020009810, hereby incorporated by reference in its entirety.

In general, the length of the spacer is as outlined for conductive polymers and passivation agents in U.S. Pat. Nos. 6,013,459, 6,013,170, and 6,248,229, as well as U.S. Pat. No. 7,384,749 all herein incorporated by reference in their entireties. As will be appreciated by those in the art, if the spacer becomes too long, the electronic coupling between the redox active molecule and the electrode will decrease rapidly.

E. Capture Ligands

A variety of molecules can be used in the present invention as capture ligands. By "capture ligand" or "binding ligand" or "capture binding ligand" or "capture binding species" or "capture probe" herein is meant a compound that is used to probe for the presence of the target analyte that will bind to the target analyte. Generally, the capture ligand allows the attachment of a target analyte to the electrode, for the purposes of detection. As is more fully outlined below, attachment of the target analyte to the capture probe may be direct (i.e. the target analyte binds to the capture ligand) or indirect (one or more capture extender ligands are used). By "covalently attached" herein is meant that two moieties are attached by at least one bond, including sigma bonds, pi bonds and coordination bonds.

In some embodiments, the binding is specific, and the capture ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding which is not highly specific; for example, the systems may use different capture ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. This binding should be sufficient to remain bound under the conditions of the assay, including wash steps to remove non-specific binding. Generally, the disassociation constants of the analyte to the binding ligand will be in the range of at least $10^{-4}$-$10^{-6}$ $M^{-1}$, with a preferred range being $10^{-5}$ to $10^{-9}$ $M^{-1}$ and a particularly preferred range being $10^{-7}$-$10^{-9}$ $M^{-1}$.

As will be appreciated by those in the art, the composition of the capture ligand will depend on the composition of the target analyte. Capture ligands to a wide variety of analytes are known or can be readily found using known techniques. For example, when the analyte is a single-stranded nucleic acid, the capture ligand may be a complementary nucleic acid. Similarly, the analyte may be a nucleic acid binding protein and the capture binding ligand is either single-stranded or double stranded nucleic acid; alternatively, the binding ligand may be a nucleic acid-binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates and inhibitors. As will be appreciated by those in the art, any two molecules that will associate may be used, either as an analyte or as the binding ligand. Suitable analyte/binding ligand pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-binding ligand pairs. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors.

As described herein, the capture ligand can be attached to the coordinating ligand and/or anchor via a covalent bond. The method of attachment of the capture binding ligand will generally be done as is known in the art, and will depend on the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or through the use of a linker, sometimes depicted herein as "Z". Linkers are known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred. Z may also be a sulfone group, forming sulfonamide.

In this way, capture binding ligands comprising proteins, lectins, nucleic acids, small organic molecules, carbohydrates, etc. can be added.

In some embodiment, antibodies or a fragment thereof are used as capture ligands. By "antibody" herein is meant a member of a family of glycosylated proteins called immunoglobulins, which can specifically combine with an antigen. The term "antibody" includes full-length as well antibody fragments, as are known in the art, including Fab, Fab2, single chain antibodies (Fv for example), chimeric antibodies, humanized and human antibodies, etc., either produced by the modification of whole antibodies or those synthesized de novo using recombinant DNA technologies, and derivatives thereof.

However, in some embodiments, whole antibodies are not preferred. This is because antibodies could be too bulky, leads to interference with transducer. Thus in some embodiments, antibody fragments and mimitopes are used as capture ligands.

By "epitope" herein is meant the actual site of antibody recognition of the antigen. The term is also used interchangeably with "antigenic determinant" or "antigenic determinant site".

By "mimitopes" or "mimotope" herein is meant a peptide which has the spatial structure of a biologically important site, e.g., an epitope, or an enzyme active site, or a receptor binding site.

In some embodiments, the capture ligand comprises antibody alternatives, including but not limited to avimer. By "avimer" herein is meant proteins that are evolved from a large family of human extracellular receptor domains by in vitro exon shuffling and phage display. It is generally a multidomain protein with binding and inhibitory properties. See Silverman et al., Nature Biotechnology 23:1556-1561 (2005), herein incorporated by reference.

In some embodiments, the capture ligand comprises oligomeric peptides. These peptides can be obtained using techniques known in the art, including but not limited to phage display, Sidhu et al., Methods Enzymol., 328, 333-363 (2000), and one bead one peptide. For example, the peptide can be obtained using Biopanning. Giodano et al., Nat. Med. 7:1249-53 (2001); herein incorporated by reference.

The capture ligand may be nucleic acid, when the target analyte is a nucleic acid or nucleic acid binding proteins; alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly, there is a wide body of literature relating to the development of binding partners based on combinatorial chemistry methods. In this embodiment, when the capture ligand is a nucleic acid, preferred compositions and techniques are outlined in PCT US97/20014, hereby incorporated by reference.

In some embodiments, the capture ligand comprises an aptamer. By "aptamer" herein is meant a single-stranded, partially single-stranded, partially double-stranded or double-stranded nucleotide sequence, advantageously a replicatable nucleotide sequence, capable of specifically recognizing a selected nonoligonucleotide molecule or group of molecules by a mechanism other than Watson-Crick base pairing or triplex formation. Aptamers disclosed herein include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Aptamers of the invention include partially and fully single-stranded and double-stranded nucleotide molecules and sequences, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the aptamer molecule or sequence. Aptamers can specifically bind to soluble, insoluble or immobilized selected molecules (e.g., ligands, receptors and effector molecules). Alternatively, the term "aptamer" includes nucleotides capable of shape-specific recognition of chemically bland surfaces by a mechanism distinctly different from specific binding. Aptamers of the instant invention may be selected to specifically recognize a structural shape or surface feature comprising a chemically bland surface (e.g., a silicon chip or carbon nanostructure) rather than the chemical identity of a selected target molecule (e.g., a ligand or receptor). An aptamer may be a molecule unto itself or a sequence segment comprising a nucleotide molecule or group of molecules, e.g., a defined sequence segment or aptameric sequence comprising a synthetic heteropolymer, multivalent heteropolymeric hybrid structure or aptameric multimolecular device.

IV. Method of Making the Compositions of the Invention

As will be appreciated by those in the art, the compositions can be made using a variety of techniques known in the art. See for example the disclosures of U.S. Pat. Nos. 6,013,459, 6,248,229, 7,018,523, 7,267,939, U.S. patent application Ser. Nos. 09/096,593 and 60/980,733, and U.S. Provisional Application titled "Electrochemical Assay for the Detection of Enzymes" which is filed concurrently with the present application, particularly for teachings associated with synthesis.

Figure 3:
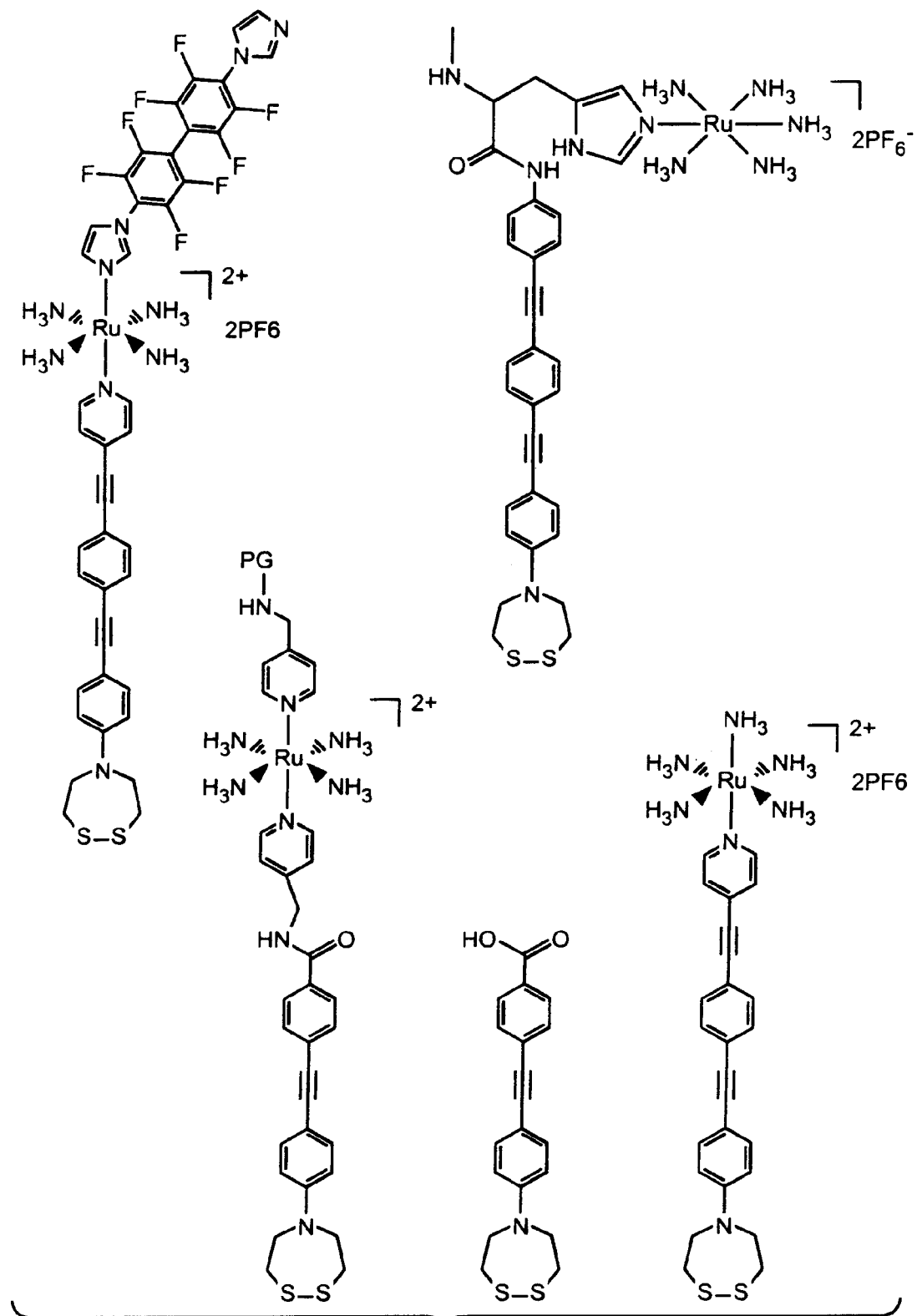
FIG. 3 depicts BIPOD based compounds.

In one embodiment, the compositions of the invention are made as depicted in FIG. 3. In this embodiment, the electrodes comprising a species including a functional group for the attachment of the capture ligand is used, and after the composition is made, a capture ligand with a complementary functional group is added, resulting in essentially spontaneous addition of the capture ligand to the surface. As will be appreciated by those in the art, there are a wide variety of functional groups/complementary functional groups that can be used. Suitable functional groups include, but are not limited to, maleimide, imidoesters, N-hydroxysuccinimidyls, alkyl halides, aryl halides, alpha-haloacyls and pryidyl disulfides. In general, the corresponding/complementary functional groups sulfhydryls, amines, amines, sulfhydryls, sulfhydryls, sulfhydryls and sulfhydryls, respectively. As will be appreciated by those in the art, it is also possible to switch the orientation of these functional groups, e.g. the sulfhydryl is present on the attachment linker and the maleimide is added to the biomolecule to be used as the capture ligand.

As noted herein, the methods of attaching are dependent upon the reactive groups present on the two components. In an exemplary embodiment, the reactive functional group of the haptens of the invention and the functional group of the reactive part comprise electrophiles and nucleophiles that can generate a covalent linkage between them. Alternatively, the reactive functional group comprises a photoactivatable group, which becomes chemically reactive only after illumination with light of an appropriate wavelength. Typically, the conjugation reaction between the reactive functional group and the reactive partner results in one or more atoms of the reactive functional group or the reactive partner being incorporated into a new linkage attaching the two components. Selected examples of functional groups and linkages are shown in Table 1, where the reaction of an electrophilic group and a nucleophilic group yields a covalent linkage.

TABLE 1

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |

TABLE 1-continued

Examples of some routes to useful covalent linkages
with electrophile and nucleophile reactive groups

| Electrophilic Group | Nucleophilic Group | Resulting Covalent Linkage |
|---|---|---|
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates The functional groups and complementary functional groups can also include linkers, for flexibility or steric rigidity as the case may be, or other reasons.

It should be noted that while the figures depict the presence of a functional group and the complementary functional group, in some cases the addition results in the loss of atoms from these groups, and thus this is not meant to depict a situation when the entire functional group and complementary functional group is present in the final composition.

In addition, the figures depict the use of "monofunctional" linkers, e.g. a maleimide. It is also possible to include additional steps that utilize either homo- or heterobifunctional groups, (see 1994 Pierce Chemical Company catalog, technical section on cross linkers, pages 155-200, incorporated herein by reference). For example, an attachment linker comprising a sulfur atom on one terminus and an amino group on the other end could be reacted with a bifunctional linker that reacts with amines, and then subsequently a capture ligand comprising an amino group can be added.

Figure 8A:
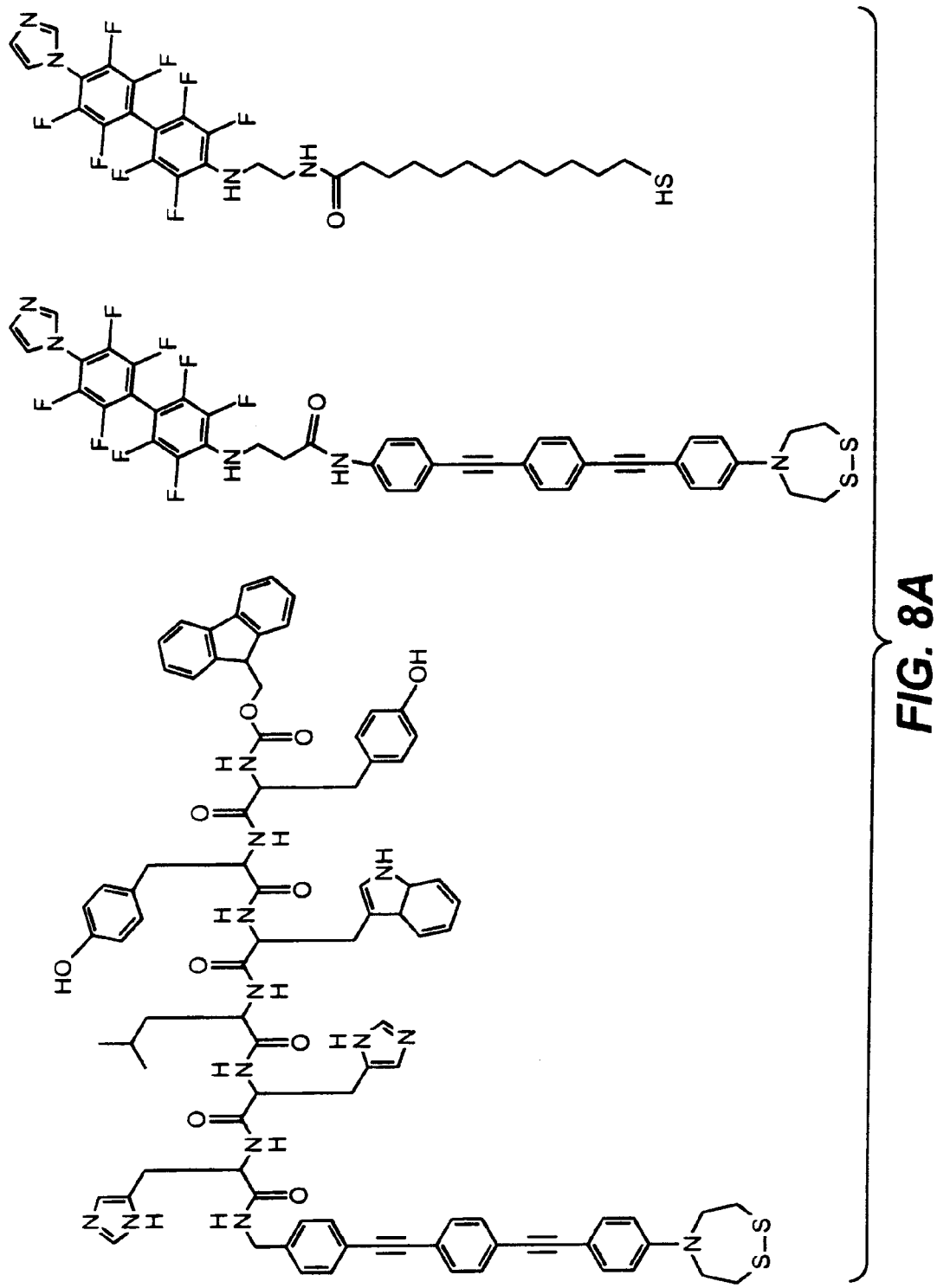
FIGS. 8A and 8B depict ligands used in the "single" and "side-by-side" arrangement when multiple metals are used.
Figures 1, 8B:
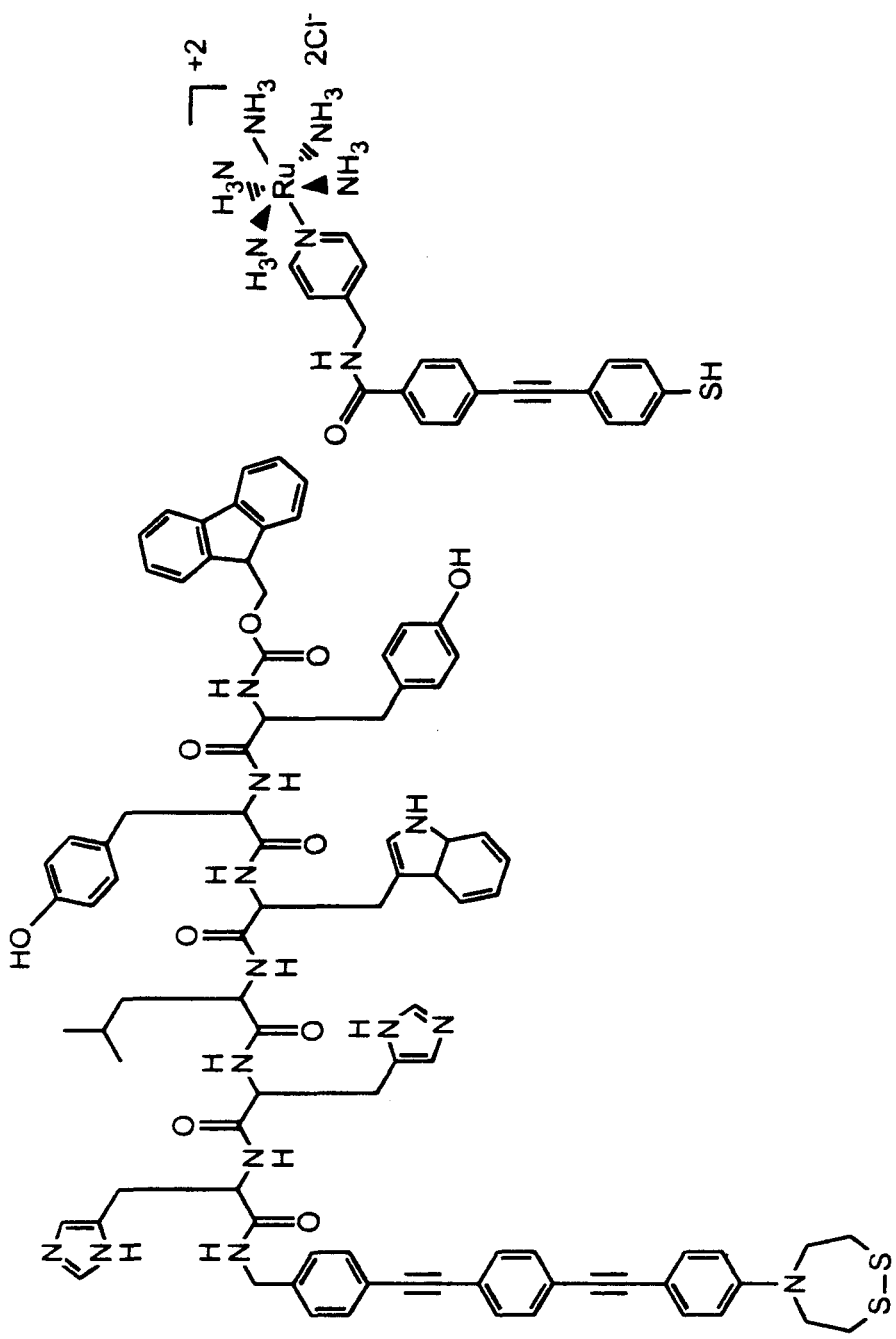
Figures 2, 8B:
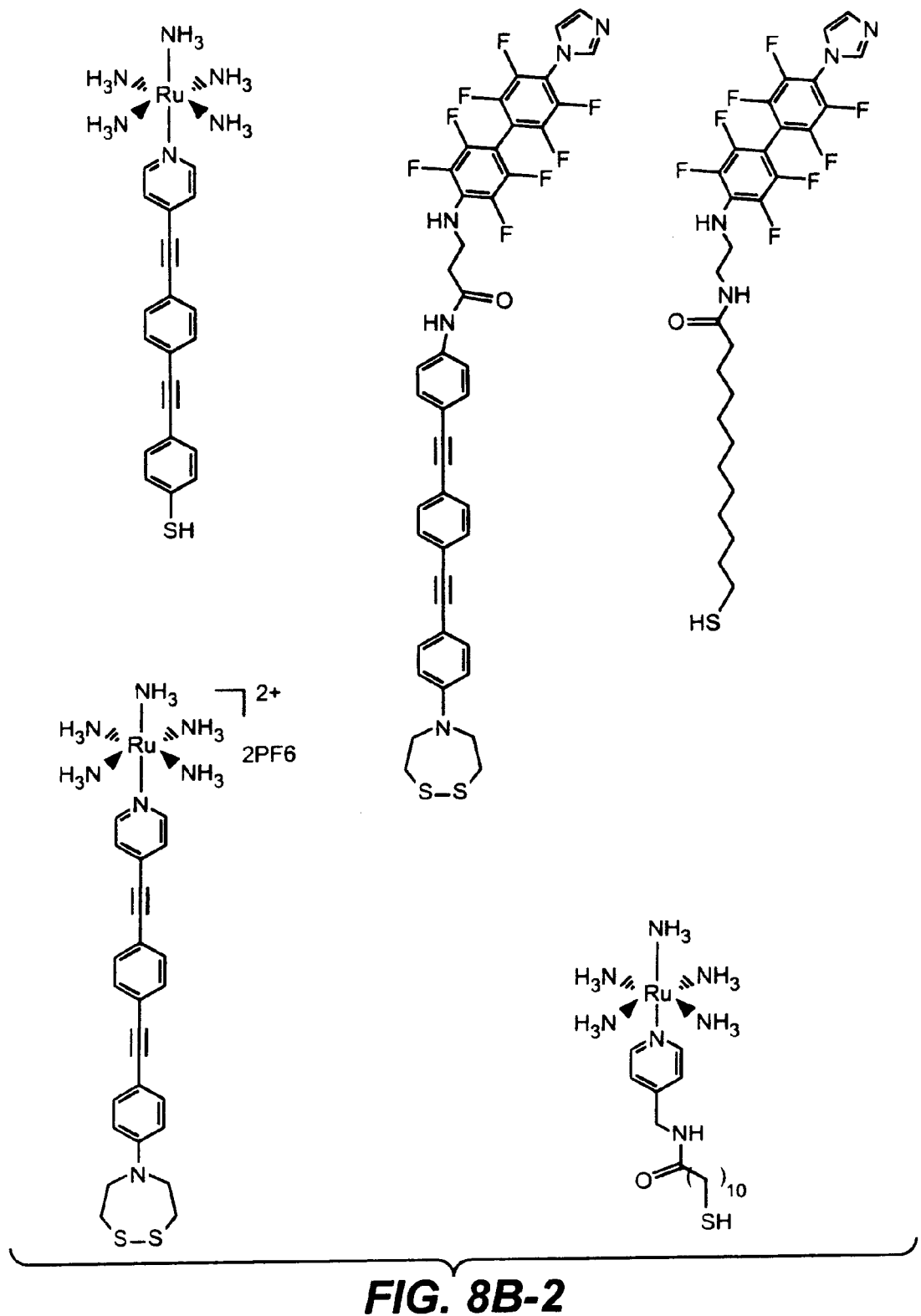
Figure 9B:
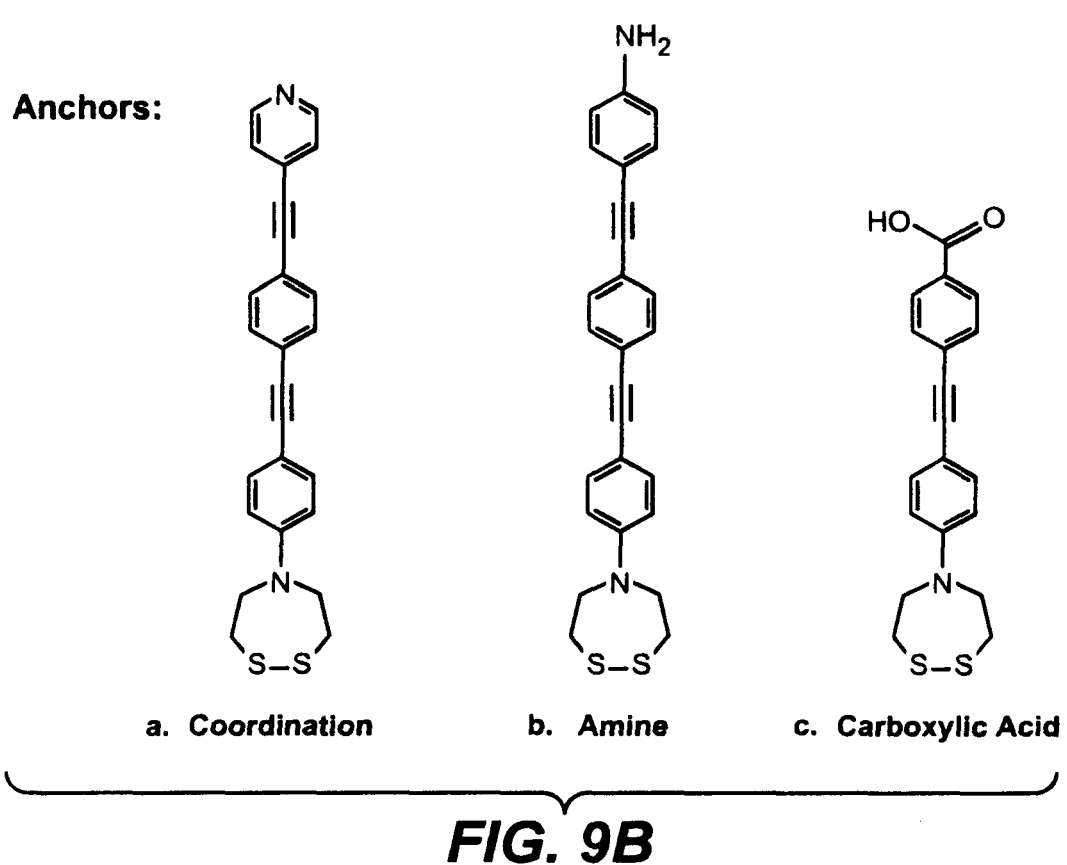
FIG. 9 depicts some of the building blocks for generating the compound for detection of analyte.
Figure 11:
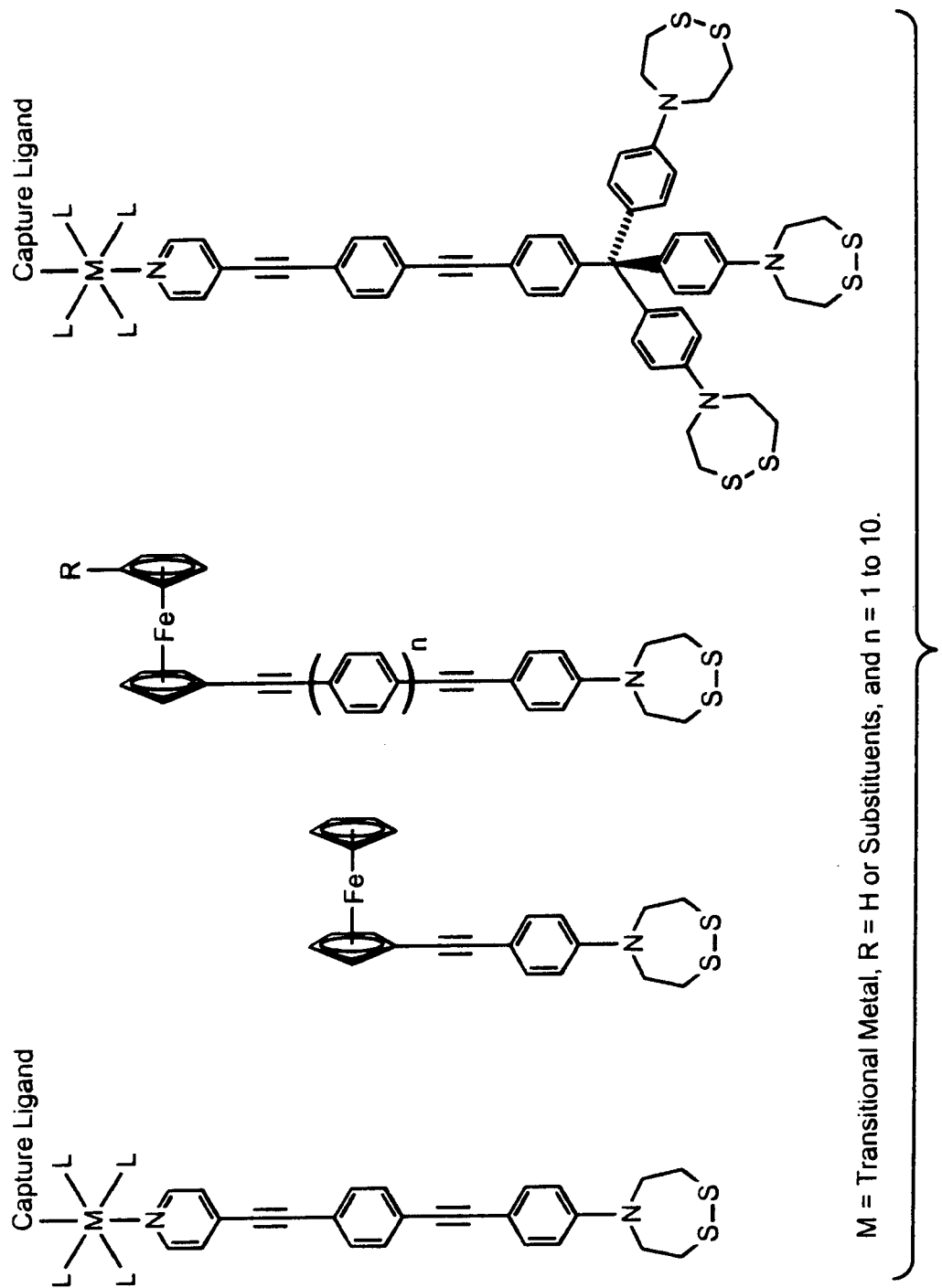
FIG. 11 depicts some exemplary compounds.

In another embodiment, the compositions of the invention are made by synthesizing each component and adding them to the electrode, generally simultaneously. That is, in the embodiment of FIG. 12A, for example, the REAMC comprising the attachment linker (with the attachment functional moiety such as a sulfur atom), the ligands, the transition metal and the binding ligand is made, and added (optionally with a SAM forming species) to the electrode. Similarly, a two or three component system is done in FIG. 1B, with a first species comprising the EAM with the attachment linker and attachment functional group, a second species comprising an attachment linker with the capture ligand, and the optional third species of a SAM forming species, which are added, against generally simultaneously, to the electrode. In some cases, the components can be added sequentially, and in some cases, a post synthesis step done of adding extra SAM forming species (and/or other components) with optional heating can be done to ensure good packing on the electrode.

In some embodiments, the ligands can have functionalities that allow the anchor and capture ligand to be added to it after the metal complex is formed.

In some embodiments, the compound is synthesized stepwise. Thus, the capture ligand and the anchor are added to the ligand of the EAM sequentially.

In some embodiments, the capture ligand and the anchor are added to the EAM concomitantly.

In some embodiments, "clip" are added to the EAM first and the capture ligand and anchor groups are added to the "clips" later. By "clips" herein is meant a group or moiety that can be attached to an EAM covalently, and on to which the capture ligand and/or the anchor group could be added.

One of the clips is shown below:

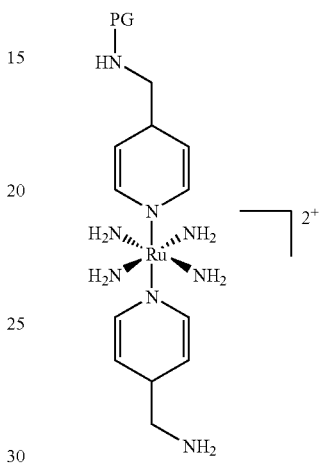

wherein PG=protection group.

In some embodiments, wherein pentaammine is used as coordinating ligands, the capture ligand can be added first, and the anchor group is added to the capture ligand.

The compositions of the present invention may be used in a variety of research, clinical, quality control, or field testing settings.

The examples provided herein are for illustration purposes only and are in no means to limit the scope the present invention. Further, all references cited herein are incorporated by reference for all the relevant contents therein.

V. Method of Using the Composition of the Invention

A. Target Analyte and Sample

In one aspect, the present invention provides methods and compositions useful in the detection of target analytes. By "target analyte" or "analyte" or grammatical equivalents herein is meant any molecule or compound to be detected and that can bind to a binding species, e.g. a capture ligand, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs, cells; antibodies; antigens; cellular membrane antigens and receptors (neural, hormonal, nutrient, and cell surface receptors) or their ligands.

In some embodiments, the target analyte is cytochrome P450, avidin/streptavdin, SEB, PSA-(protease), tryprin/chymotrypin (protease), anthrax spore and *E. coli.* O157:H7.

In some embodiments, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures, The side chains may be in either the (R) or the (S) configuration. In a preferred embodiment, the amino acids are in the (S) or L-configuration. As discussed below, when the protein is used as a capture ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio,* e.g. *V. cholerae; Escherichia,* e.g. Enterotoxigenic *E. coli, Shigella,* e.g. *S. dysenteriae; Salmonella,* e.g. *S. typhi; Mycobacterium* e.g. *M. tuberculosis, M. leprae; Clostridium,* e.g. *C. botulinum, C. tetani, C. difficile, C. perfringens; Cornyebacterium,* e.g. *C. diphtheriae; Streptococcus, S. pyogenes, S. pneumoniae; Staphylococcus,* e.g. *S. aureus; Haemophilus,* e.g. *H. influenzae; Neisseria,* e.g. *N. meningitidis, N. gonorrhoeae; Yersinia,* e.g. *G. lamblia Y. pestis, Pseudomonas,* e.g. *P. aeruginosa, P. putida; Chlamydia,* e.g. *C. trachomatis; Bordetella,* e.g. *B. pertussis; Treponema,* e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone; and (4) other proteins (including α-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

As will be appreciated by those in the art, a large number of analytes may be detected using the present methods; basically, any target analyte for which a binding ligand, described below, may be made may be detected using the methods of the invention.

In some embodiments, the target analyte is a protein related to MRSA. Methicillin-resistant *Staphylococcus aureus* (MRSA) (also be referred to as multiple-resistant *Staphylococcus aureus* or oxacillin-resistant *Staphylococcus aureus* (ORSA)) is responsible for difficult-to-treat infections in humans. MRSA is a strain of *Staphylococcus aureus* that is resistant to a large group of antibiotics called the beta-lactams, which include the penicillins and the cephalosporins.

The organism is often sub-categorized as Community-Associated MRSA (CA-MRSA) or Health Care-Associated MRSA (HA-MRSA) although this distinction is complex. Some have defined CA-MRSA by criteria related to patients suffering from an MRSA infection while other authors have defined CA-MRSA by genetic characteristics of the bacteria themselves. CA-MRSA strains were first reported in the late 1990s; these cases were defined by a lack of exposure to the health care setting. In the next several years, it became clear that CA-MRSA infections were caused by strains of MRSA that differed from the older and better studied healthcare-associated strains. The new CA-MRSA strains have rapidly spread in the United States to become the most common cause of cultured skin infections among individuals seeking medical care for these infections at emergency rooms in cities. These strains also commonly cause skin infections in athletes, jail and prison detainees, soldiers, Native Alaskans and Native Americans, and children in the inner city.

MRSA is a resistant variation of the common bacterium *Staphylococcus aureus*. It has evolved an ability to survive treatment with beta-lactamase resistant beta-lactam antibiotics, including methicillin, dicloxacillin, nafcillin, and oxacillin. MRSA is especially troublesome in hospital-associated (nosocomial) infections. In hospitals, patients with open wounds, invasive devices, and weakened immune systems are at greater risk for infection than the general public. Hospital staff who do not follow proper sanitary procedures may transfer bacteria from patient to patient. Visitors to patients with MRSA infections or MRSA colonization are advised to follow hospital isolation protocol by using the provided gloves, gowns, and masks if indicated. Visitors who do not follow such protocols are capable of spreading the bacteria to cafeterias, bathrooms, and elevators.

In some embodiment, the MRSA related protein is penicillin binding protein 2a (PBP2a). PBP2' is a protein coded by the mecA gene and is present in the membranes of methicillin resistant *Staphylococcus aureus* and coagulase-negative staphylococci. The preparation of PBP2' can be carried out using methods known in the art, such as the protocol described in the MRSA Latex Test for PBP2' kit distributed by Hardy Diagnostics (Santa Maria, Calif.).

In some embodiments, the target is the PBP2a protein of MRSA, and the capture ligand is a moiety that is capable of binding to PBP2a.

By "nucleic acid" or "oligonucleotide" or grammatical equivalents herein is meant at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37.743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or EAM attachment, an analog structure may be used. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

In some embodiments, nucleic acid target analytes are not preferred.

In general, a sample is added to the compositions of the invention. In one aspect, the present invention provides a method of detecting a target enzyme in a sample. By "sample" or "test sample" herein is meant a composition that contains the analyte or analytes to be detected. The sample can be heterogeneous, containing a variety of components, i.e. different proteins. Alternatively, the sample can be homogenous, containing one component. The sample can be naturally occurring, a biological material, or man-made material. The material can be in a native or denatured form. The sample can be a single cell or a plurality of cells, a blood sample, a tissue sample, a skin sample, a urine sample, a water sample, or a soil sample. In some embodiments, the sample comprises the contents of a single cell, or the contents of a plurality of cells. The sample can be from a living organism, such as a eukaryote, prokaryote, mammal, human, yeast, or bacterium, or the sample can be from a virus. The samples can be used without any treatment, or with treatment if desired.

In some embodiments, the target analyte, contained within a test sample, is added to the compositions of the invention, under conditions that if present, the target analyte binds to the capture binding ligand. These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

As will be appreciated by those in the art, a large number of analytes may be detected using the present methods; basically, any target analyte for which a capture ligand, described below, may be made may be detected using the methods of the invention.

In addition, those in the art will appreciate that it is also possible to use the compositions of the invention in assays that rely on a loss of signal. For example, a first measurement is taken when the redox active molecule is inhibited, and then the system is changed as a result of the introduction of a target analyte, causing the solvent inhibited molecule to become solvent accessible, resulting in a loss of signal. This may be done in several ways, as will be appreciated by those in the art.

In some embodiments, a first measurement is taken when the target analyte is present. The target analyte is then removed, for example by the use of high salt concentrations or thermal conditions, and then a second measurement is taken. The quantification of the loss of the signal can serve as the basis of the assay.

Alternatively, the target analyte may be an enzyme. In this embodiment, the redox active molecule is made solvent inhibited by the presence of an enzyme substrate or analog, preferably, but not required to be covalently attached to the redox active molecule, preferably as one or more ligands. Upon introduction of the target enzyme, the enzyme associates with the substrate to cleave or otherwise sterically alter the substrate such that the redox active molecule is made solvent accessible. This change can then be detected. This embodiment is advantageous in that it results in an amplification of the signal, since a single enzyme molecule can result in multiple solvent accessible molecules. This may find particular use in the detection of bacteria or other pathogens that secrete enzymes, particularly scavenger proteases or carbohydrases.

In some embodiments, the target analyte is a protease. Proteases are classified into six groups: serine proteases, threonine proteases, cysteine proteases, aspartic acid proteases, metalloproteases, and glutamic acid proteases. In general, protease can either break specific peptide bonds (e.g. specific segments for limited proteolysis), depending on the amino acid sequence of a protein, or break down a complete protein to amino acids (unlimited proteolysis). The activity can be a destructive change, abolishing a protein's function or digesting it to its principal components; it can be an activation of a function, or it can be a signal in a signaling pathway.

In some embodiments, the target enzyme is an endopeptidase. By "endopeptidase" herein is meant peptidases that break peptide bonds within a protein substrate, in contrast to exopeptidases, which break peptide bonds from one or both termini of the protein substrate. Endopeptidases are divided into subclasses on the basis of catalytic mechanism: the serine endopeptidases, cysteine endopeptidases, aspartic endopeptidases, metalloendopeptidases, and other endopeptidases.

(1). Serine Endopeptidases

This class comprises two distinct families. The chymotrypsin family which includes the mammalian enzymes such as chymotrypsin, trypsin or elastase or kallikrein and the subtilisin family which include the bacterial enzymes such as subtilisin. The general three dimensional (3D) structure is different in the two families but they have the same active site geometry and the catalysis proceeds via the same mechanism. The serine endopeptidases exhibit different substrate specificities which are related to amino acid substitutions in the various enzyme subsites interacting with the substrate residues. Some enzymes have an extended interaction site with the substrate whereas others have a specificity restricted to the P1 substrate residue.

(2). Cysteine Endopeptidases

This family includes the plant proteases such as papain, actinidin or bromelain, several mammalian cathepsins, including lysosomal cathepsins and cathepsin B, L, S, H, J, N and O; the cytosolic calpains (calcium-activated) as well as several parasitic proteases (e.g., *Trypanosoma*, *Schistosoma*) and caspases, including interleukin converting enzyme (ICE).

(3). Aspartic Endopeptidases

Most of aspartic endopeptidases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral endopeptidases such as the protease from the AIDS virus (HIV) also called retropepsin.

In contrast to serine and cysteine proteases, catalysis by aspartic endopeptidases do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage.

(4). Metallo Endopeptidases

The metallo endopeptidases are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Of particular interest are metalloenzymes including adenosine deaminase, angiotensin converting enzyme, calcineurin, metallo-beta-lactamase, PDE3, PDE4, PDE5, renal dipeptidase, and urease.

In one embodiment, the metallo endopeptidase is a matrix metalloproteinase, including MMP-1 through MMP-10, particularly MMP-1, MMP-2, MMP-7 and MMP-9.

(5). Bacterial/Toxin Endopeptidases

Toxin endopeptidases, usually of bacterial origin, can have a devastating and sometime lethal impact on host organisms. Some of the better known bacterial endopeptidase toxins are listed below in Table 1.

TABLE 1

| Bacterial Endopeptidases | | | |
| --- | --- | --- | --- |
| Organism/Toxin | Mode of Action | Target (Cleavage Site) | Disease |
| *B. anthracis*/lethal factor | Metalloprotease | MAPKK1/MAPKK2 (multiple) | Anthrax |
| *C. botulinum*/neurotxin A | Zinc-metalloprotease | SNAP-25 (ANQ/RAT) | Botulism |

TABLE 1-continued

Bacterial Endopeptidases

| Organism/Toxin | Mode of Action | Target (Cleavage Site) | Disease |
|---|---|---|---|
| C. botulinum/neurotxin B | Zinc-metalloprotease | VAMP/synaptobrevin (ASQ/FET) | Botulism |
| C. botulinum/neurotxin C | Zinc-metalloprotease | Syntaxin (TKK/AVK) | Botulism |
| C. botulinum/neurotxin D | Zinc-metalloprotease | VAMP/synaptobrevin (DQK/LSE) | Botulism |
| C. botulinum/neurotxin E | Zinc-metalloprotease | SNAP-25 (IDR/IME) | Botulism |
| C. botulinum/neurotxin F | Zinc-metalloprotease | VAMP/synaptobrevin | Botulism |
| C. botulinum/neurotxin G | Zinc-metalloprotease | VAMP/synaptobrevin (TSA/AKL) | Botulism |
| Yersinia virulence factor YopJ | Cysteine protease | Unknown | |
| Yersinia virulence factor YopT | Cysteine protease | Prenylated cysteine | |
| Salmonella virulence factor AvrA | Unknown | Unknown | Salmonellosis |
| Clostridium tetani/tetanus toxin | Zinc-metalloprotease | VAMP/synaptobrevin (ASQ/FET) | Tetanus |

The *C. botulinum* neurotoxins (BoNTs, serotypes A-G) and the *C. tetani* tetanus neurotoxin (TeNT) are two examples of bacterial toxins that are endopeptidases. BoNTs are most commonly associated with infant and food-borne botulism and exist in nature as large complexes comprised of the neurotoxin and one or more associated proteins believed to provide protection and stability to the toxin molecule while in the gut. TeNT, which is synthesized from vegetative *C. tetani* in wounds, does not appear to form complexes with any other protein components.

BoNTs are highly specific, zinc-dependent endoproteases that specifically cleave small proteins which control the docking of synaptic vesicles with the neural synaptic membrane. BoNT A and BoNT E specifically cleave the 25-kD synaptosomal-associated protein (SNAP-25) with BoNT A cleaves between residues Q197 and R198. SNAP-25 is a presynaptic plasma membrane protein involved in the regulation of neurotransmitter release. Two alternative transcript variants encoding different protein isoforms have been described for this gene in human, SNAP25A (GenBank Accession No. NP_003072) and SNAP25B (GenBank Accession No. NP_570824). BoNT C cleaves the membrane protein syntaxin and SNAP-25. BoNT B, D, F and G are specific for the intracellular vesicle-associated membrane-associated protein (VAMP, also termed synaptobrevin). See Schiavo et al., JBC 266:23784-87 (1995); Schiavo et al., FEBS Letters 335:99-103 (1993), herein are incorporated by reference in their entireties.

Several in vitro assays have been developed based on the cleavage of immobilized synthetic peptide substrates. Halls et al., J Clin Microbiol 34:1934-8 (1996); Witcome et al., Appl Environ Microbiol 65:3787-92 (1999), and Anne et al., Ana Biochem 291:253-61 (2001).

The BoNTs and TeNT are either plasmid encoded (TeNT, BoNTs/A, G, and possibly B) or bacteriophage encoded (BoNTs/C, D, E, F), and the neurotoxins are synthesized as inactive polypeptides of 150 kDa. BoNTs and TeNT are released from lysed bacterial cells and then activated by the proteolytic cleavage of an exposed loop in the neurotoxin polypeptide. Each active neurotoxin molecule consists of a heavy (100 kDa) and light chain (50 kDa) linked by a single interchain disulphide bond. The heavy chains of both the BoNTs and TeNT contain two domains: a region necessary for toxin translocation located in the N-terminal half of the molecule, and a cell-binding domain located within the C-terminus of the heavy chain. The light chains of both the BoNTs and TeNT contain zinc-binding motifs required for the zinc-dependent protease activities of the molecules.

The cellular targets of the BoNTs and TeNT are a group of proteins required for docking and fusion of synaptic vesicles to presynaptic plasma membranes and therefore essential for the release of neurotransmitters. The BoNTs bind to receptors on the presynaptic membrane of motor neurons associated with the peripheral nervous system. Proteolysis of target proteins in these neurons inhibits the release of acetylcholine, thereby preventing muscle contraction. BoNTs/B, D, F, and G cleave the vesicle-associated membrane protein and synaptobrevin, BoNT/A and E target the synaptosomal-associated protein SNAP-25, and BoNT/C hydrolyzes syntaxin and SNAP-25. TeNT affects the central nervous system and does so by entering two types of neurons. TeNT initially binds to receptors on the presynaptic membrane of motor neurons but then migrates by retrograde vesicular transport to the spinal cord, where the neurotoxin can enter inhibitory interneurons. Cleavage of the vesicle-associated membrane protein and synaptobrevin in these neurons disrupts the release of glycine and gamma-amino-butyric acid, which, in turn, induces muscle contraction. The contrasting clinical manifestations of BoNT or TeNT intoxication (flaccid and spastic paralysis, respectively) are the direct result of the specific neurons affected and the type of neurotransmitters blocked.

Of particular interest is BoNT/LC (serotype C), and specifically BoNTC/LC (as compared to other LC serotypes). First, BoNTC/LC poses a particularly significant bioterror threat because it has a long half-life inside human neuronal cells. Second, an in vitro assay for BoNTC/LC does not currently exist, probably because this LC protease appears to require membranes to function. In the neuronal cell environment, BoNTC/LC cleaves syntaxin, a membrane protein required for synaptic vesicle fusion to the presynaptic membrane.

Other examples include the *Yersinia* virulence factors YopJ and YopT, as well as *Salmonella* AvrA.

Other target analytes include, but are not limited to: coagulation factor levels (hemorrhagic or thrombotic conditions), fecal elastase (exocrine activity of the pancreas, e.g. in cystic fibrosis or chronic pancreatitis), PSA, VEGF and EGFR (tumor response in rectal cancer), MMP-9 (tumor marker of esophageal cancer and early stroke marker), MMP-13 (early stroke marker), cathepsin B (cancer), cathepsin G (emphysema, rheumatoid arthritis, inflammation), plasminogen activator (thrombosis, chronic inflammation, cancer), urokinase (cancer).

In some embodiments the target analyte is troponin (cardiac troponin I and T). Troponin is a complex of three regulatory proteins that is integral to muscle contraction in skeletal and cardiac muscle, but not smooth muscle. Troponin is found in both skeletal muscle and cardiac muscle, but the specific versions of troponin differ between types of muscle. Two subtypes of troponin (cardiac troponin I and T) are very sensitive and specific indicators of damage to the heart muscle (myocardium). They are measured in the blood to differentiate between unstable angina and myocardial infarction (heart attack) in patients with chest pain. A patient who had suffered from a myocardial infarction would have an area of damaged heart muscle and so would have elevated cardiac troponin levels in the blood.

Similarly, another embodiment utilizes competition-type assays. In this embodiment, the binding ligand is the same as the actual molecule for which detection is desired; that is, the binding ligand is actually the target analyte or an analog. A binding partner of the binding ligand is added to the surface, such that the redox active molecule becomes solvent inhibited, electron transfer occurs and a signal is generated. Then the actual test sample, containing the same or similar target analyte which is bound to the electrode, is added. The test sample analyte will compete for the binding partner, causing the loss of the binding partner on the surface and a resulting decrease in the signal.

A similar embodiment utilizes a target analyte (or analog) is covalently attached to a preferably larger moiety (a "blocking moiety"). The analyte-blocking moiety complex is bound to a binding ligand that binds the target analyte, serving to render the redox active molecule solvent inhibited. The introduction of the test sample target analyte serves to compete for the analyte-blocking moiety complex, releasing the larger complex and resulting in a more solvent accessible molecule.

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In a embodiment, the apparatus further comprises a processor capable of comparing the input signal and the output signal. The processor is coupled to the electrodes and configured to receive an output signal, and thus detect the presence of the target analyte.

B. Initiation

In one aspect, the present invention provides methods of detecting target analyte.

The target analyte, contained within a test sample, is added to the electrode containing either a solvent accessible redox active complex or a mixture of solvent accessible redox active molecules and capture ligands, under conditions that if present, the target analyte will bind to the capture ligand. These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, antimicrobial agents, etc., may be used. The mixture of components may be added in any order that provides for the requisite binding.

In some embodiments, the target analyte will bind the capture ligand reversibly, i.e. non-covalently, such as in protein-protein interactions of antigens-antibodies, enzyme-substrate (or some inhibitors) or receptor-ligand interactions.

In a preferred embodiment, the target analyte will bind the binding ligand irreversibly, for example covalently. For example, some enzyme-inhibitor interactions are considered irreversible. Alternatively, the analyte initially binds reversibly, with subsequent manipulation of the system which results in covalent attachment. For example, chemical cross-linking after binding may be done, as will be appreciated by those in the art. For example, peptides may be cross-linked using a variety of bifunctional agents, such as maleimidobenzoic acid, methyldithioacetic acid, mercaptobenzoic acid, S-pyridyl dithiopropionate, etc. Alternatively, functionally reactive groups on the target analyte and the binding ligand may be induced to form covalent attachments.

Upon binding of the analyte to the binding moiety, the solvent accessible redox active molecule becomes solvent inhibited. By "solvent inhibited redox active molecule" herein is meant the solvent reorganization energy of the solvent inhibited redox active molecule is less than the solvent reorganization energy of the solvent accessible redox active molecule. As noted above, this may occur in several ways. In some embodiments, the target analyte provides a coordination atom, such that the solvent accessible redox active molecule loses at least one, and preferably several, of its small polar ligands. Alternatively, in some embodiments, the proximity of the target analyte to the redox active molecule does not result in ligand exchange, but rather excludes solvent from the area surrounding the metal ion (i.e. the first or second coordination sphere) thus effectively lowering the required solvent reorganization energy.

In some embodiments, the required solvent reorganization energy decreases sufficiently to result in a decrease in the $E^0$ of the redox active molecule by at about 100 mV, with at least about 200 mV being preferred, and at least about 300-500 mV being particularly preferred.

In some embodiments, the required solvent reorganization energy decreases by at least 100 mV, with at least about 200 mV being preferred, and at least about 300-500 mV being particularly preferred.

In some embodiments, the required solvent reorganization energy decreases sufficiently to result in a rate change of electron transfer (kET) between the solvent inhibited redox active molecule and the electrode relative to the rate of electron transfer between the solvent accessible redox active molecule and the electrode. In a embodiment, this rate change is greater than about a factor of 3, with at least about a factor of 10 being preferred and at least about a factor of 100 or more being particularly preferred.

The determination of solvent reorganization energy will be done as is appreciated by those in the art. Briefly, as outlined in Marcus theory, the electron transfer rates (kET) are determined at a number of different driving forces (or free energy, $-\Delta G°$); the point at which the rate equals the free energy is the $\lambda$. This may be treated in most cases as the equivalent of the solvent reorganization energy; see Gray et al. Ann. Rev. Biochem. 65:537 (1996), hereby incorporated by reference.

The solvent inhibited redox active molecule, indicating the presence of a target analyte, is detected by initiating electron transfer and detecting a signal characteristic of electron transfer between the solvent inhibited redox active molecule and the electrode.

Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Preferably, initiation and detection is chosen to maximize the relative difference between the solvent reorganization energies of the solvent accessible and solvent inhibited redox active molecules.

C. Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock-in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capacitance) could be used to monitor electron transfer between the redox active molecules and the electrode. Finally, any system that generates a current (such as electron transfer) also generates a small magnetic field, which may be monitored in some embodiments.

In some embodiments, the system may be calibrated to determine the amount of solvent accessible redox active molecules on an electrode by running the system in organic solvent prior to the addition of target. This is quite significant to serve as an internal control of the sensor or system. This allows a preliminary measurement, prior to the addition of target, on the same molecules that will be used for detection, rather than rely on a similar but different control system. Thus, the actual molecules that will be used for the detection can be quantified prior to any experiment. Running the system in the absence of water, i.e. in organic solvent such as acetonitrile, will exclude the water and substantially negate any solvent reorganization effects. This will allow a quantification of the actual number of molecules that are on the surface of the electrode. The sample can then be added, an output signal determined, and the ratio of bound/unbound molecules determined. This is a significant advantage over prior methods.

It should be understood that one benefit of the fast rates of electron transfer observed in the compositions of the invention is that time resolution can greatly enhance the signal-to-noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, orders of magnitude improvements in signal-to-noise may be achieved.

Without being bound by theory, it appears that target analytes, bound to an electrode, may respond in a manner similar to a resistor and capacitor in series. Also, the $E^0$ of the redox active molecule can shift as a result of the target analyte binding. Furthermore, it may be possible to distinguish between solvent accessible and solvent inhibited redox active molecules on the basis of the rate of electron transfer, which in turn can be exploited in a number of ways for detection of the target analyte. Thus, as will be appreciated by those in the art, any number of initiation-detection systems can be used in the present invention.

In some embodiments, electron transfer is initiated and detected using direct current (DC) techniques. As noted above, the $E^0$ of the redox active molecule can shift as a result of the change in the solvent reorganization energy upon target analyte binding. Thus, measurements taken at the $E^0$ of the solvent accessible redox active molecule and at the $E^0$ of the solvent inhibited molecule will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to distinguish between solvent accessible and solvent inhibited redox active molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

D. Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

EXAMPLES

Example 1

Synthesis of Compounds

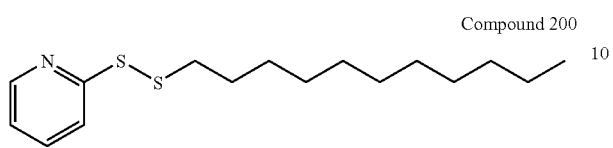
Compound 200

To a 100 mL round bottom flask was added 1-undecanethiol (1.4973 g, 7.95 mmol) and dry methanol (30 mL). Dry dichloromethane (5 mL) was added to aid in dissolution. 2,2-dithiodipyridine (1.7547 g, 7.96 mmol) was added as a powder followed by triethylamine (1.15 mL, 8.27 mmol). The reaction mixture was deoxygenated with argon then set to stir at room temperature under a positive pressure of argon for 24 hours. The reaction contents were dried on a rotary evaporator and purified by silica gel column chromatography using ethyl acetate/hexanes (1:1) as the eluent to yield compound 200 (1.8494 g, 78%).

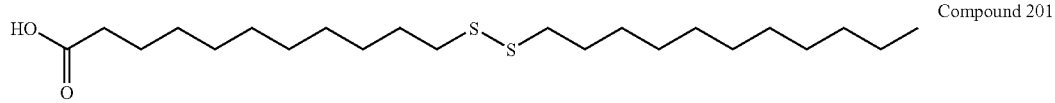 [SMILES: CCCCCCCCCCCSSCCCCCCCCCCC(=O)O]
Compound 201

To a 100 mL Schlenk flask was added 200 (1.8528 g, 6.23 mmol) with dry tetrahydrofuran (30 mL). 1-mercaptoundecanoic acid (1.5108 g, 6.92 mmol) and 4-dimethylaminopyridine (0.7710 g, 6.31 mmol) were added as solids to the reaction flask then additional tetrahydrofuran (20 mL). The reaction contents were deoxygenated with argon then set to stir at room temperature under a positive pressure of argon for 16 hours. The reaction contents were dried on a rotary evaporator and purified by silica gel column chromatography using methanol/dichloromethane (1:9) as the eluent to yield compound 201 (1.0207 g, 40%).

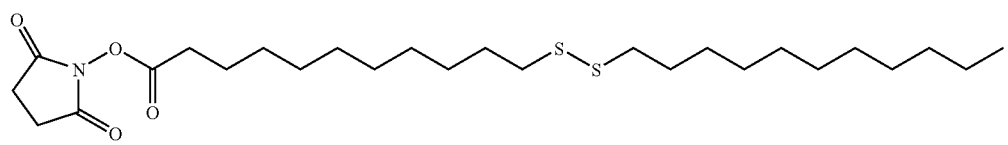
Compound 202

To a 250 mL round bottom flask was added N-hydroxysuccinimide (0.1435 g, 1.25 mmol) with dry dichloromethane (100 mL). The contents were briefly placed in a sonication bath to aid in dissolution then compound 201 (0.5078 g, 1.25 mmol) was added at once as a dichloromethane solution (10 mL). A dichloromethane solution (10 mL) of dicyclohexylcarbodiimide (0.2876 g, 1.39 mmol) was added drop wise over 23 min., followed by deoxygenation with bubbling argon for 30 min. The contents were set to stir at room temperature under a positive pressure of argon for 17 hours. The reaction contents were filtered to remove the dicyclohexylurea precipitate, concentrated on a rotary evaporator to 20-25 mL, then purified by silica gel column chromatography using methanol (2.5%) in dichlormethane as the eluent to provide compound 202 (0.3892 g, 62%).

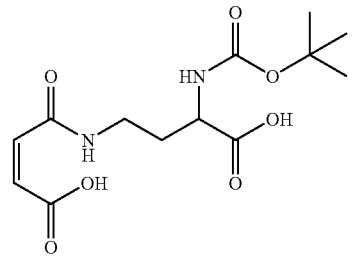
Compound 203

To a 25 mL round bottom flask was added Boc-D-2,4-diaminobutyric acid (0.3080 g, 1.41 mmol) and maleic anhydride (0.1415 g, 1.44 mmol) with glacial acetic acid (8 mL). The reaction contents were set to stir at room temperature under a positive pressure of argon for 4.5 hours. The reaction contents were dried on a vacuum line to remove all volatiles to yield compound 203 (0.4490 g). The material was used as-is without further purification; estimated purity is 65% based on $^1$H NMR data.

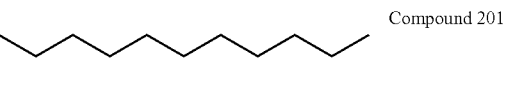
Compound 204

To a 100 mL Schlenk flask was added 203 (0.2919 g, 0.92 mmol) with dry toluene (40 mL) and triethylamine (400 µL, 2.89 mmol). The flask was fitted with a Dean-Stark apparatus and the side arm filled with dry toluene. The entire setup was flushed with argon and the flask brought to a vigorous reflux for 4.5 hours. The reaction contents were dried on a rotary evaporator to provide a tan/brownish oil. This oil was dissolved in water (20 mL) and acidified with citric acid (50 mL aqueous). Extraction of the crude product was accomplished with dichloromethane/methanol (9:1). The organic solution was concentrated on a rotary evaporator then purified by silica gel column chromatography using ethyl acetate/methanol (4:1)+trace acetic acid as the eluent to provide compound 204 (0.2647 g, 96%).

Compound 205

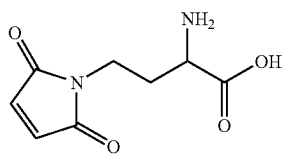

To a 25 mL round bottom flask was added HCl (10 mL of 4M in dioxane; 40 mmol) under argon. The contents were cooled in an ice water bath then transferred to a pre-cooled 25 mL round bottom flask containing compound 204. The contents were stirred at 0° C. under argon for 45 min. then warmed to room temperature and stirred for an additional 2 hours. All solvent and excess HCl was removed on a vacuum line and the crude residue passed through a Dowex 1X2-100 anion exchange resin using water as the eluent to provide compound 205 (0.2004 g, 98%).

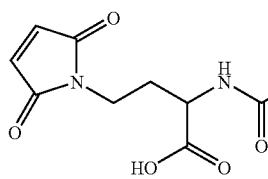

To a 50 mL Schlenk flask was added 202 (0.0220 g, 0.044 mmol) and dry acetonitrile (6 mL). 203 (0.0105 g, 0.045 mmol) and diisopropylethylamine (8.5 µL, 0.049 mmol) were added in sequence and the heterogeneous contents set to stir under argon at room temperature. After 30 min. additional diisopropylethylamine (8.5 µL, 0.049 mmol) was added to the reaction mixture to aid in the dissolution of 203. Dimethylacetamide (1.5 mL) was added drop wise to provide a homogeneous solution; the contents were flushed with argon and set to stir at room temperature for 17 hours. The reaction contents were pumped to dryness on a vacuum line then dissolved in dichloromethane and washed with aqueous citric acid. Extraction with dichloromethane (4×20 mL), followed by silica gel column chromatography using methanol/dichloromethane (1:9) yielded compound 206 (0.0114 g, 45%).

Compound 207

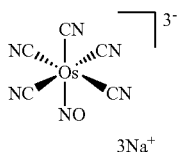

To a 15 mL quartz Schlenk tube was added potassium hexacyanoosmate (0.3052 g, 0.61 mmol) and sodium nitrite (0.8138 g, 11.8 mmol) with water (10 mL; pH=4, acetic acid) to give a homogeneous solution. The reaction contents were deoxygenated with argon for 20 minutes then sealed with a Teflon screwcap. The quartz tube was placed in a Rayonet photoreactor equipped with (14) 254 nm bulbs and irradiated for 17 hours. The reaction contents were transferred to a 50 mL round bottom flask and concentrated on a rotary evaporator to yield a yellow solid. The crude reaction mixture was purified on a Sephadex G-15 column using water as the eluent to provide compound 207 (0.1567 g, 65%).

Compound 206

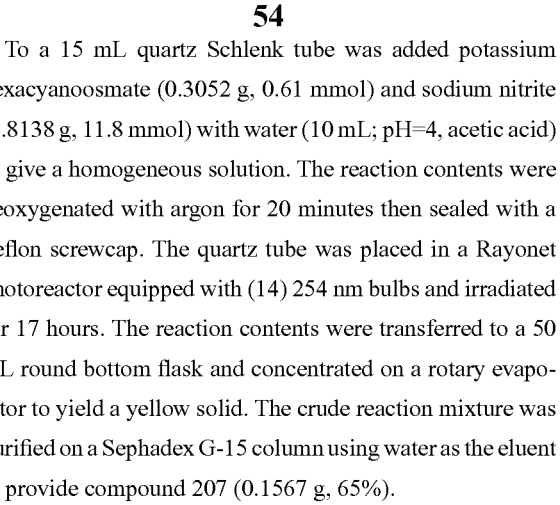

Compound 208

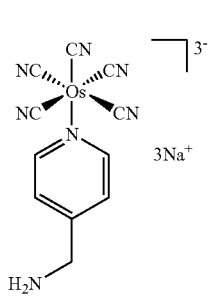

To a 50 mL round bottom flask was added compound 207 (0.1567, 0.40 mmol) and water (2 mL) to give a homogeneous solution. 4-aminomethylpyridine (0.4320 g, 4.0 mmol) was added as a liquid then aqueous sodium hydroxide (7 mL of 3 M, 21 mmol). The reaction mixture was deoxygenated with argon and heated to 65° C. for 72 hours. The reaction contents were cool to room temperature then neutralized by the slow addition of 1 M HCl. The solvent was removed on a rotary evaporator and the crude material purified on a Sephadex G-15 column using water as the eluent to provide compound 208 (0.0922 g, 47%).

Compound 209

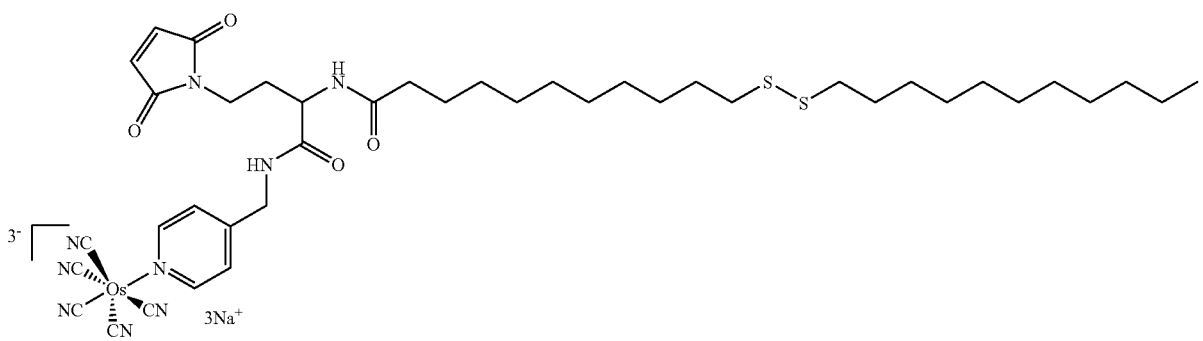

To a 50 mL Schlenk flask will be added 206 (0.0114 g, 0.044 mmol), 2-succinimido-1,1,3,3-tetramethyluronium tetrafluoroborate (0.0140 g, 0.047 mmol), and N,N-dimethylformamide (5 mL). The contents will be stirred under argon, followed by the addition of diisopropylethylamine (7.8 µL, 0.045 mmol). After stirring at room temperature for 1 hour, the solvent will be removed on a rotary evaporator, then the residue dissolved in dry methanol (5 mL). Compound 208 (0.0219 g, 0.044 mmol) will be added as a solid and the contents stirred at room temperature for 18 hours. The solvent will be removed on a rotary evaporator and the residue purified by chromatography on an LH-20 column using methanol as the eluent to provide compound 209.

Example 2

Pentacyanoosmate Branched Molecular Wire Complex

General Considerations. All synthetic manipulations (Schemes S1) were performed under a dry argon atmosphere using standard Schlenk techniques, unless otherwise noted. For reaction media, solvents were dried over neutral alumina via the Dow-Grubbs solvent system[1] acquired from Glass Contours (Laguna Beach, Calif.). These solvents were degassed with argon prior to use.

Materials. Compound 101, 1-ethynyl-4-(trimethylsilylethynyl)benzene, 5-(4-iodophenylethynyl)-[1,2,5]dithiazepane, and compound 208 were synthesized as described previously.[2,3,4,5] All other reagents were purchased from commercial sources and used without further purification unless otherwise noted. Reactions were monitored by TLC (aluminum backed silica gel sheets 60 $F_{254}$; EMD Chemicals, Inc., Gibbstown, N.J.) and spots were visualized by fluorescence quenching upon exposure to UV light.

Experimental Methods:

Scheme S1. Synthesis of compound 107.

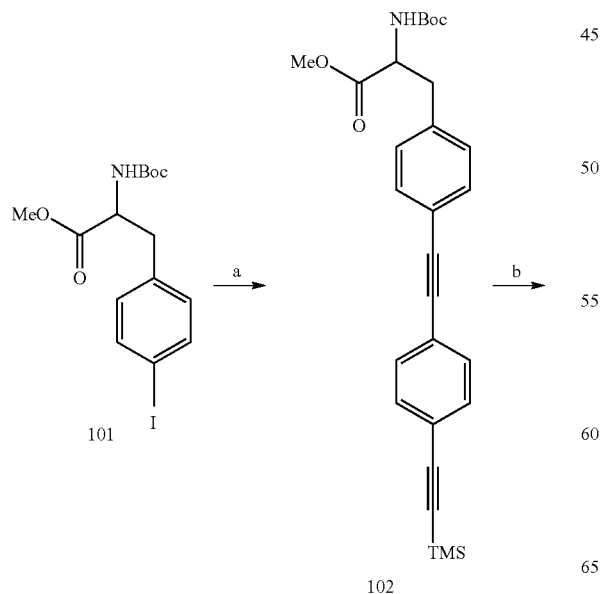

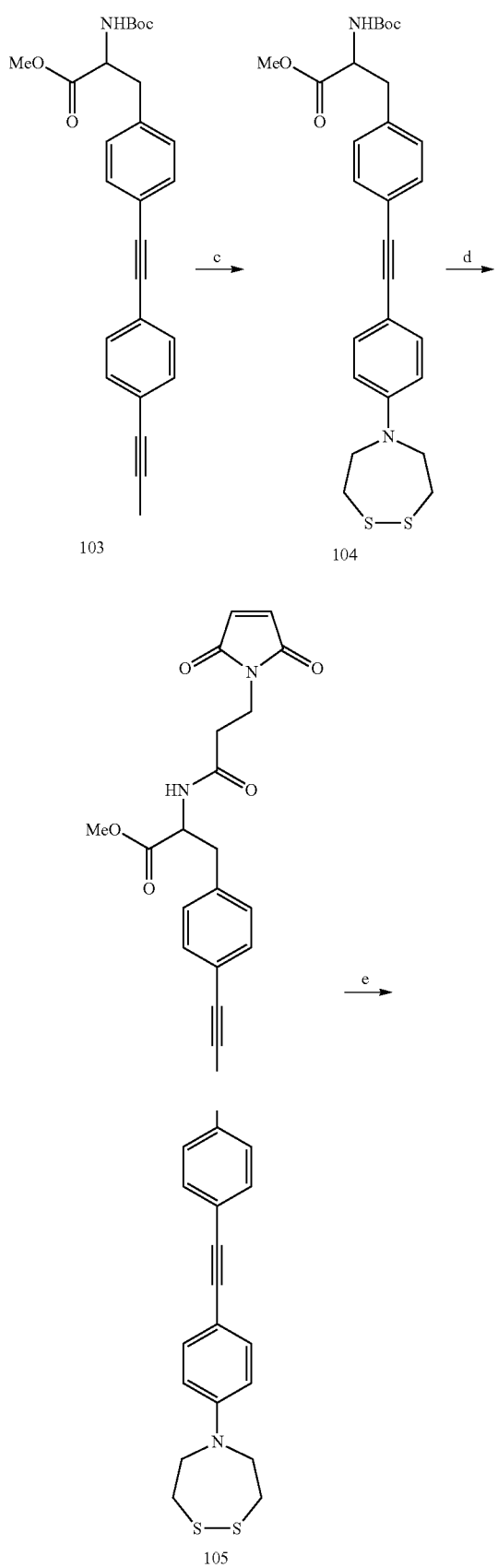

-continued

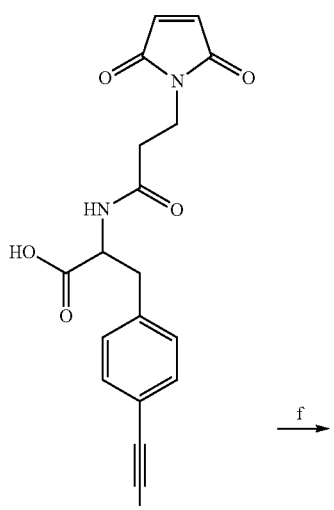

f →

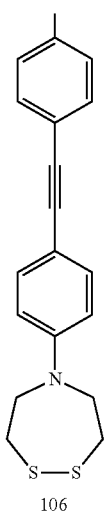

106

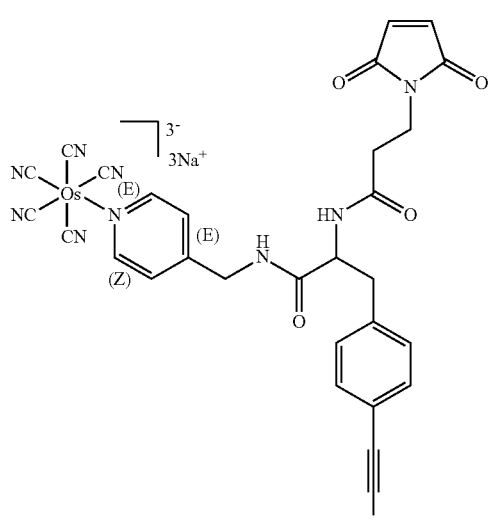

-continued

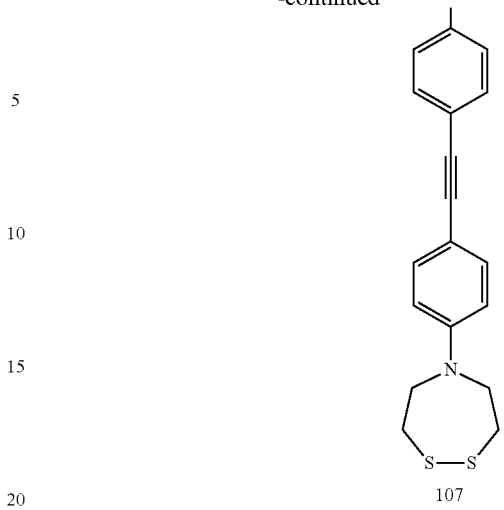

107

Reaction Conditions: (a) 1-ethynyl-4(trimethylsilylethynyl)benzene, Pd(PPh$_3$)$_2$Cl$_2$, CuI, TEA; (b) TBAF; (c) 5-(4-iodophenylethynyl)-[1,2,5] dithiazepane, Pd(PPh$_3$)$_2$Cl$_2$, CuI, TEA; (d) HCl, MPS; (e) LiI; (f) EDC, HOBT, 208.

Compound 102. Compound 101 (1.44 g, 3.55 mmol), 1-ethynyl-4-(trimethylsilylethynyl)benzene (0.705 g, 3.55 mmol), Pd(PPh$_3$)$_2$Cl$_2$ (0.062 g, 0.089 mmol), and CuI (0.017 g, 0.089 mmol) were combined in THF (15 mL). TEA (2.5 mL) was added and the reaction was set to stir at r.t. for 2.5 h under an atmosphere of Ar. The reaction mixture was concentrated in vacuo and the crude residue was purified by column chromatography on silica gel (1:1:5, EtOAC:DCM:hexanes) to yield the pure product as a flaky yellow solid (1.51 g, 3.17 mmol, 89%). ESI-MS (positive, MeOH:DCM) m/z: 498.10 (M+Na)$^+$. $^1$H NMR was consistent with the structure of 102.

Compound 103. Compound 102 (1.44 g, 3.03 mmol) in THF (50 mL) was cooled to ca. −15° C. in an acetonitrile/N$_{2(l)}$ bath. TBAF (1.0 M in THF, 4.5 mL, 4.5 mmol) was added dropwise via syringe. After 20 min, water (2 mL) was added to quench the reaction and the volatiles were removed in vacuo. The crude orange oil was dissolved in EtOAc (200 mL) and washed with water (3×100 mL), dried over Na$_2$SO$_4$, filtered, and concentrated to a crude residue that was purified by column chromatography on silica gel (1:1:3, EtOAc:DCM:hexanes) to yield the pure product as an off-white solid (1.22 g, 3.02 mmol, 99%). $^1$H NMR was consistent with the structure of 103.

Compound 104. Compound 103 (0.533 g, 1.32 mmol), 5-(4-iodophenylethynyl)-[1,2,5]dithiazepane (0.445 g, 1.32 mmol), Pd(PPh$_3$)$_2$Cl$_2$ (0.046 g, 0.066 mmol), and CuI (0.006 g, 0.033 mmol) were combined in THF (5 mL). TEA (1.0 mL) was added and the reaction was heated to 50° C. under an atmosphere of Ar. After 22 h the volatiles were removed in vacuo and the crude residue was purified by column chromatography on silica gel (0.2:0.8:4, EtOAc:hexanes:DCM) to yield the pure product as a greenish yellow solid (0.285 g, 0.470 mmol, 36%). $^1$H NMR was consistent with the structure of 104.

Compound 105. Compound 104 (0.072 g, 0.12 mmol) was dissolved in dioxane (3 mL) and anisole (0.5 mL). HCl (4.0 M in dioxane, 3 mL) was added dropwise and the reaction stirred at r.t. for 1 h. The volatiles were removed in vacuo and the crude yellow solid was used without further purification. NHS-3-maleimidopropionate (MPS) (0.034 g, 0.13 mmol), N,N-dimethylacetamide (4 mL), and TEA (50 µL) were added and the reaction stirred at r.t. overnight. After 15 h, the reaction mixture was poured into water (75 mL) and extracted with DCM (4×50 mL). The organic phase was dried over Na$_2$SO$_4$, filtered, and concentrated to a crude residue that was purified by column chromatography on silica gel (1:2:2, diethyl ether:EtOAc:DCM) to yield the pure product as a yellow solid (0.040 g, 0.060 mmol, 50%). $^1$H NMR was consistent with the structure of 105.

Compound 106. Compound 105 (0.031 g, 0.047 mmol) and ultra dry LiI (0.045 g, 0.34 mmol) were refluxed in dry EtOAc (3 mL) for 24 h in the dark. The reaction mixture was poured into HCl$_{(aq)}$ (0.1 M, 10 mL) with EtOAc (100 mL). The organic phase was washed with HCl$_{(aq)}$ (0.1 M, 2×50 mL), dried over Na$_2$SO$_4$, filtered, and concentrated to a crude residue that was purified by column chromatography on silica gel (0.1:0.5:9.4, acetic acid:MeOH:DCM) to yield the pure product as a yellow solid (0.020 g, 0.031 mmol, 66%). ESI-MS (negative, MeOH) m/z: 684.39 (M+Cl)$^-$. $^1$H NMR was consistent with the structure of 106.

Compound 107. Compound 106 (0.007 g, 0.011 mmol) and compound 208 (0.006 g, 0.013 mmol) are suspended in MeOH (2.5 mL) and THF (0.5 mL). The flask is sonicated and the mixture cooled to 4° C. in an ice bath. 1-Hydroxybenzotriazole (0.1 equiv with respect to 106) in THF (0.5 mL) is added followed by N-(3-dimethylaminopropyl)-N-ethylcarbodiimide-HCl (0.002 g, 0.011 mmol) and TEA (3 μL) and the reaction stirred allow to warm to r.t. overnight. The solvent will be removed in vacuo and the residue purified by chromatography on an LH-20 column using methanol as the eluent to provide compound 107.

We claim:

1. A composition comprising an electrode comprising:
    a) a capture ligand comprising a first functional group;
    b) a first SAM forming species comprising a second functional group; and
    c) a second SAM forming species comprising an electroactive complex (EAM), said EAM selected from the group consisting of:
        (1) a transition metal complex comprising osmium, a bipyridine ligand, and four cyano ligands; and
        (2) a transition metal complex comprising osmium, a pyridine ligand, and five cyano ligands, and
    wherein the second functional group is functional to form a covalent bond to the first functional group of the capture ligand.

2. A composition comprising an electrode comprising:
    a) a capture ligand comprising a first functional group;
    b) a first SAM forming species comprising both a second functional group and an electroactive complex (EAM), wherein
        said EAM comprises a osmium, a bipyridine ligand, and four cyano ligands; and
        said second functional group is functional to form a covalent bond to the first functional group of the capture ligand;
    and
    c) a second SAM forming species comprising a passivation agent.

3. The composition of claim 1 or 2, wherein the second functional group is a maleimide group.

4. The composition of claim 1 or 2, wherein said EAM comprises osmium tetracyano bipyridine.

5. The composition of claim 1 or 2, wherein said EAM comprises osmium pentacyano pyridine.

6. The composition of claim 1 or 2, wherein the bipyridine is attached to both the electrode and the capture ligand.

7. The composition of claim 1 or 2, wherein the pyridine is attached to the electrode.

8. The composition of claim 1 or 2, wherein said electrode is gold and said SAM forming species are covalently attached to said electrode via a sulfur atom.

9. The composition of claim 1 or 2, wherein said electrode is gold and said SAM forming species are covalently attached to said electrode via two sulfur atoms.

10. A composition comprising an array of electrodes, wherein at least one electrode of said array comprises the composition of claim 1 or 2.

11. The composition of claim 1 or 2, wherein said second functional group is chosen from the group consisting of maleimide, imidoester, N-hydroxysuccinimidyl, alkyl halide, aryl halide, alpha-haloacyl, and pyridyl disulfide.

12. The composition of claim 2, wherein the passivation agent is an insulator.

13. A composition comprising an electrode comprising:
    a) a capture ligand comprising a protein and a first functional group comprising cysteine; and
    b) a first SAM forming species comprising a second functional group wherein said second functional group is a maleimide group functional to form a covalent bond to the first functional group of the capture ligand;
    and
    c) a second SAM forming species comprising an electroactive complex (EAM), said EAM selected from the group consisting of:
        (1) a transition metal complex comprising osmium, a bipyridine ligand, and four cyano ligands; and
        (2) a transition metal complex comprising osmium, a pyridine ligand, and five cyano ligands.

14. A composition comprising an electrode comprising:
a) a capture ligand comprising a protein and a first functional group comprising cysteine; and
b) a first SAM forming species comprising both a second functional group and an electroactive complex (EAM) wherein the EAM comprises osmium, a bipyridine ligand, and four cyano ligands, and, wherein
said second functional group is a maleimide group functional to form a covalent bond to the first functional group of the capture ligand; and
said EAM comprises a transition metal and at least one cyano ligand, wherein the transition metal is chosen from the group consisting of ruthenium and osmium; and
c) a second SAM forming species comprising a passivation agent.

15. The composition of claim 13 or 14, wherein the EAM comprises osmium tetracyano bipyridine.

16. The composition of claim 13, wherein the EAM comprises osmium pentacyano pyridine.

17. The composition of claim 13 or 14, wherein the protein is a peptide.

18. The composition of claim 13 or 14, wherein the bipyridine is attached to both the electrode and the capture ligand.

19. The composition of claim 13, wherein the pyridine is attached to the electrode.

* * * * *

```
                        SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: FMOC on N terminus

<400> SEQUENCE: 1

Ala Thr Tyr Pro Leu Pro Ile Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: FMOC on N terminus

<400> SEQUENCE: 2

Tyr Tyr Trp Leu His His Cys
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ac on N terminus

<400> SEQUENCE: 3

Leu His Ile His Arg Thr Leu Ser Ile Gln Gly Gly Gly Gly Ser Cys
1               5                   10                  15

<210> SEQ ID NO 4
<211> LENGTH: 7
<212> TYPE: PRT
<213> ORGANISM: Artificial Sequence
<220> FEATURE:
```

```
<223> OTHER INFORMATION: Synthetic
<220> FEATURE:
<221> NAME/KEY: MOD_RES
<222> LOCATION: (1)..(1)
<223> OTHER INFORMATION: Ac on N terminus

<400> SEQUENCE: 4

His Ser Ser Lys Leu Gln Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Tyr Tyr Trp Leu His His Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ala Thr Tyr Pro Leu Pro Ile Arg
1               5
```